United States Patent [19]
Balducchi et al.

[11] Patent Number: 5,563,318
[45] Date of Patent: Oct. 8, 1996

[54] CORN LETHAL NECROSIS RESISTANT MAIZE AND THE PRODUCTION THEREOF

[75] Inventors: Albert J. Balducchi, Ames; George K. Rufener, II, Johnston; Ronald P. Mowers, Ames, all of Iowa

[73] Assignee: Zeneca Limited, London, England

[21] Appl. No.: 220,905

[22] Filed: Mar. 31, 1994

[51] Int. Cl.$^6$ .............................. A01H 5/00; A01H 1/00; C12M 15/05

[52] U.S. Cl. ................. 800/200; 800/250; 800/DIG. 56; 435/172.3; 47/58; 47/DIG. 1

[58] Field of Search ..................................... 800/200, 205, 800/235, DIG. 56; 47/58.03, 58.05; 435/172.3

[56] References Cited

U.S. PATENT DOCUMENTS 5,159,153  10/1992  Riley ........................................ 800/200

OTHER PUBLICATIONS

Niblett et al. (1978) Biological Abstract #BA65:67154 p. 67157.
Smith et al. (1988) Corn & Corn Improvement "Diseases of Corn".
Ed G. F. Sprague et al. ASA pub #18, pp. 720–722.
Louie et al. (1990) Crop Science vol. 30. pp. 1210–1215.
Louie, Raymond, et al. Genetic Basis of Resistance in Maize Dwarf Mosaic Virus Strains. Crop Science, 31:14–18 (1991).
Mckern, N. M., et al. Confirmation that the Sugarcane Mosaic Virus Subgroup Consists of Four Distinct Potyviruses by Using Peptide Profiles of Coat Proteins, Phytopathology, vol. 81, No. 9, 1025–1029 (1991).
McMullen, Michael D., et al. Identification of a Gene for Resistance to Wheat Streak Mosaic Virus in Maize. Phytopathology, vol. 81, No. 6, 624–627, (1991).

*Primary Examiner*—Gary Benzion
*Attorney, Agent, or Firm*—Dana Rewoldt

[57] ABSTRACT

Maize which has improved resistance to $MDMV_B$ and/or CLN selected by reference to RFLP data for certain chromosome regions associated with the resistance. The method for introgressing the identified chromosomal regions into high yielding inbred lines which are resistant.

9 Claims, 47 Drawing Sheets

| GENOTYPE | MAMR MEAN | STD ERR | FAMR MEAN | STD ERR | SAMR MEAN | STD ERR | N |
|---|---|---|---|---|---|---|---|
| RR | 4.04 | 0.15 | 4.13 | 0.14 | 3.96 | 0.16 | 51 |
| RS | 3.99 | 0.10 | 4.07 | 0.10 | 3.90 | 0.11 | 109 |
| SS | 3.84 | 0.15 | 3.92 | 0.15 | 3.76 | 0.16 | 48 |

U0027_A

| GENOTYPE | MAMR MEAN | STD ERR | FAMR MEAN | STD ERR | SAMR MEAN | STD ERR | N |
|---|---|---|---|---|---|---|---|
| RR | 4.02 | 0.15 | 4.10 | 0.15 | 3.95 | 0.16 | 48 |
| RS | 3.93 | 0.11 | 4.02 | 0.10 | 3.84 | 0.11 | 103 |
| SS | 3.99 | 0.14 | 4.07 | 0.14 | 3.91 | 0.15 | 57 |

U0166_B

| GENOTYPE | MAMR MEAN | STD ERR | FAMR MEAN | STD ERR | SAMR MEAN | STD ERR | N |
|---|---|---|---|---|---|---|---|
| RR | 3.93 | 0.15 | 4.02 | 0.15 | 3.84 | 0.16 | 50 |
| RS | 3.89 | 0.11 | 3.98 | 0.10 | 3.80 | 0.11 | 100 |
| SS | 3.99 | 0.17 | 4.07 | 0.16 | 3.92 | 0.18 | 41 |

U0043_D

| GENOTYPE | MAMR MEAN | STD ERR | FAMR MEAN | STD ERR | SAMR MEAN | STD ERR | N |
|---|---|---|---|---|---|---|---|
| RR | 3.94 | 0.17 | 4.03 | 0.16 | 3.86 | 0.18 | 44 |
| RS | 4.08 | 0.15 | 4.17 | 0.14 | 3.99 | 0.16 | 56 |
| SS | 3.95 | 0.16 | 4.01 | 0.15 | 3.89 | 0.17 | 49 |

B0756_B

| GENOTYPE | MAMR MEAN | STD ERR | FAMR MEAN | STD ERR | SAMR MEAN | STD ERR | N |
|---|---|---|---|---|---|---|---|
| RR | 3.98 | 0.15 | 4.06 | 0.14 | 3.90 | 0.15 | 52 |
| RS | 3.93 | 0.11 | 4.02 | 0.10 | 3.84 | 0.11 | 99 |
| SS | 3.97 | 0.14 | 4.05 | 0.14 | 3.90 | 0.15 | 55 |

N0295_A

| GENOTYPE | MAMR MEAN | STD ERR | FAMR MEAN | STD ERR | SAMR MEAN | STD ERR | N |
|---|---|---|---|---|---|---|---|
| RR | 4.04 | 0.16 | 4.12 | 0.16 | 3.96 | 0.17 | 43 |
| RS | 4.02 | 0.10 | 4.11 | 0.10 | 3.94 | 0.11 | 104 |
| SS | 3.80 | 0.14 | 3.89 | 0.13 | 3.72 | 0.14 | 61 |

N0562_A

| GENOTYPE | MAMR MEAN | STD ERR | FAMR MEAN | STD ERR | SAMR MEAN | STD ERR | N |
|---|---|---|---|---|---|---|---|
| RR | 4.05 | 0.14 | 4.12 | 0.14 | 3.97 | 0.15 | 36 |
| RS | 4.26 | 0.10 | 4.32 | 0.10 | 4.19 | 0.11 | 70 |
| SS | 4.47 | 0.17 | 4.52 | 0.16 | 4.42 | 0.18 | 25 |

U0085_D

| GENOTYPE | MAMR MEAN | STD ERR | FAMR MEAN | STD ERR | SAMR MEAN | STD ERR | N |
|---|---|---|---|---|---|---|---|
| RR | 4.72 | 0.15 | 4.75 | 0.14 | 4.69 | 0.15 | 38 |
| RS | 4.16 | 0.09 | 4.24 | 0.09 | 4.08 | 0.10 | 97 |
| SS | 3.17 | 0.11 | 3.29 | 0.11 | 3.05 | 0.12 | 64 |

B0629_A

| GENOTYPE | MAMR MEAN | STD ERR | FAMR MEAN | STD ERR | SAMR MEAN | STD ERR | N |
|---|---|---|---|---|---|---|---|
| RR | 4.73 | 0.15 | 4.77 | 0.15 | 4.70 | 0.16 | 37 |
| RS | 4.10 | 0.09 | 4.17 | 0.09 | 4.03 | 0.10 | 99 |
| SS | 3.30 | 0.11 | 3.42 | 0.11 | 3.17 | 0.12 | 68 |

| GENOTYPE | MAMR MEAN | STD ERR | FAMR MEAN | STD ERR | SAMR MEAN | STD ERR | N |
|---|---|---|---|---|---|---|---|
| RR | 4.61 | 0.14 | 4.65 | 0.14 | 4.56 | 0.15 | 47 |
| RS | 3.82 | 0.11 | 3.91 | 0.10 | 3.72 | 0.11 | 83 |
| SS | 3.23 | 0.14 | 3.35 | 0.14 | 3.11 | 0.15 | 47 |

B0562_A

| GENOTYPE | MAMR MEAN | STD ERR | FAMR MEAN | STD ERR | SAMR MEAN | STD ERR | N |
|---|---|---|---|---|---|---|---|
| RR | 4.13 | 0.16 | 4.21 | 0.16 | 4.06 | 0.17 | 43 |
| RS | 3.96 | 0.10 | 4.05 | 0.10 | 3.87 | 0.11 | 107 |
| SS | 3.87 | 0.14 | 3.95 | 0.13 | 3.79 | 0.14 | 59 |

N0234_B

| GENOTYPE | MAMR MEAN | STD ERR | FAMR MEAN | STD ERR | SAMR MEAN | STD ERR | N |
|---|---|---|---|---|---|---|---|
| RR | 4.13 | 0.16 | 4.21 | 0.15 | 4.05 | 0.17 | 45 |
| RS | 3.91 | 0.11 | 4.00 | 0.10 | 3.83 | 0.11 | 99 |
| SS | 3.90 | 0.14 | 3.97 | 0.13 | 3.82 | 0.14 | 61 |

N0446_B

| GENOTYPE | MAMR MEAN | STD ERR | FAMR MEAN | STD ERR | SAMR MEAN | STD ERR | N |
|---|---|---|---|---|---|---|---|
| RR | 4.41 | 0.16 | 4.47 | 0.15 | 4.35 | 0.17 | 40 |
| RS | 4.06 | 0.10 | 4.14 | 0.09 | 3.98 | 0.10 | 108 |
| SS | 3.38 | 0.14 | 3.49 | 0.13 | 3.27 | 0.14 | 54 |

U0060_A

| GENOTYPE | MAMR MEAN | STD ERR | FAMR MEAN | STD ERR | SAMR MEAN | STD ERR | N |
|---|---|---|---|---|---|---|---|
| RR | 4.09 | 0.13 | 4.17 | 0.12 | 4.01 | 0.13 | 68 |
| RS | 3.91 | 0.11 | 3.99 | 0.11 | 3.82 | 0.11 | 94 |
| SS | 3.91 | 0.16 | 3.99 | 0.15 | 3.82 | 0.16 | 46 |

U0082_A

| GENOTYPE | MAMR MEAN | STD ERR | FAMR MEAN | STD ERR | SAMR MEAN | STD ERR | N |
|---|---|---|---|---|---|---|---|
| RR | 4.55 | 0.16 | 4.62 | 0.15 | 4.49 | 0.18 | 14 |
| RS | 4.32 | 0.11 | 4.39 | 0.11 | 4.25 | 0.12 | 28 |
| SS | 4.04 | 0.17 | 4.16 | 0.15 | 3.92 | 0.18 | 13 |

B0537_A

| GENOTYPE | MAMR MEAN | STD ERR | FAMR MEAN | STD ERR | SAMR MEAN | STD ERR | N |
|---|---|---|---|---|---|---|---|
| RR | 4.51 | 0.19 | 4.56 | 0.18 | 4.46 | 0.19 | 31 |
| RS | 3.91 | 0.11 | 4.00 | 0.10 | 3.82 | 0.11 | 96 |
| SS | 3.58 | 0.15 | 3.67 | 0.14 | 3.49 | 0.15 | 50 |

N0247_B

| GENOTYPE | MAMR MEAN | STD ERR | FAMR MEAN | STD ERR | SAMR MEAN | STD ERR | N |
|---|---|---|---|---|---|---|---|
| RR | 4.53 | 0.14 | 4.58 | 0.14 | 4.48 | 0.15 | 48 |
| RS | 4.03 | 0.09 | 4.12 | 0.09 | 3.94 | 0.10 | 108 |
| SS | 3.32 | 0.13 | 3.43 | 0.13 | 3.22 | 0.14 | 53 |

N0296_A

| GENOTYPE | MAMR MEAN | STD ERR | FAMR MEAN | STD ERR | SAMR MEAN | STD ERR | N |
|---|---|---|---|---|---|---|---|
| RR | 4.51 | 0.15 | 4.56 | 0.15 | 4.45 | 0.16 | 44 |
| RS | 4.00 | 0.10 | 4.08 | 0.10 | 3.92 | 0.10 | 104 |
| SS | 3.51 | 0.13 | 3.61 | 0.13 | 3.40 | 0.14 | 58 |

| GENOTYPE | MAMR MEAN | STD ERR | FAMR MEAN | STD ERR | SAMR MEAN | STD ERR | N |
|---|---|---|---|---|---|---|---|
| RR | 4.42 | 0.17 | 4.48 | 0.16 | 4.35 | 0.17 | 39 |
| RS | 4.01 | 0.10 | 4.08 | 0.10 | 3.93 | 0.11 | 100 |
| SS | 3.53 | 0.13 | 3.63 | 0.13 | 3.42 | 0.14 | 60 |

B0616_A

| GENOTYPE | MAMR MEAN | STD ERR | FAMR MEAN | STD ERR | SAMR MEAN | STD ERR | N |
|---|---|---|---|---|---|---|---|
| RR | 4.07 | 0.15 | 4.13 | 0.14 | 4.01 | 0.16 | 50 |
| RS | 4.02 | 0.10 | 4.11 | 0.10 | 3.93 | 0.10 | 111 |
| SS | 3.78 | 0.15 | 3.86 | 0.14 | 3.69 | 0.16 | 50 |

B0318_B

| GENOTYPE | MAMR MEAN | STD ERR | FAMR MEAN | STD ERR | SAMR MEAN | STD ERR | N |
|---|---|---|---|---|---|---|---|
| RR | 4.04 | 0.15 | 4.10 | 0.15 | 3.98 | 0.16 | 47 |
| RS | 4.05 | 0.10 | 4.13 | 0.09 | 3.96 | 0.10 | 117 |
| SS | 3.47 | 0.17 | 3.57 | 0.17 | 3.36 | 0.18 | 37 |

B0318AB

| GENOTYPE | MAMR MEAN | STD ERR | FAMR MEAN | STD ERR | SAMR MEAN | STD ERR | N |
|---|---|---|---|---|---|---|---|
| RR | 4.51 | 0.17 | 4.56 | 0.17 | 4.46 | 0.18 | 32 |
| RS | 4.05 | 0.10 | 4.15 | 0.10 | 3.96 | 0.11 | 90 |
| SS | 3.35 | 0.15 | 3.47 | 0.14 | 3.24 | 0.16 | 42 |

N0212_B

| GENOTYPE | MAMR MEAN | STD ERR | FAMR MEAN | STD ERR | SAMR MEAN | STD ERR | N |
|---|---|---|---|---|---|---|---|
| RR | 4.20 | 0.15 | 4.27 | 0.15 | 4.13 | 0.16 | 48 |
| RS | 3.89 | 0.10 | 3.99 | 0.10 | 3.80 | 0.10 | 114 |
| SS | 3.80 | 0.16 | 3.88 | 0.16 | 3.73 | 0.17 | 43 |

N0212AB

| GENOTYPE | MAMR MEAN | STD ERR | FAMR MEAN | STD ERR | SAMR MEAN | STD ERR | N |
|---|---|---|---|---|---|---|---|
| RR | 4.01 | 0.14 | 4.10 | 0.14 | 3.93 | 0.15 | 55 |
| RS | 3.99 | 0.10 | 4.07 | 0.10 | 3.91 | 0.11 | 104 |
| SS | 3.60 | 0.17 | 3.72 | 0.16 | 3.49 | 0.18 | 39 |

N0212BB

| GENOTYPE | MAMR MEAN | STD ERR | FAMR MEAN | STD ERR | SAMR MEAN | STD ERR | N |
|---|---|---|---|---|---|---|---|
| RR | 4.04 | 0.17 | 4.11 | 0.16 | 3.97 | 0.17 | 42 |
| RS | 3.75 | 0.11 | 3.86 | 0.11 | 3.64 | 0.12 | 93 |
| SS | 4.04 | 0.15 | 4.10 | 0.14 | 3.97 | 0.15 | 54 |

U0016_A

| GENOTYPE | MAMR MEAN | STD ERR | FAMR MEAN | STD ERR | SAMR MEAN | STD ERR | N |
|---|---|---|---|---|---|---|---|
| RR | 4.28 | 0.22 | 4.36 | 0.20 | 4.20 | 0.24 | 9 |
| RS | 4.38 | 0.11 | 4.44 | 0.10 | 4.33 | 0.12 | 37 |
| SS | 4.47 | 0.09 | 4.53 | 0.08 | 4.42 | 0.09 | 60 |

B0833_D

| GENOTYPE | MAMR MEAN | STD ERR | FAMR MEAN | STD ERR | SAMR MEAN | STD ERR | N |
|---|---|---|---|---|---|---|---|
| RR | 3.93 | 0.15 | 4.02 | 0.14 | 3.85 | 0.15 | 51 |
| RS | 3.81 | 0.10 | 3.90 | 0.10 | 3.71 | 0.10 | 112 |
| SS | 4.41 | 0.17 | 4.45 | 0.16 | 4.37 | 0.18 | 39 |

FIG. 1D

| ND409_B GENOTYPE | MAMR MEAN | STD ERR | FAMR MEAN | STD ERR | SAMR MEAN | STD ERR | N |
|---|---|---|---|---|---|---|---|
| RR | 3.88 | 0.16 | 3.97 | 0.16 | 3.79 | 0.17 | 43 |
| RS | 3.88 | 0.10 | 3.97 | 0.09 | 3.80 | 0.10 | 120 |
| SS | 4.18 | 0.17 | 4.24 | 0.17 | 4.11 | 0.18 | 38 |

| BD625_A GENOTYPE | MAMR MEAN | STD ERR | FAMR MEAN | STD ERR | SAMR MEAN | STD ERR | N |
|---|---|---|---|---|---|---|---|
| RR | 3.89 | 0.16 | 3.98 | 0.16 | 3.80 | 0.17 | 43 |
| RS | 3.94 | 0.10 | 4.02 | 0.09 | 3.85 | 0.10 | 126 |
| SS | 4.15 | 0.18 | 4.23 | 0.18 | 4.08 | 0.19 | 34 |

| ND579_A GENOTYPE | MAMR MEAN | STD ERR | FAMR MEAN | STD ERR | SAMR MEAN | STD ERR | N |
|---|---|---|---|---|---|---|---|
| RR | 4.03 | 0.19 | 4.13 | 0.18 | 3.94 | 0.19 | 36 |
| RS | 3.81 | 0.13 | 3.90 | 0.12 | 3.71 | 0.13 | 80 |
| SS | 3.93 | 0.16 | 4.00 | 0.15 | 3.86 | 0.16 | 52 |

| ND373_A GENOTYPE | MAMR MEAN | STD ERR | FAMR MEAN | STD ERR | SAMR MEAN | STD ERR | N |
|---|---|---|---|---|---|---|---|
| RR | 4.63 | 0.17 | 4.68 | 0.17 | 4.59 | 0.18 | 32 |
| RS | 4.11 | 0.09 | 4.18 | 0.09 | 4.04 | 0.10 | 111 |
| SS | 3.41 | 0.12 | 3.53 | 0.12 | 3.29 | 0.12 | 67 |

| ND114_A GENOTYPE | MAMR MEAN | STD ERR | FAMR MEAN | STD ERR | SAMR MEAN | STD ERR | N |
|---|---|---|---|---|---|---|---|
| RR | 3.99 | 0.14 | 4.07 | 0.13 | 3.91 | 0.14 | 61 |
| RS | 4.03 | 0.10 | 4.11 | 0.10 | 3.95 | 0.11 | 106 |
| SS | 3.77 | 0.17 | 3.86 | 0.16 | 3.67 | 0.18 | 40 |

FIG. 2

| CHROM | MAP # | | MAMR | | | | FAMR | | | | SAMR | | |
|---|---|---|---|---|---|---|---|---|---|---|---|---|---|
| | | SIG | PR>F | RSQ | FALC_A | PR>T | SIG | PR>F | RSQ | FALC_A | PR>T | SIG | PR>F | RSQ | FALC_A | PR>T |
| 3 | B0562 A | | 0.45 | 0.01 | 0.13 | 0.21 | | 0.44 | 0.01 | 0.13 | 0.20 | | 0.47 | 0.01 | 0.13 | 0.23 |
| 3 | N0234 B | | 0.46 | 0.01 | 0.12 | 0.26 | | 0.42 | 0.01 | 0.12 | 0.23 | | 0.49 | 0.01 | 0.12 | 0.29 |
| 3 | N0446 B | 0 | 0.00 | 0.12 | 0.52 | 0.00 | 0 | 0.00 | 0.12 | 0.49 | 0.00 | 0 | 0.00 | 0.12 | 0.54 | 0.00 |
| 3 | U0060 A | | 0.52 | 0.01 | 0.09 | 0.37 | | 0.51 | 0.01 | 0.09 | 0.37 | | 0.53 | 0.01 | 0.09 | 0.38 |
| 3 | U0082 A | | 0.10 | 0.09 | 0.26 | 0.03 | | 0.10 | 0.08 | 0.23 | 0.03 | | 0.09 | 0.09 | 0.28 | 0.03 |
| 3 | B0537 A | 0 | 0.00 | 0.08 | 0.46 | 0.00 | 0 | 0.00 | 0.08 | 0.44 | 0.00 | 0 | 0.00 | 0.08 | 0.48 | 0.00 |
| 3 | N0247 B | 0 | 0.00 | 0.16 | 0.60 | 0.00 | 0 | 0.00 | 0.16 | 0.57 | 0.00 | 0 | 0.00 | 0.16 | 0.63 | 0.00 |
| 3 | N0296 A | 0 | 0.00 | 0.11 | 0.50 | 0.00 | 0 | 0.00 | 0.11 | 0.47 | 0.00 | 0 | 0.00 | 0.11 | 0.52 | 0.00 |
| 3 | N0296AD | 0 | 0.00 | 0.08 | 0.44 | 0.00 | 0 | 0.00 | 0.08 | 0.42 | 0.00 | 0 | 0.00 | 0.09 | 0.46 | 0.00 |
| 3 | B0616 A | | 0.31 | 0.01 | 0.15 | 0.17 | | 0.31 | 0.01 | 0.13 | 0.19 | | 0.31 | 0.01 | 0.16 | 0.15 |
| 3 | B0318 B | 5 | 0.01 | 0.04 | 0.29 | 0.01 | 5 | 0.01 | 0.04 | 0.27 | 0.02 | 5 | 0.01 | 0.04 | 0.31 | 0.01 |
| 3 | B0318AB | 0 | 0.00 | 0.15 | 0.58 | 0.00 | 0 | 0.00 | 0.14 | 0.55 | 0.00 | | 0.00 | 0.15 | 0.61 | 0.00 |
| 3 | N0212 B | | 0.15 | 0.02 | 0.20 | 0.08 | | 0.16 | 0.02 | 0.19 | 0.07 | | 0.14 | 0.02 | 0.20 | 0.08 |
| 3 | N0212AB | | 0.12 | 0.02 | 0.21 | 0.07 | | 0.15 | 0.02 | 0.19 | 0.08 | | 0.09 | 0.02 | 0.22 | 0.06 |
| 3 | N0212BB | | 0.18 | 0.01 | 0.00 | 0.98 | | 0.26 | 0.01 | 0.01 | 0.94 | | 0.12 | 0.01 | -0.00 | 0.99 |
| 3 | U0016 A | | 0.64 | 0.05 | -0.10 | 0.42 | | 0.65 | 0.04 | -0.08 | 0.45 | | 0.64 | 0.05 | -0.11 | 0.40 |
| 5 | B0833 D | 1 | 0.01 | 0.01 | -0.24 | 0.03 | | 0.02 | 0.01 | -0.22 | 0.05 | | 0.01 | 0.01 | -0.26 | 0.03 |
| 5 | N0409 B | | 0.31 | 0.01 | -0.15 | 0.21 | | 0.34 | 0.01 | -0.14 | 0.23 | | 0.29 | 0.01 | -0.16 | 0.20 |
| 5 | B0625 A | | 0.52 | 0.01 | -0.13 | 0.29 | | 0.52 | 0.01 | -0.12 | 0.30 | | 0.52 | 0.01 | -0.14 | 0.28 |
| 5 | N0579 A | | 0.59 | 0.01 | 0.05 | 0.67 | | 0.58 | 0.01 | 0.06 | 0.59 | | 0.59 | 0.01 | 0.04 | 0.75 |
| 5 | U0147 B | | 0.62 | 0.01 | 0.10 | 0.35 | | 0.58 | 0.01 | 0.10 | 0.31 | | 0.66 | 0.01 | 0.10 | 0.38 |
| 5 | U0027 A | | 0.86 | 0.00 | 0.02 | 0.87 | | 0.88 | 0.00 | 0.02 | 0.87 | | 0.85 | 0.00 | 0.02 | 0.88 |
| 5 | U0166 B | | 0.87 | 0.00 | -0.03 | 0.78 | | 0.90 | 0.00 | -0.02 | 0.84 | | 0.84 | 0.00 | -0.04 | 0.73 |
| 5 | U0043 D | | 0.78 | 0.00 | -0.00 | 0.97 | | 0.72 | 0.00 | 0.01 | 0.94 | | 0.82 | 0.00 | -0.02 | 0.89 |
| 5 | B0756 B | | 0.96 | 0.00 | -0.00 | 0.97 | | 0.97 | 0.00 | 0.01 | 0.93 | | 0.95 | 0.00 | -0.02 | 1.00 |
| 5 | N0295 A | | 0.38 | 0.01 | 0.12 | 0.26 | | 0.36 | 0.01 | 0.12 | 0.25 | | 0.41 | 0.01 | 0.12 | 0.27 |
| 5 | N0562 A | | 0.17 | 0.03 | -0.21 | 0.06 | | 0.18 | 0.03 | -0.20 | 0.07 | | 0.17 | 0.03 | -0.22 | 0.06 |
| 6 | U0085 D | 0 | 0.00 | 0.29 | 0.77 | 0.00 | 0 | 0.00 | 0.28 | 0.73 | 0.00 | 0 | 0.00 | 0.29 | 0.82 | 0.00 |
| 6 | B0629 A | 0 | 0.00 | 0.23 | 0.72 | 0.00 | 0 | 0.00 | 0.22 | 0.67 | 0.00 | 0 | 0.00 | 0.24 | 0.76 | 0.00 |
| 6 | U0059 B | 0 | 0.00 | 0.22 | 0.69 | 0.00 | 0 | 0.00 | 0.21 | 0.65 | 0.00 | 0 | 0.00 | 0.22 | 0.73 | 0.00 |
| 6 | N0373 A | 0 | 0.00 | 0.16 | 0.61 | 0.00 | 0 | 0.00 | 0.15 | 0.57 | 0.00 | 0 | 0.00 | 0.16 | 0.65 | 0.00 |

CHROMOSOME 1-B

CHROMOSOME 1-C

CHROMOSOME 1-D

CHROMOSOME 2-A

CHROMOSOME 5-B

CHROMOSOME 5-C

CHROMOSOME 5-D

CHROMOSOME 6-A

CHROMOSOME 6-D

CHROMOSOME 7-A

CHROMOSOME 7-B

CHROMOSOME 8-D

FIG. 5

|  | Average*<br>Percent<br>Infection<br>(0-100)<br>100=Worst | Average**<br>Severity<br>Rating<br>(1-9)<br>9=Best |
|---|---|---|
| Standard Tolerant Hybrid Check<br>= Public Line Cross (B68Ht × Pa405) | 0.0 | 9.00 |
| ICI Seeds Commercial Hybrid<br>= 563 × 211 | 90.0 | 1.25 |
| Commercial Hybrid 3162 | 82.5 | 2.00 |
| Commercial Hybrid 3245 | 97.5 | 1.25 |
| ZS71 × 211 | 5.0 | 7.25 |
| ZS44 × 211 | 5.0 | 7.25 |
| ZS13 × 563<br>= the progenitor of 3 of the $211_{CLN}$ conversions | 42.5 | 3.75 |
| ZS51 × 563<br>= the progenitor of 1 of the $211_{CLN}$ conversions | 52.5 | 3.25 |

\* Average response from 10 plants in each of 2 reps at 2 locations.

\*\* Average response of 2 plots at each of 2 locations.

CORN LETHAL NECROSIS RESISTANT MAIZE AND THE PRODUCTION THEREOF

FIELD OF THE INVENTION

This invention relates to a maize plant and a method of producing the same, which is resistant to corn lethal necrosis (CLN). More specifically, the maize plant has been identified to be resistant to CLN and specifically to a component of CLN, Maize Dwarf Mosaic Virus strain B which will hereinafter simply be referred to as $MDMV_B$. Additionally this invention relates to the introgression in maize of genetic material capable of causing the plant to be resistant to CLN and $MDMV_B$. Additionally, the present invention relates to a method of introgression of the desired genetic material from one or more parent plants into the progeny with precision and accuracy.

BACKGROUND

Worldwide maize (corn) is in large demand as a source of calories for animal and human consumption. The availability of maize can be impacted by nature through weather disasters or by insects or by plant disease. Nature's impact is especially strong because the majority of the maize is grown in limited areas. Thus, insects and plant disease are often transmitted from field to field and cover large corn growing regions. Corn production can be significantly decreased by maize diseases such as Head Smut, CLN, Gray Leaf Spot, Rust, and Maize Chlorotic Dwarf Virus (MCDV). Because of the impact that pests and disease can have on the production of corn, there has understandably been great public interest in developing plants that are disease resistant or pest resistant. Correspondingly, there has been extensive research in breeding corn lines that have these types of resistance.

Occasionally, disease resistant maize is developed by traditional breeding methods; unfortunately however, there is usually a reduction in desirable agronomic traits of the maize plant when disease resistance is introduced. This trade off between desirable agronomic traits in a corn plant and the disease resistances are primarily due to the traditional method by which disease resistance is transferred into the elite inbred. Plants that have disease resistance frequently are unadapted germplasm. Adapted germplasm is germplasm which is specifically bred and selected for use in a commercial environment whereas unadapted germplasm is usually not bred for commercial use. Often unadapted germplasm contains the desired resistance and therefore unadapted germplasm is employed to introduce the desired disease resistance into adapted commercial germplasm. A large portion of chromosomal material from the genotype of the unadapted germplasm is crossed or otherwise introduced into the adapted germplasm. Because the portion of the unadapted germplasm which contains disease resistance is not identified nor located, it cannot be readily tracked when introduced into the adapted germplasm. Therefore, when carrying the disease resistance portion of the genotype from the unadapted germplasm into the adapted germplasm, a variety of the unadapted germplasm's less desirable agronomic traits are often retained and expressed in the resultant resistant plant.

The CLN disease in maize is a disease complex that consists of not just one virus, but at least two viruses to infect the plant. The CLN disease complex usually requires a combination of $MDMV_B$ and maize chlorotic mottle virus (MCMV) to infect a single plant. Traditional methods of plant breeding have been employed in an attempt to transfer resistance to CLN or $MDMV_B$ into commercially viable germplasm for decades. The result has been an occasional inbred line which shows some tolerance; however, the ability to produce a truly resistant plant with genetically desirable traits requires identification of the location of the resistant chromosomal material. Most corn lines considered to be tolerant to CLN tend to lack desirable agronomic traits such as low grain moisture at harvest, high yields per acre, and low percentage of stalk or root lodging.

MDMV has a variety of strains. There is MDMV strain A, $MDMV_B$ along with other types of strains which have been identified. There has been an ongoing debate on how and where in the potyvirus groups $MDMV_B$ should be classified because the status of Sugar Cane Mosaic Virus (SCMV) strains have not been clearly identified. Within the strains, there appear to be four discernible potyvirus groups: Johnsongrass Mosaic Virus (JGMV), Maize Dwarf Mosaic Virus (MDMV), Sorghum Mosaic Virus (SrMV), and SCMV. Through protein profiles of seventeen strains, $MDMV_B$ has been identified as being classified among the Sugar Cane Mosaic Virus (SCMV) group. Additionally other strains of SCMV include: Sugar Cane Mosaic Virus strain A, Sugar Cane Mosaic Virus strain BC ($SCMV_{BC}$), Sugar Cane Mosaic Virus strain D, Sugar Cane Mosaic Virus strain Isis, and Sugar Cane Mosaic virus-SC. There also appears to be a subset of profiles within this group including Sugar Cane Mosaic Virus strain BC and $MDMV_B$. These two are more closely linked by profile than are the other four viruses. This subset may be associated with the fact that neither $MDMV_B$ nor $SCMV_{BC}$ tend to infect sugar cane.

MDMV strains are distributed worldwide and are important in their affect both on the growth and yield of dent corn and sweet corn. Two strains which are detrimental to the United States corn industry are $MDMV_A$ which is found usually in the eastern United States, and $MDMV_B$, which occurs in the Midwest.

Irrespective of how $MDMV_B$ is taxonomically identified, it is an essential component of CLN. Thus resistance to $MDMV_B$ in a plant usually results in resistance to CLN. $MDMV_B$ is transmitted most often by an insect vector, however, it can be transmitted through mechanical means directly from infected plant to noninfected plant. $MCMV_B$ is frequently vectored by greenbugs and corn leaf aphids. Other vectors of $MDMV_B$ include *Rhopalosiphum maidis, R. padi, Myzus persicae,* and *Schizaphis graminum.* MCMV, which is another component of CLN, has been shown to be vectored by corn rootworm beetles.

Symptoms of the infection in a plant of either MCMV or $MDMV_B$ include mottling of the leaves, in a light greenish color. When both of the viruses occur in the same plant, i.e. CLN, there is a bright yellow-green mottling of the leaves which persists to the end of the growing season. CLN can infect plants at all stages of development, and the yield loss is greatest when the infection occurs at the younger stages of the plant life. Toward the end of the season the leaves may die inwardly from the margins with eventual death of the mature plant usually from the top down. The ears of infected CLN plants often are small and distorted having very little kernel development. Some infected plants are barren if the infection occurred early in development.

Hitherto, few, if any, agronomically desirable varieties of corn having resistance to CLN and specifically to $MDMV_B$ and having the necessary agronomic traits for commercial production have been produced. Some resistant sources such as the material used as a donor Pa405 are known but the genetic background of Pa405 evidences agronomically undesirable characteristics such that Pa405 is not presently commercially viable in hybrid combinations. Given that pursuant to this invention it has been discovered that a number of genes control resistance to $MDMV_B$, a progeny plant containing the desired mix of agronomic traits (which make it commercially viable under the industry standards of 1994) and CLN and specifically $MDMV_B$ resistant genes within its genome is expected to be an extremely rare occurrence indeed.

One of the fundamental principles of maize breeding is the production of a hybrid by the combination of two inbreds. Thus there is an ongoing development of new inbreds. An inbred is a plant which has become homozygous in almost all gene loci. There are two germplasm sources for producing new inbreds. One source is germplasm that has been genetically engineered; the second source is adapted germplasm. This invention relates to the use of adapted germplasm and not to genetically engineered germplasm. In a conventional breeding program, pedigree breeding and recurrent selection breeding methods are employed to develop new inbred lines with desired resistant traits. Maize breeding programs attempt to develop these inbred lines by self pollinating the plants and selecting the desirable plants from the populations. An inbred produces a uniform population of hybrid plants when crossed with a second, different homozygous line, i.e., inbred. Inbreds tend to have poor vigor and low yield; however, the progeny of an inbred cross usually evidences high vigor and high yield. The progeny of a cross between two inbreds is often identified as an $F_1$ hybrid. The resultant $F_1$ hybrids which may be heterozygous at a number of gene loci, are evaluated to determine whether they show the resistant trait and agronomically important and desirable traits. Identification of desirable agronomic traits has typically been done by breeders' expertise. A plant breeder identifies a desired trait for the area in which plants are to be grown and attempts to develop inbreds which appear to pass the desirable trait or traits onto the hybrid.

Conventional plant breeders rely on phenotypic traits of the inbreds for selection purposes. Modern plant breeding technology utilizes molecular techniques which allows selection at the chromosomal level. One method of looking at plant genotypes is to use Restriction Fragment Length Polymorphisms (RFLPs) which provide a more precise method for identifying the chromosomal regions which affect the agronomic traits in the plant genome which the plant breeder is attempting to introgress into the inbred line for ultimate expression in the hybrid.

RFLPs can be used to identify specific chromosomal regions. Maize has ten chromosomes. Each chromosome has a short arm with a distal and proximal end and a long arm having a distal and proximal end. Between the short arm proximal end and long arm proximal end is a centromere. Each chromosome is made up of strands of the deoxyribonucleic acid (DNA) molecule which have a specific nucleic acid sequence. Selected restriction endonucleases will identify a specific base sequence and cleave the DNA molecule wherever this sequence occurs. The resultant cleaved portions are called restriction fragments. These restriction fragments can be separated by size by electrophoresis through agarose gels.

The DNA of two individual maize plants will differ in sequence at a variety of sites. Because of this difference, restrictive endonucleases may cleave an individual's DNA at a different site or location than the other individual's DNA. A polymorphism in the length of restriction fragments is produced when the fragments of the two individuals have different lengths. A polymorphism is detected by placing the fragments on a agarose gel electrophoresis and allowing them to separate by size over distance. A southern blot is then used. The fragments of the DNA are physically transferred on to a membrane, then nucleic acid hybridization detects the sequences by hybridization of the single strand of DNA (probe) on the southern blot. The nucleic acid reforms double stranded DNA. A labelled probe is used to detect a particular (DNA) sequence. One method is to use a radioactive labelled probe such that the DNA fragment will be identifiable through autoradiography techniques.

A variety of genes have been mapped and identified using RFLPs. Certain polymorphisms (molecular markers) are used to identify chromosomal areas associated with certain traits. A large number of molecular markers including RFLPs have been applied to the maize genome and a detailed maize genetic linkage map that can be used to localize important genes has been constructed.

A variety of traits have been identified by RFLPs; for example, P1 pericarp color has been linked to UMC185(P1) on the short arm of chromosome one of the maize plant. Probes BNL6.29 and UMC85 on chromosome six of the maize plant have been identified with $MDMV_A$ resistance in maize. Likewise, a variety of other traits have been genetically identified and placed on the maize genetic linkage map.

It would appear that once a desired trait is recognized by virtue of having a desired gene located between flanking probes in a maize plant by the use of RFLPs, that trait should be readily introgressed into an inbred line. Unfortunately, although RFLPs are a tool which can be employed to help identify the chromosomal region to which the trait appears to be linked, RFLPs are not a solution in and of themselves, they are simply a tool of identification. Furthermore, it is difficult in many instances to identify polymorphisms for the cross making the location of the desired gene difficult to identify and/or select. It should be noted that the chromosomal regions associated with CLN and specifically $MDMV_B$ resistance have not been identified or mapped by probes.

Because of the difficulties attendant with working with the CLN specifically $MDMV_B$ trait almost nothing has hitherto been conclusively known about the genes responsible, for example the number of genes involved, their action, and where they are located on the maize chromosomes. There is a need for the identification of the location of genes associated with CLN and $MDMV_B$ which permit their tracking when introgressed into a new plant through traditional breeding techniques. There also remains a need for a method of transferring CLN and/or $MDMV_B$ resistance to a corn plant that has desirable agronomic traits. There remains a need for the development of CLN and $MDMV_B$ resistant inbreds and commercial viable hybrids.

SUMMARY OF THE INVENTION

An object of the present invention is to provide a maize line which exhibits resistance to CLN without significant deterioration of the combining ability of inbred lines and the consequent loss of yield and other agronomically desirable traits in hybrid combinations.

Another object of the present invention is to provide a maize line which exhibits resistance to $MDMV_B$ without significant deterioration of the combining ability of inbred lines and the consequent loss of yield and other agronomically desirable traits in hybrid combinations.

A further object of the invention is to provide a commercially viable CLN resistant hybrid.

An additional object of the invention is to provide a commercially viable $MDMV_B$ resistant hybrid.

Yet another object of the present invention is to provide a breeding method to identify and track chromosomal regions in plants which contain CLN resistance.

Another object of the present invention is to provide a breeding method to identify and track chromosomal regions in plants which contain $MDMV_B$ resistance.

Still another object of the present invention is to provide a method of maize breeding in which the selection of plants for further breeding purposes is by using RFLP's to identify plants as having resistance to CLN and/or $MDMV_B$.

Broadly then, the present invention includes an improved inbred maize line, being derived from a first parent which evidences a resistance to $MDMV_B$ in hybrid combination and a second parent which evidences a susceptibility to $MDMV_B$ and has elite germplasm with desirable yield and moisture characteristics in hybrid combination, and wherein the improved inbred line has the resistance to CLN, in hybrid combination, not significantly less than that of the first parent in the same hybrid combination, and yield and moisture characteristics which are not significantly less than those of the second parent in the same hybrid combination.

Furthermore, the present invention includes an elite inbred maize plant, and parts thereof exhibiting resistance to CLN, comprising a genome which is homozygous in respect to genes within identifiable chromosomal regions conferring resistance to CLN and genes specifying high yield in hybrid combination, the genome being entirely of maize origin.

Broadly then, the present invention encompasses a maize plant having resistance to CLN, the genome of which contains genes associated with CLN resistance or $MDMV_B$ at one or more than one locus selected from the group consisting of: (locus 1) chromosome 3, map units 45 and 106; (locus 3) chromosome 6, map units 0 and 18; references to map units and chromosomal locations being references to the maize chromosome map published for the 1993 Maize Genetics Cooperation NewsLetter March 15, 1993 at FIGS. 3. A plant which is homozygous at each of the loci numbered 1 to 3. A plant in which the donor parent is selected from the group consisting of the corn line designated Pa405, progenitors thereof, resistant progeny thereof and resistant hybrids. An inbred maize line, designated ZS19 or $563_{MDMVB.44}$ or $211_{CLN.1}$ or $211_{CLN.2}$ or $211_{CLN.3}$ having improved resistance to CLN.

Additionally, the present invention is related to the production of hybrids using the converted inbreds or progeny of the converted inbreds. Thus the present invention includes a hybrid maize plant, or parts of the plant comprising the progeny of a cross between first and second inbred lines, genes conferring resistance to $MDMV_B$ and/or CLN being present in the homozygous state in the genome of one or other or both of the the first and second inbred lines such that the genomes of the first and second inbreds together donate to the hybrid a complement of genes necessary to confer the resistance to $MDMV_B$ and/or CLN.

The present invention furthermore includes a method for the production of an inbred maize plant adapted for conferring, in hybrid combination with a suitable second inbred, resistance to $MDMV_B$ and/or CLN, comprising selecting a first donor parental line possessing the desired resistance and crossing same with an elite, high yielding second parental line to produce a segregating plant population.

Screening the plant population for identified chromosomal loci of one or more genes associated with the resistance trait; selecting plants from the population having the identified chromosomal loci for further crossing and selection, and repeating the crossing and selection until a line is obtained which is homozygous for the resistance trait at the loci and has the necessary combining ability to give agronomically acceptable characteristics in hybrid combination.

A recombined linkage block as present in chromosome 6 of the maize line ZS19, containing the arrangement of alleles Pa405:563 with crossovers between the end of the chromosome and map references 18, the Pa405 insertion containing loci 3.

A recombined linkage block as present in chromosome 3 of the maize line ZS19, containing the arrangement of alleles 563:P405:563 with crossovers between map references 45–106 and the Pa405 insertion containing locus 1.

A recombined linkage block as present in chromosome 5 of any of the maize lines including $211_{CLN.1}$, $211_{CLN.2}$, $211_{CLN.3}$, $211_{CLN.4}$ containing the arrangement of alleles Pa405:211 between the end of the chromosome and map reference 14 the Pa405 insertion containing locus 2.

Similarly, the present invention encompasses a recombinantion block on chromosomes 3 and 6 of any of the $211_{CLN.1-.4}$ containing the arrangement of alleles 211:Pa405:211 on chromosome 3 and Pa405:211 on chromosome 6 and containing loci 1 and 3 respectively on these Pa405 allele sites. An improved first inbred maize line adapted to form a hybrid combination with a second inbred maize line, the improved first inbred maize line being derived from crossing a first parent having identifiable first parent chromosomal regions on selected chromosomes, and the second parent having identifiable second parent chromosomal regions on selected chromosomes, the first parent chromosomal regions having a trait conferring resistance to $MDMV_B$ and/or CLN in hybrid combination, and a second parent having an agronomically desirable genotype in hybrid combination, except for the second parent identifiable chromosomal regions on selected chromosomes, the second parent chromosomal regions having a trait conferring relative sensitivity to $MDMV_B$ and/or CLN wherein the improved inbred line derived from the first parent and the second parent has improved inbred line identifiable chromosomal regions on selected chromosomes which are substantially like the first parent chromosomal regions wherein the improved inbred line has the trait of resistance to $MDMV_B$ and/or CLN, in hybrid combination, not significantly less than that of the first parent in the same hybrid combination, and has substantially all of the second parents genotype except for the second parents chromosomal regions having the trait conferring relative sensitivity to $MDMV_B$ and/or CLN. An elite inbred maize plant, having resistance to $MDMV_B$ and/or CLN, comprising: a genome, the genome being entirely of maize origin, which contains a genetic material having resistance to $MDMV_B$ and/or CLN, the genetic material selectively introgressed into the elite inbred line, the selectively introgressed genetic material having resistance to $MDMV_B$ and/or CLN being identifiable and located in specific chromosomal regions; and genetic material specifying high yield in hybrid combination.

A maize plant having resistance to $MDMV_B$ and/or CLN, the genome of the maize plant comprising: identified introgressed genetic material associated with $MDMV_B$ and/or CLN resistance at chromosomal loci 1, the loci being defined as being on chromosome one approximate map unit 78; the map units being defined by a maize chromosome map published for the 1993 Maize Genetics Cooperation Newsletter published March 15, 1993, by Department of Agronomy, University of Missouri, Columbia, Mo.

A plant, which is homozygous at least two of the chromosomal loci. A Zea mays L. plant converted to be resistant to MDMVs in which an ancestor is the corn line designated Pa405. A Zea mays L. inbred line which is homozygous for introgressed genes specifying $MDMV_B$ and/or CLN resistance at the loci. A Zea mays L. hybrid plant having improved resistance to $MDMV_B$ and/or CLN, identifiable at the chromosomal loci, the hybrid being the result of a cross between an inbred maize line and the improved inbred maize line.

A Zea mays L. improved inbred line wherein each inbred plant of the inbred line has germplasm consisting of pollen, plant tissue, anthers, seeds, leaves, plant cells, genomic DNA, roots and stalks. Any progeny derived from the germplasm having identifiable genetic material on chromosomes evidencing $MDMV_B$ and/or CLN resistance. A Zea mays L. hybrid plant, comprising the progeny of a cross between first and second inbred lines, genetic material conferring resistance to $MDMV_B$ and/or CLN being present in the homozygous state in the genome of at least one of the first and second inbred lines such that the genomes of the first and second inbreds together donate to the hybrid a complement of genetic material necessary to confer the resistance to $MDMV_B$ and/or CLN. A method for the production of an inbred maize plant adapted for conferring, in hybrid combination with a suitable second inbred, resistance to $MDMV_B$ and/or CLN, comprising: selecting a first donor parental line possessing the desired $MDMV_B$ and/or CLN resistance; crossing the donor line with a second inbred parental line, high yielding, in hybrid combination, to produce a segregating population; screening the population for a member having at chromosome one genetic material associated with the resistance trait; selecting the member for further crossing and selection; and repeating the procedure until an inbred line is obtained which is homozygous for the resistance trait at the selected chromosome region.

An inbred maize line having an introgressed gene that imparts resistance to $MDMV_B$ and/or CLN located between public map units 45–106 whereby the inbred maize line has a genotype that evidences resistance to $MDMV_B$ and/or CLN.

Additionally, the present invention encompasses the converted inbred lines which were made pursuant to the use of the identified chromosomal regions. These inbred embodiments include the following inbreds: An inbred corn line designated $211_{CLN.1}$; an inbred corn line designated $211_{CLN.2}$; an inbred corn line designated $211_{CLN.3}$; an inbred corn line designated $211_{CLN.4}$; an inbred corn line designated ZS19; an inbred corn line designated $563_{MDMVB.44}$. Likewise the parts of these converted lines are included. Pollen of one of the converted inbred lines, seed or seeds and/or tissue.

A method of producing a corn plant comprising: crossing a first parent corn plant with a second parent corn plant wherein one of the first and second parent corn plant is a converted inbred corn plant.

The method wherein the first and second parent corn plants are both converted corn plants. A first generation ($F_1$) hybrid corn plant produced by crossing a first inbred female corn plant with a second inbred male corn plant, wherein the first or second parent corn plant is the converted inbred corn plant. The hybrid corn plant wherein the converted inbred corn plant is the female parent. The hybrid corn plant wherein the converted inbred corn plant is the male parent. A method for producing first generation ($F_1$) hybrid corn seed comprising crossing a first inbred parent corn plant with a second inbred parent corn plant, wherein the first or second parent corn plant is the converted inbred corn plant to produce first generation ($F_1$) hybrid corn seed. A first generation ($F_1$) hybrid corn plant produced by growing the hybrid corn seed.

BRIEF DESCRIPTION OF THE DRAWINGS

FIGS. 1A, 1B, 1C, 1D is a table of data developed for each probe site denoting the average of the mean of the two ratings (MAMR) and the mean of each individual rating (FAMR and SAMR) for each genotype of the progeny of a resistant Pa405 by susceptible 211 cross.

FIGS. 3A-1, 3A-2, 3A-3, 3A-4, 3B-1, 3B-2, 3B-3, 3B-4, 3C-1, 3C-2, 3C-3, 3C-4, 3D-1, 3D-2, 3D-3, 3D-4, 3E-1, 3E-2, 3E-3, 3E-4, 3F-1, 3F-2, 3F-4, 3G-1, 3G-2, 3G-3, 3G-4, 3H-1, 3H-2, 3H-3, 3H-4, 3I-1, 3I-2, 3I-3, 3I-4, 3J-1, 3J-2, 3J-3, 3J-4 is a map portion listing probes for chromosome one of the maize plant. The section of the map shown is from the map published by the 1993 Maize Genetics Cooperation NewsLetter published Mar. 15, 1993, by Department of Agronomy and U.S. Department of Agriculture, University of Missouri, Columbia, Mo.

FIG. 4 is a map portion showing the relevant probes for each chromosomal region associated with the $MDMV_B$ resistance.

FIG. 5 is a table of data from the improved inbred lines in test crosses prior to fixing all the alleles indicating the improved CLN resistance of the tester hybrids, relative to commercial hybrids and relative to the hybrid produced by crossing the unimproved inbreds to each other.

DETAILED DESCRIPTION OF THE EMBODIMENTS

Figures 1, 3A:
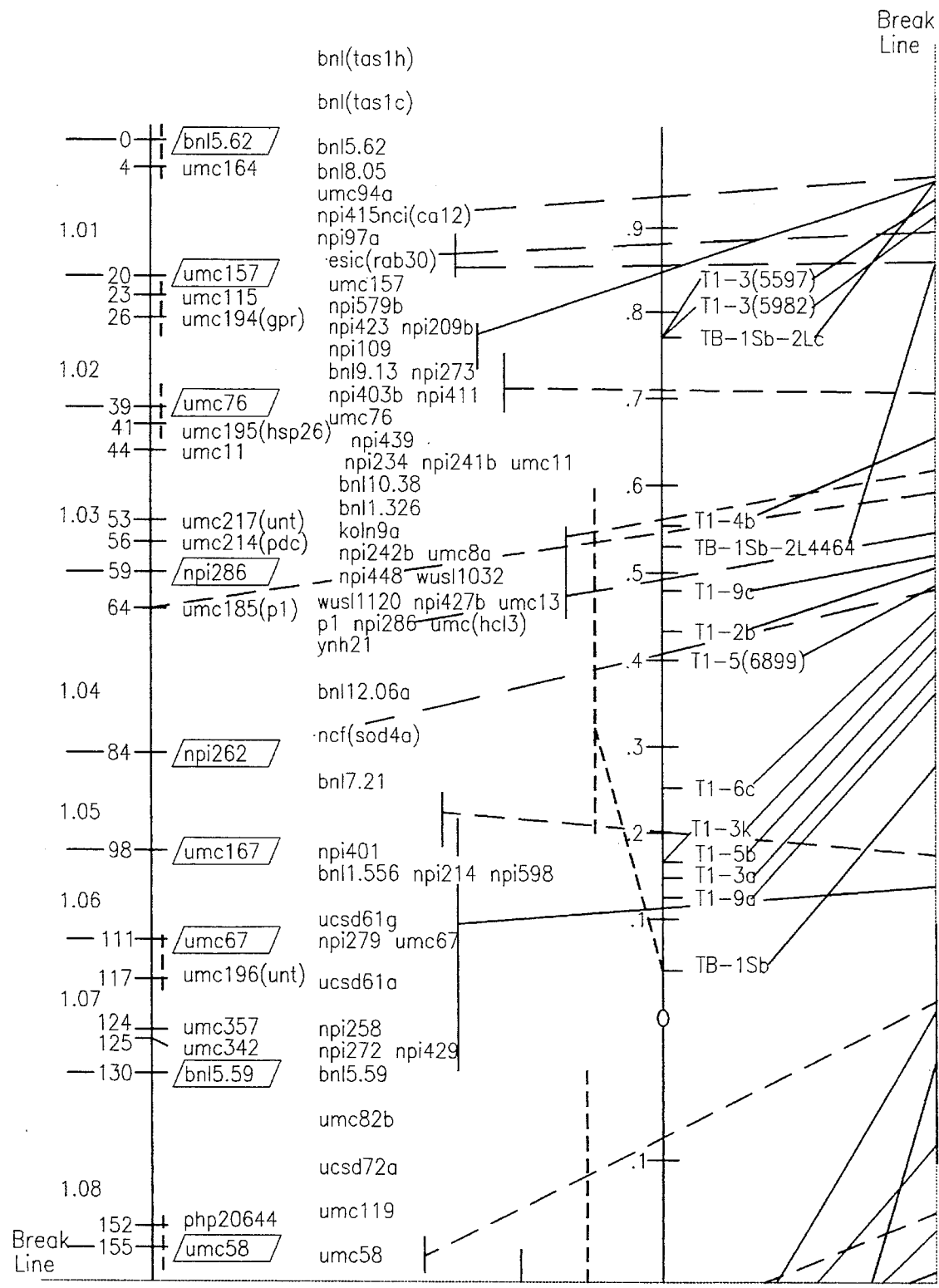

Broadly this invention relates to a maize plant and a method of producing same, which is resistant to CLN. More specifically, the present invention relates to a maize plant and a method of producing the same which is resistant to Maize Dwarf Mosaic Virus strain B. This invention relates to introgression in maize of genetic material (for the first time identified) capable of causing the plant to be resistant to $MDMV_B$. Additionally the present invention relates to a method of introgression of the desired genetic material from one or more parent plants into the progeny with precision and accuracy. It will be appreciated that the $MDMW_B$ converted line offers a much improved donor for use in pedigree or backcross breeding programs because recombination of genes for yield and other desirable agronomic traits and $CLN/MDMV_B$ resistance has already been accomplished by the present invention.

To assist in the description of this invention the following glossary of terms are provided.

Converted

Plant—any plant having resistance to MDMVs and/or CLN and additionally the plant or an ancestor of the plant having been selected by reference to RFLP data for the locus 1 or locus 3 regions.

Crossover—shall mean an exchange of segments of homologous chromosomes during meiosis whereby linked genes become recombined; also the product of such an exchange. The cross-over frequency is the proportion of gametes bearing a cross-over between two specific gene loci.

It ranges from 0 for allelic genes to 50% for genes so far apart that there is always a cross-over between them. The cross-over site is the place in the chromosome where breakage and reunion of DNA strands occur during recombination.

Introgression—shall mean the condition in which a linkage block has been brought into or introduced into a plant from another plant.

Introgressing—shall mean entering or introducing a gene or a linkage block from one plant into another.

Linkage Block—shall mean an identified chromosomal region containing genetic material that expresses a desired trait.

Recombination—shall mean reassortment of genes or characters in combinations different from what they were in the parents, such as cross-overs or linked genes.

The method of the invention comprises the use of molecular markers to select progeny plants from a cross of a CLN/MDMV$_B$ resistant donor to high yielding, susceptible recipients to develop progeny which contain all or most of the preferred alleles for resistance to CLN/MDMV$_B$ and agronomically desirable traits. It is not necessary (or often not desirable on efficiency grounds) to find the complete complement amongst the progeny of a single cross. Rather, it is possible to select by RFLP and/or disease screens individual progeny plants exhibiting a proportion of the desired recombinations and to further cross such individuals or backcross such individuals in order to create the desired genome progressively.

The donor parent, a publicly available line, is designated Pa405. The donor parent could be Pa405's progenitors or resistant progeny. However, using the present invention other donor parents can be readily identified. The loci 1–3 (described below) are detectable by RFLP or equivalent molecular marker analysis.

Pa405 has been publicly available for some time. Pa405 is resistant to MDMV$_B$. In spite of this, there is still a need for MDMV$_B$ inbreds, principally because Pa405 is not germplasm material which can be crossed with a second inbred and form a commercially acceptable viable hybrid (under 1994 corn industry standards), i.e. a hybrid with desirable agronomic traits. In contrast, the present invention has the entire yield/agronomic/virus package and includes a method of using modern breeding techniques in combination with the present invention to move the desirable genetic material from elite backgrounds to other elite backgrounds or from germplasm source material to elite backgrounds, etc.

The present invention was developed in two stages. The first stage was the location of the chromosomal regions containing genes that characterize the plant as expressing resistance to CLN/MDMV$_B$. The second stage was the introgression of the identified chromosomal regions into genotypes that have agronomically desirable traits thus forming resultant progeny having CLN/MDMV$_B$ resistance and agronomically desirable traits which can produce a commercially viable hybrid under 1994 industry standards.

The first stage required two things: a plant or plants that have the desired trait, in this case, expression of resistance to MDMV$_B$, and an accurate and reliable screening procedure to determine whether progeny of the CLN/MDMV$_B$ plants have the desired trait.

Pa405 expresses resistance to CLN/MDMV$_B$. To locate the chromosomal regions associated with the resistance to CLN/MDMV$_B$, the resistant plant, Pa405, was crossed to a susceptible inbred designated 211. The seed from the F$_1$ population was planted to form the segregating F$_2$ population. The F$_2$ population was screened by the following procedure to identify the degree of resistance shown in the plant to CLN/MDMV$_B$.

The plants were screened for MCMV$_B$. A CLN screen was done on hybrid test crosses which will be described later in reference to FIG. 5. The MDMV$_B$ screen was a two step procedure. The first step was inoculation of the plants. The second step was assessing the severity of the infection of the plants. The inoculation was a multiple inoculation procedure. Three inoculations at one week intervals were performed. The first inoculation was given at the two to three leaf stage. The inoculum for MDMV$_B$ was made of 167 grams of symptomatic leaves in one liter of H$_2$O. The leaves were ground and the solution was strained through cheese cloth, The resultant strained liquid was reconstituted with H$_2$O to one liter. Fifteen grams of Celite™ (commercially available from Fischer) diatomous earth was added. The inoculum was then placed in a pressurized paint sprayer. The application of inoculum was a two second blast providing 0.5 ml to 0.75 ml inoculum in the whorl of the individual plants.

The second step of this screening procedure is the disease severity assessment of the MDMV$_B$ infected corn plants. This assessment was based on visual readings of the amount of mosaic symptoms on a 5 to 1 scale during two separate assessment periods; 5 equaled no symptoms and was based on the amount of mosaic symptoms shown by Pa405 and 1 equaled severe symptoms and was based on the symptoms visible on the susceptible inbred. The symptoms were rated on a sliding scale by the amount of mosaic present on the plant. The plants were assessed once at eight weeks after planting. This assessment is referred to as (FAMR) in the tables. The second plant assessment was done at ten weeks after planting. The second assessment is designated (SAMR). The results of the mean of the two assessments were averaged to give the (MAMR). The response or resistance of the plants ranged from symptomless to severe. Symptomless was a rating of 5. A resistance score of 5 is defined as extremely resistant. Non-resistant was any score below the 5 score; the scores in the non-resistant range, such as between 1–2.9, were classified as severely susceptible.

This screening procedure allowed the identification of the extreme tails of the F$_2$ populations. In other words, plants which were extremely susceptible and plants which were extremely resistant to MDMV$_B$, and therefore to CLN, were identified.

Identification of the chromosomal regions associated with MDMV$_B$ were located by the comparisons of the RFLP data of the susceptible and resistant plants with the assessment data of these plants. Approximately 150–200 plants were used to generate the data shown in FIG. 1. The RFLP data shown in FIGS. 1 and 2 were generated by the following RFLP protocol:

A. DNA Extraction

The corn plant tissue was lyophilized, ground to a fine powder in a mill and the DNA was extracted. 100 ml of RNase (10 mg/ml) were placed in tubes and the supernate was filtered and placed in the tubes and incubated. The DNA precipitate was snagged, transferred to a culture containing 76% ETOH/10 mM NH$_4$Ac, and incubated. See Proc. Natl. Acc. Sci. USA 81:8014–8018

B. DNA Digestion

The DNA was quantified fluorimetrically, and digested to completion. DNA was loaded onto slab gel and electrophoresised. DNA was transferred onto Hybor-N+membrane (Amersham) via southern blotting. The protocol is as suggested by the Manufacturer.

C. Southern Blotting

A matrix of Hybond N+ Nucleic Acid transfer membrane, was soaked in 25 mM $NaH_2PO_4$ at −pH 6.5. The blots were baked for two hours. The Southern Blot procedure is well known in the art at J. Mol. Biol. 98:503 (1975).

D. Oligo Reaction 40 ng DNA was mixed with sufficient $H_2O$ to make up 3/ml of solution. The DNA was denatured for ten minutes at 95° C. and then 10 ml oligo buffer, 2 ml BSA, 5 ml 32P-dctp, 2 ml Klenow was added. These solutions are commercially available from Ceres and were mixed per manufacturer's instructions. The sample was incubated and then a 150 ml stop buffer was added. This protocol is published in Feinberg, A. P., B. Volgelstein, Anal. Biochem. 132:6, 1983.

E. Probe Hybridization

Probe fragments were generated from recombinant plasmids using PCR and the products gel-purified prior to labelling with 32p-ctp (Amersham) via random priming. The blots were decanted and placed on Kodak XAR X-ray film and exposed. The procedure used is published in B. Buddowle, et.al. Crime Laboratory Digest 15:3–21, 1988.

F. Probe Removal

The blots were washed in 5 mM Tris-HCL/pH 8.0, 0.2 mM EDTA 0.05% pyrophosphate, 0.1x Denhart's for 1–2 hours at 65°–75° C. Denhart's Solution—50x is formed as follows: Ficol—5 g, polyvinzlpyorolidone—5 g, BSA (Pentax Fraction V)—5 g, $H_2O$—500 ml. Then rinsed in 1xSSPE. SSPE (2xx) is formed as follows: 174 g NaCl, 27.6 g $NaH_2PO_4$ $H_2$), 7.4 g EDTA, 800 ml $H_2O$, adjust pH 7.4, bring volume to 1 liter.

This procedure was employed to generate most of the data shown in the attached figures. The plant source of the genetic material associated with the listed probes is indicated in FIGS. 1. FIGS. 1 shows the number of plant (N) classified by RFLP genotype as having received alleles from the susceptible parent (SS), the resistant parent (RR) and plants (RS) having material evidencing derivation from both parents. Based on the genotype classification as RR, SS, or RS at each probe location, the data for the ratings of the first time (FAMR) and the data for second set of ratings (SAMR) were analyzed and the mean of these was calculated. The average of the two means (FAMR) and (SAMR) was also calculated giving (MAMR). These data were used to identify polymorphisms that had relevance to resistance for CLN and specifically to $MDMV_B$.

The probes are listed in the FIGS. 1 by their first letter and their number, i.e. probe on BNL5.62 (as listed on FIG. 3) would be listed on FIG. 1 as BO562. On chromosome three the probe B0537 had MAMR for the SS class equal to 3.58 and for RR 4.51, a difference of 0.93. A difference of nearly a full rating point, as seen for BNL5.37, corresponds to a large difference in observable symptoms, and is shown to be statistically significant in FIG. 2. The N0247 probe on chromosome three also evidences a significant difference between RR at 4.51 and SS at 3.51. The probe N0296, which is located relatively near B0537 and N0247, likewise showed SS mean of 3.32 and RR mean of 4.53. Probe N0296AD also indicated significant differences between RR and SS on chromosome three.

Probes B0833 (BNL8.33 on FIGS. 3) and U0085 (UMC85 on FIG. 3) on chromosomes five and six, respectively, indicated significant differences in the RR and SS genotypes. B0833 has mean rating for SS of 4.41 and RR of 3.72. U0085 has average for SS of 3.17 and a RR of 4.72 indicating that this region of chromosome six is associated with resistance to $MDMV_B$. This finding was surprising. This region of chromosome six is associated with $MDMV_A$ and yet $MDMV_A$ resistant corn is still susceptible to $MDMV_B$ and CLN. This indicates that the region on chromosome six alone is not sufficient for $MDMV_B$/CLN resistance and the region on chromosome three is required also to give the full package of $MDMV_B$ resistance.

Figures 2, 3A:
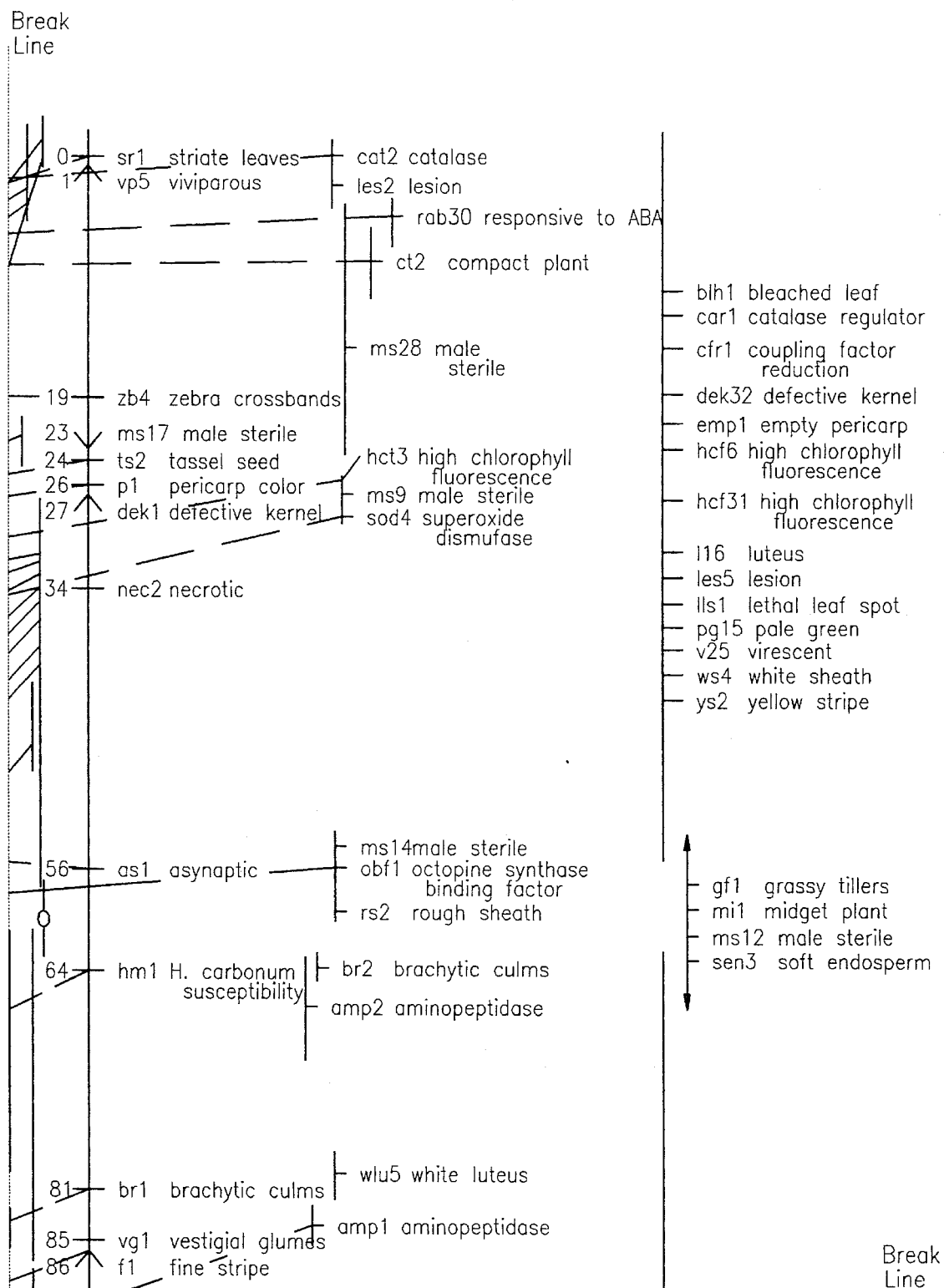

The results of the RFLP analysis are more specifically shown as a statistical analysis in FIG. 2, and indicate that regions of chromosomes three and six of Pa405 and chromosome five on 211 carried the genetic material responsible for resistance to $MDMV_B$. The data gathered indicated the susceptible parent 211 had some genetic material that contributed to resistance to $MDMV_B$. This genetic material did not provide a major expression of the resistance, however. The negative sign indicates the chromosomal five resistance derives from the susceptible plants. This chromosomal material is centered proximate B0833 probe.

FIG. 2 shows how the data in FIGS. 1 were statistically evaluated to determine which probes mark genetic regions or linkage blocks associated with the CLN resistance specifically by location of resistance to $MDMV_B$. (Since CLN is a disease complex which requires two viruses to infect the plant, resistance to CLN can be accomplished by providing resistance to one of the two viruses necessary to generate CLN. In this case the resistance sought was to $MDMV_B$. The result was the absence of CLN symptoms when CLN inoculum was used.) The terms in this figure are explained below:

The resistant=Pa405 and the susceptible=211.

Significance level scores

No score=not significant at the 0.5 level

5=significant at the 0.5 level

1=significant at the 0.01 level

0=significant at a level lower than 0.01

(RSQ)=R squared=estimated proportion of total variance associated with that probe, based on difference between average rated symptoms of the homozygous resistant and homozygous susceptible allele class.

PR>F=probability of chance occurrence.

FALC A=estimate of the average effect of an allele substitution Falconer's 'a'.

FIG. 2 shows probes located in the sections of the maize chromosomes of interest. The donor parent Pa405 carries significantly detrimental agronomic characteristics. Thus it was necessary to identify the chromosomal region of interest as closely as possible so that when introgressing one or more of the linkage blocks 1 and 3 into elite germplasm, only the desired resistance to CLN through resistance to $MDMV_B$ is transferred into the genome of the resultant inbred and likewise hybrid combination. Thus to generate a commercially viable inbred, the beginning crossover event (the crossover closest to the distal end of the short arm of the respective chromosome) and the ending crossover event (the crossover closest to the distal end of the long arm of the respective chromosome) must occur with precision and accuracy to avoid carrying excessive genetic material from the donor source into the resultant inbred. Of course if the donor material is elite material and because of this invention has the precise crossover events therein, then the carryover of some of the elite genetic material into the new progeny is not necessarily detrimental. However, to generate the first introgressed plant at loci 1 and 3 the crossover events were critical.

It should be readily understood in the art that other probes which more closely map the linkage blocks could be employed to identify the selected crossover events. The selected linkage blocks listed above (between flanking probes and/or between map regions) are selected to permit the trait to be transferred without the transfer of undesirable traits from the donor of the trait. Larger linkage blocks could likewise be transferred within the scope of this invention as long as the material introgressed is sufficiently tailored to transfer the $MDMV_B$/CLN resistance and to avoid transfer of undesirable traits into the resultant plant. It will be appreciated that breeding efforts which seek to improve agronomic traits while attaining CLN and $MDMV_B$ resistance are empowered by the selection arrangement of the superior alleles in the linkage blocks.

Figures 3, 3A:
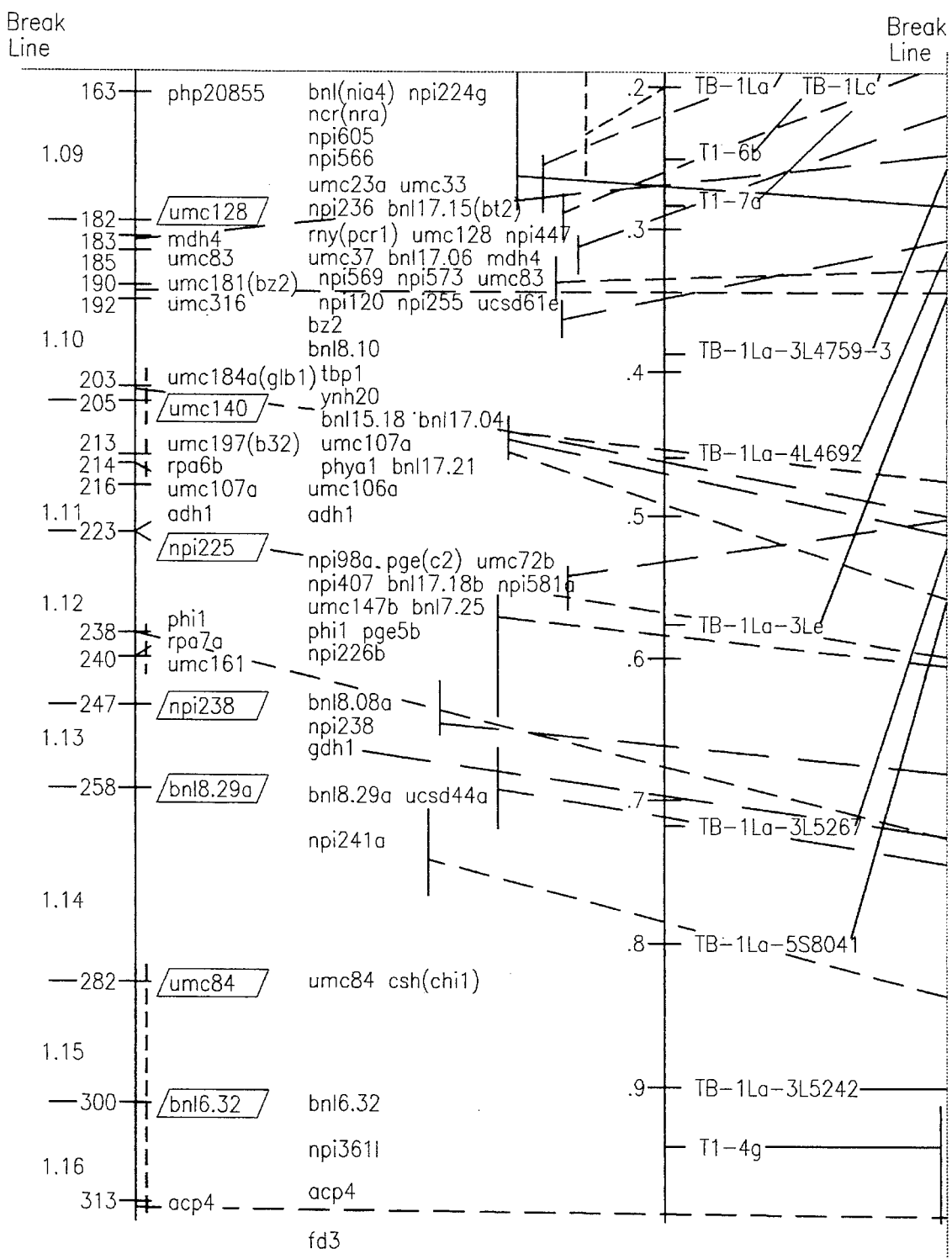
Figures 3, 3A, 4:
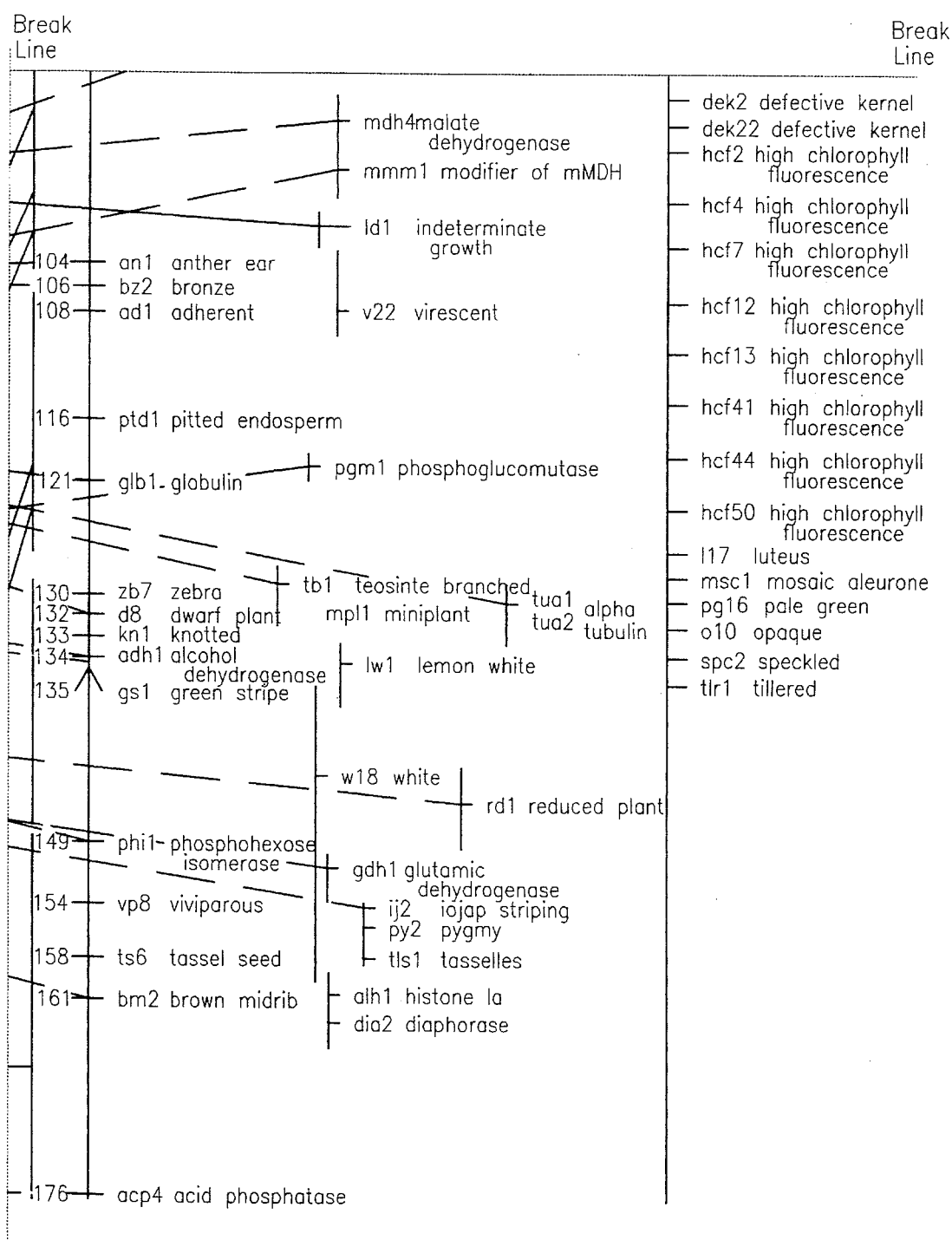
Figures 1, 3B:
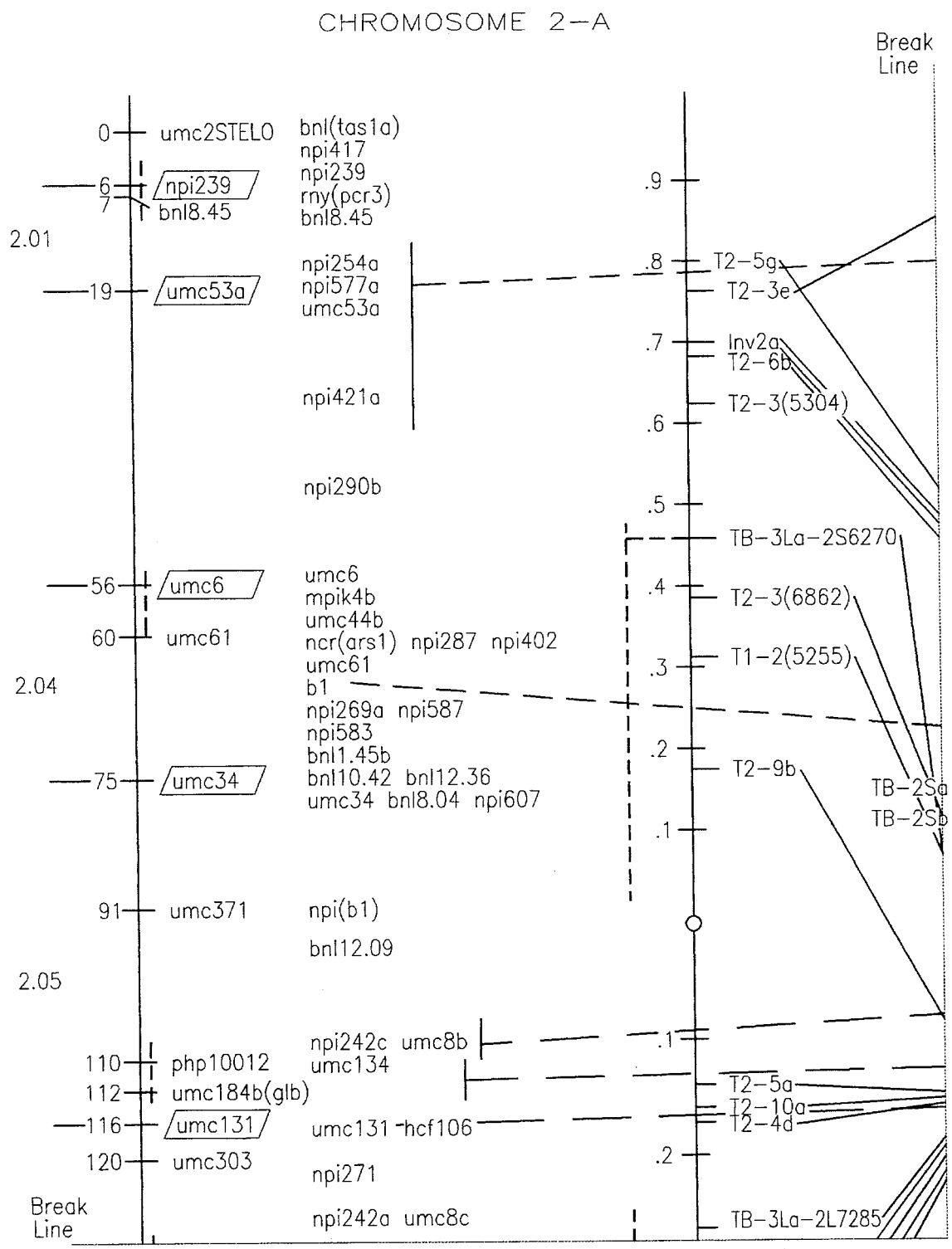
Figures 2, 3B:
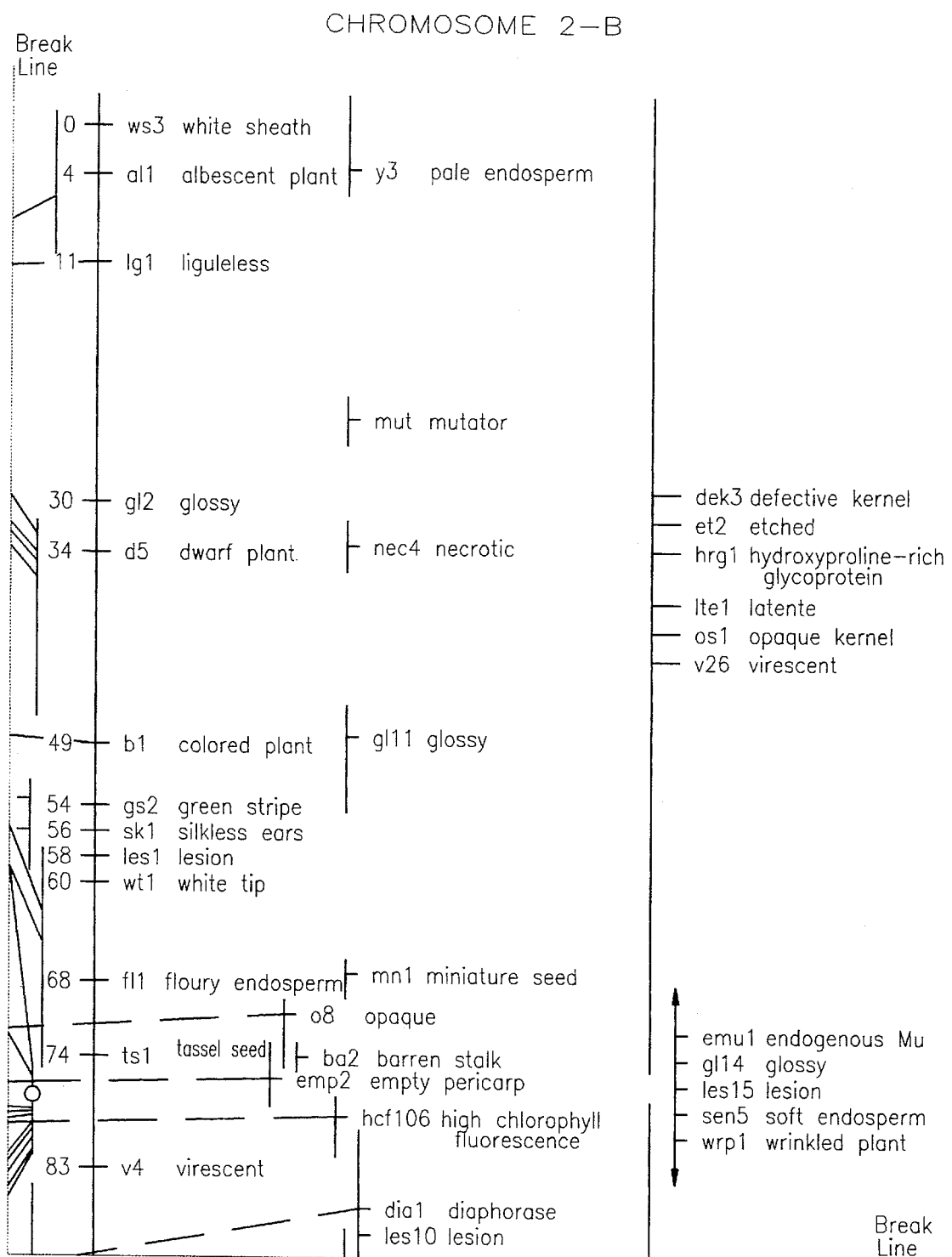
Figures 3, 3B:
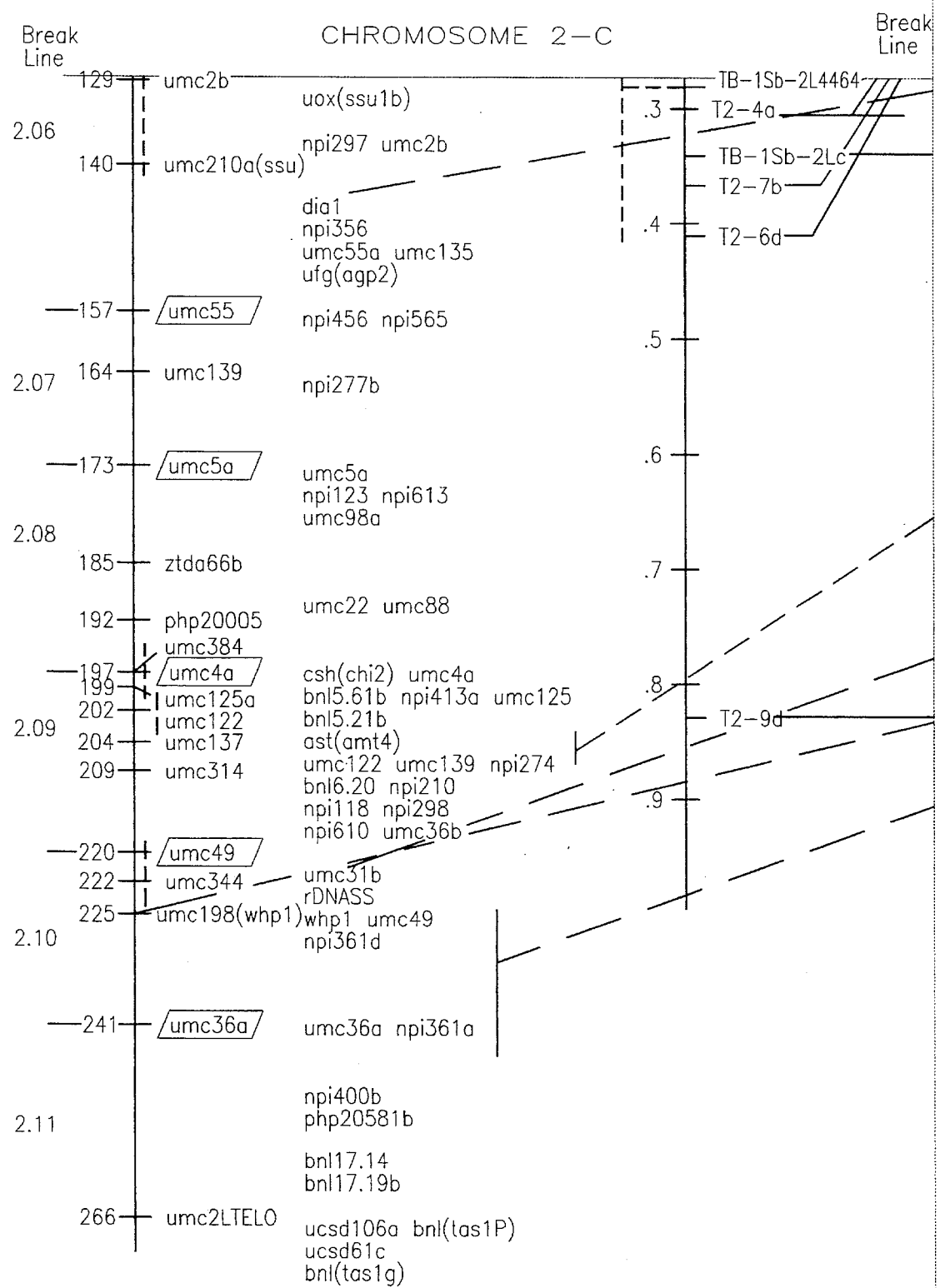
Figures 3, 3B, 4:
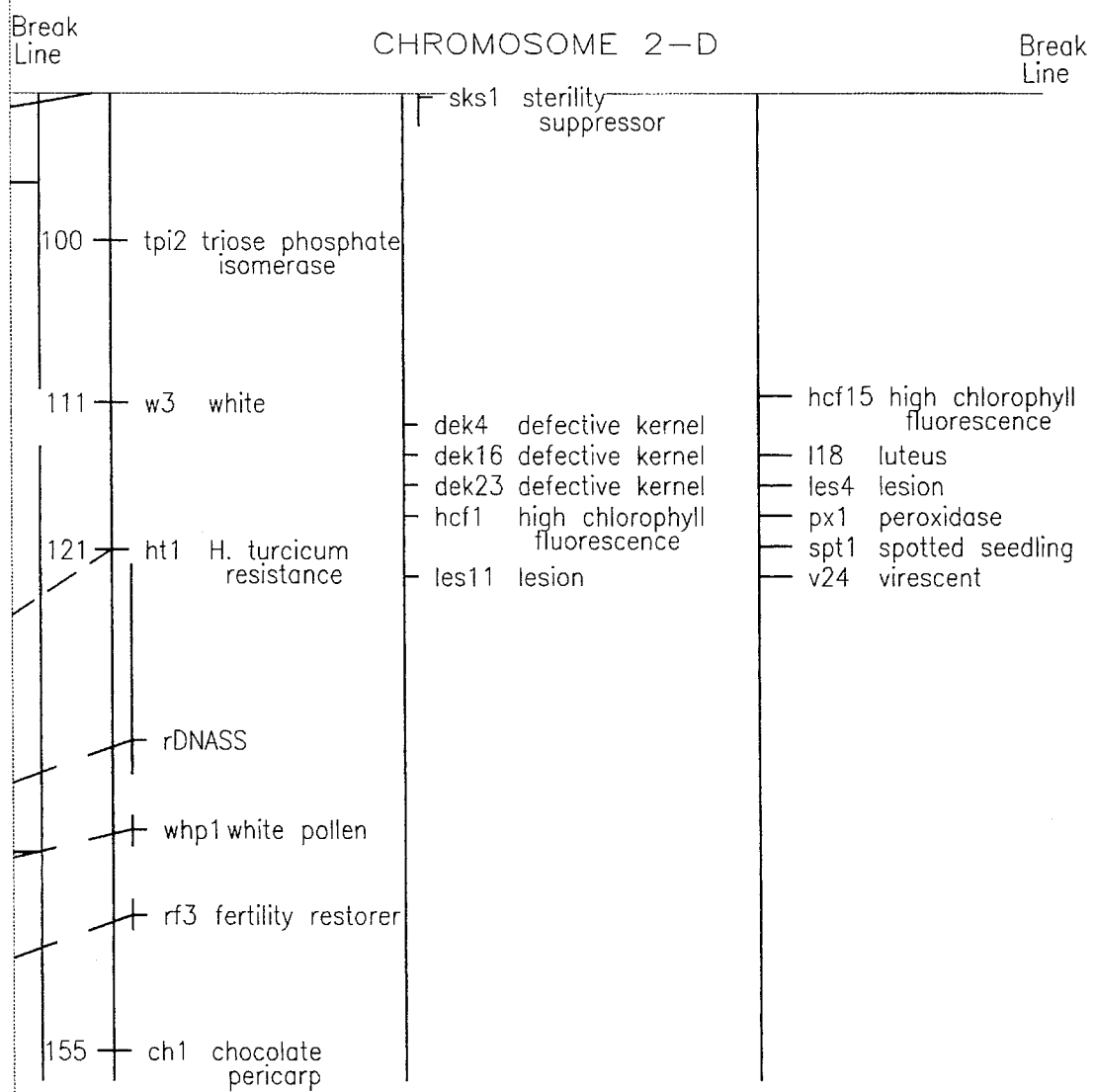
Figures 1, 3C:
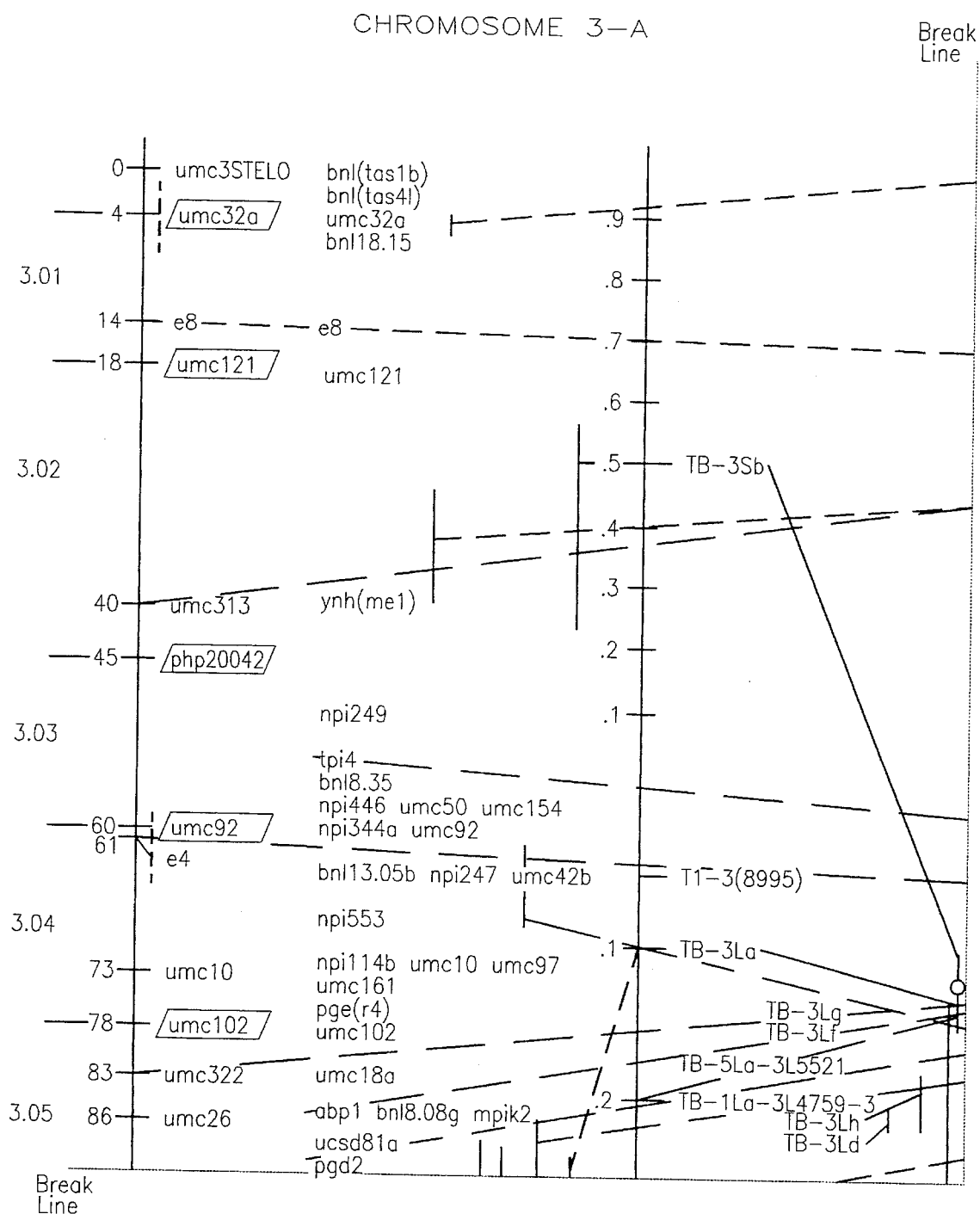
Figures 2, 3C:
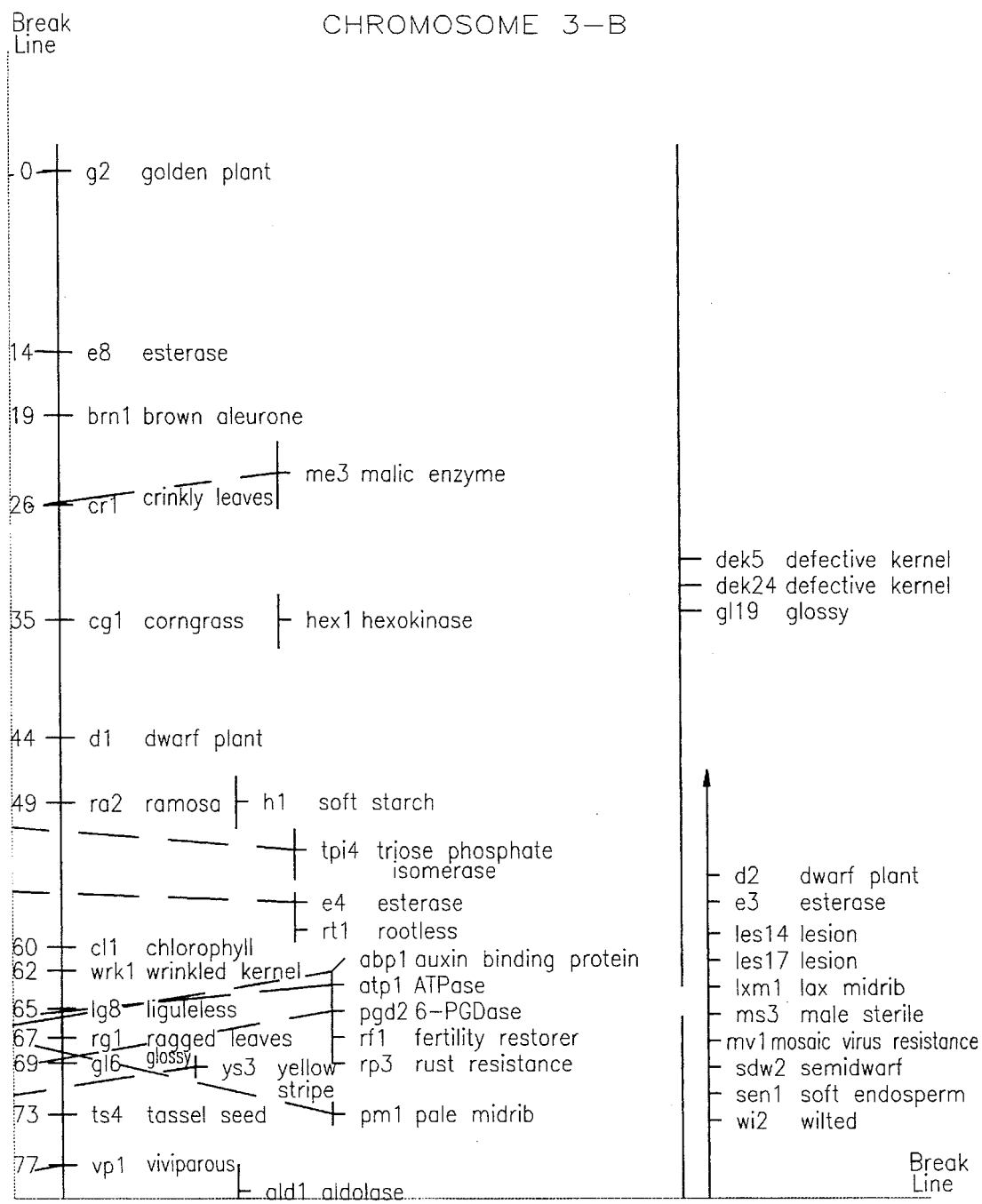
Figures 3, 3C:
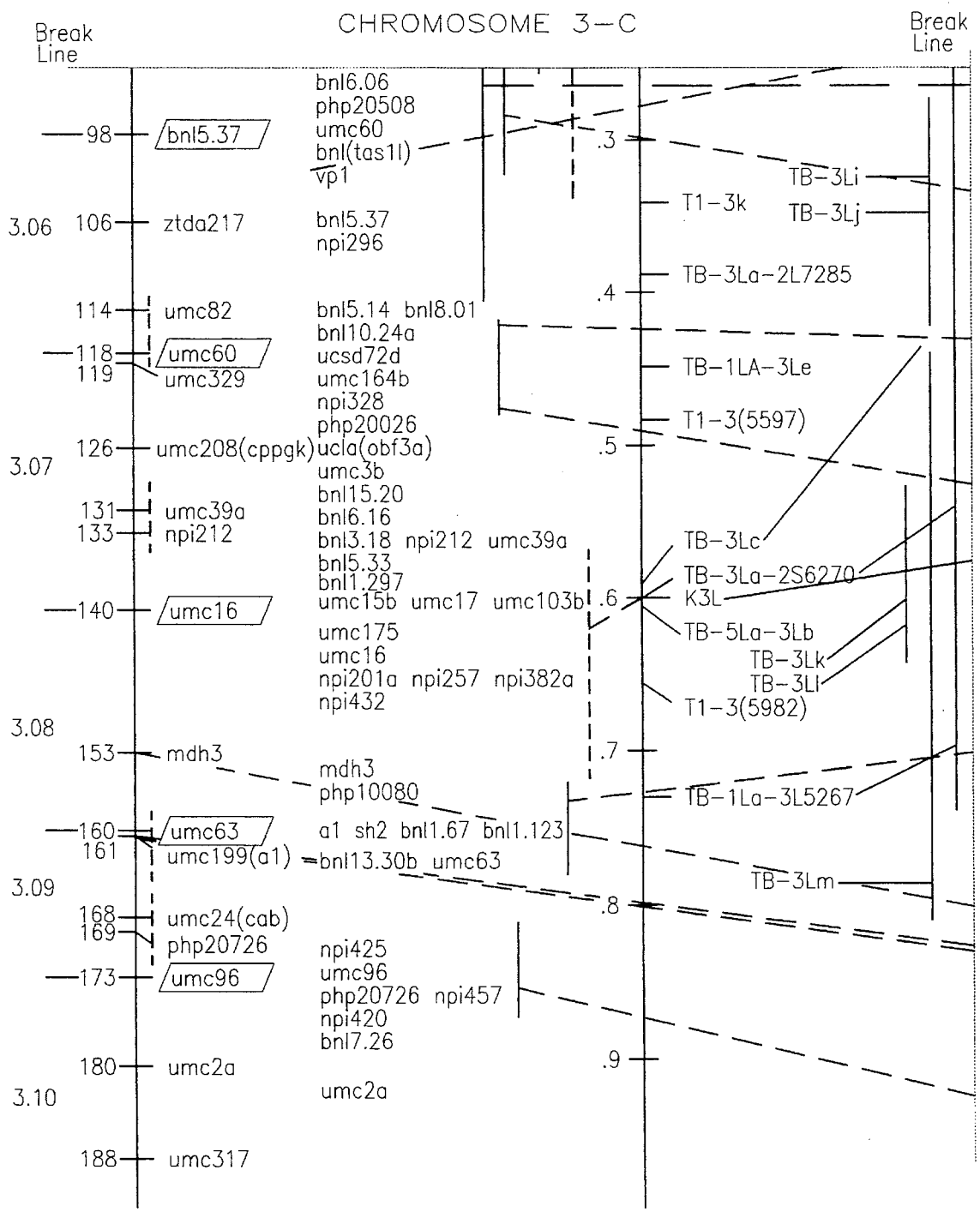
Figures 3, 3C, 4:
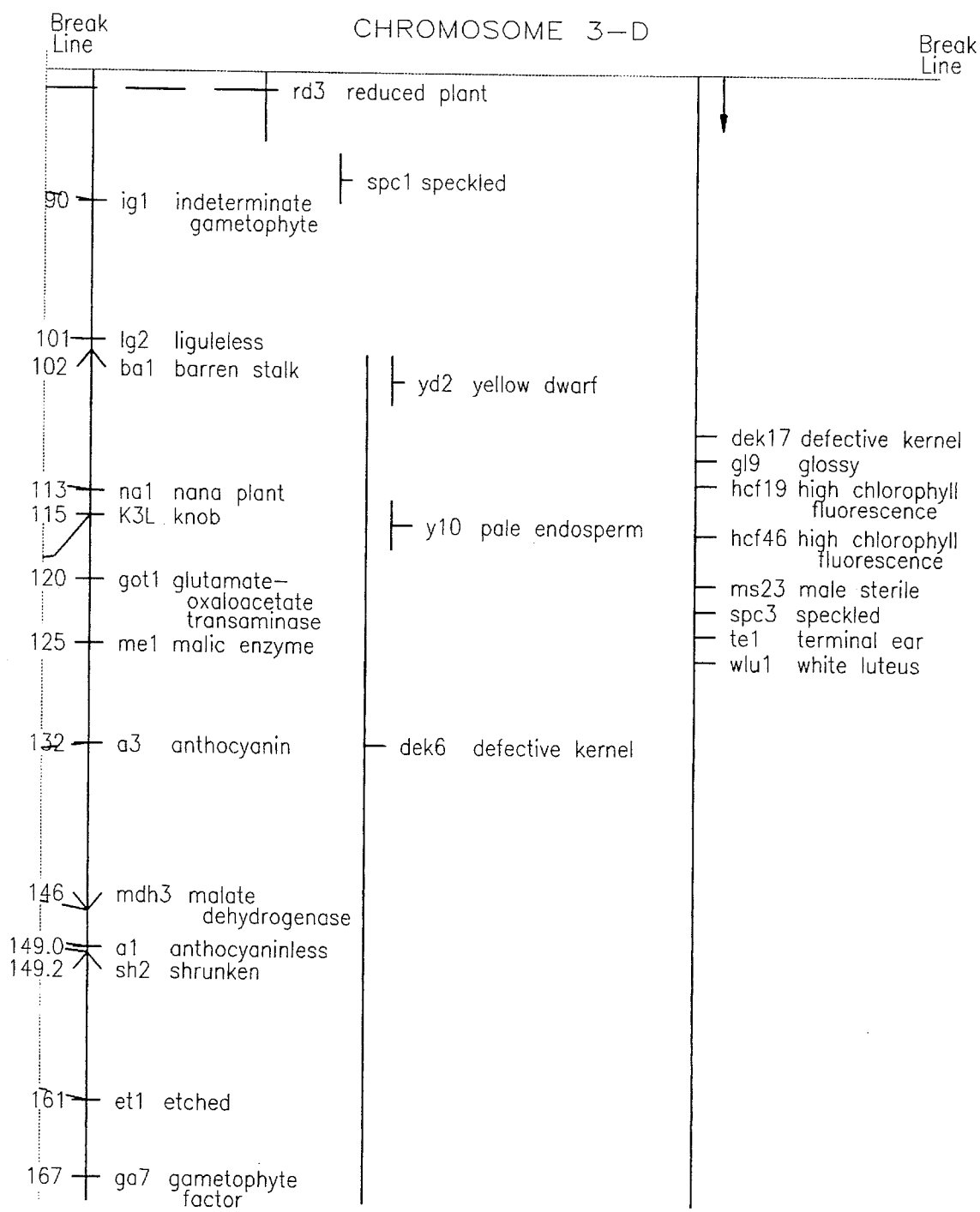
Figures 1, 3D:
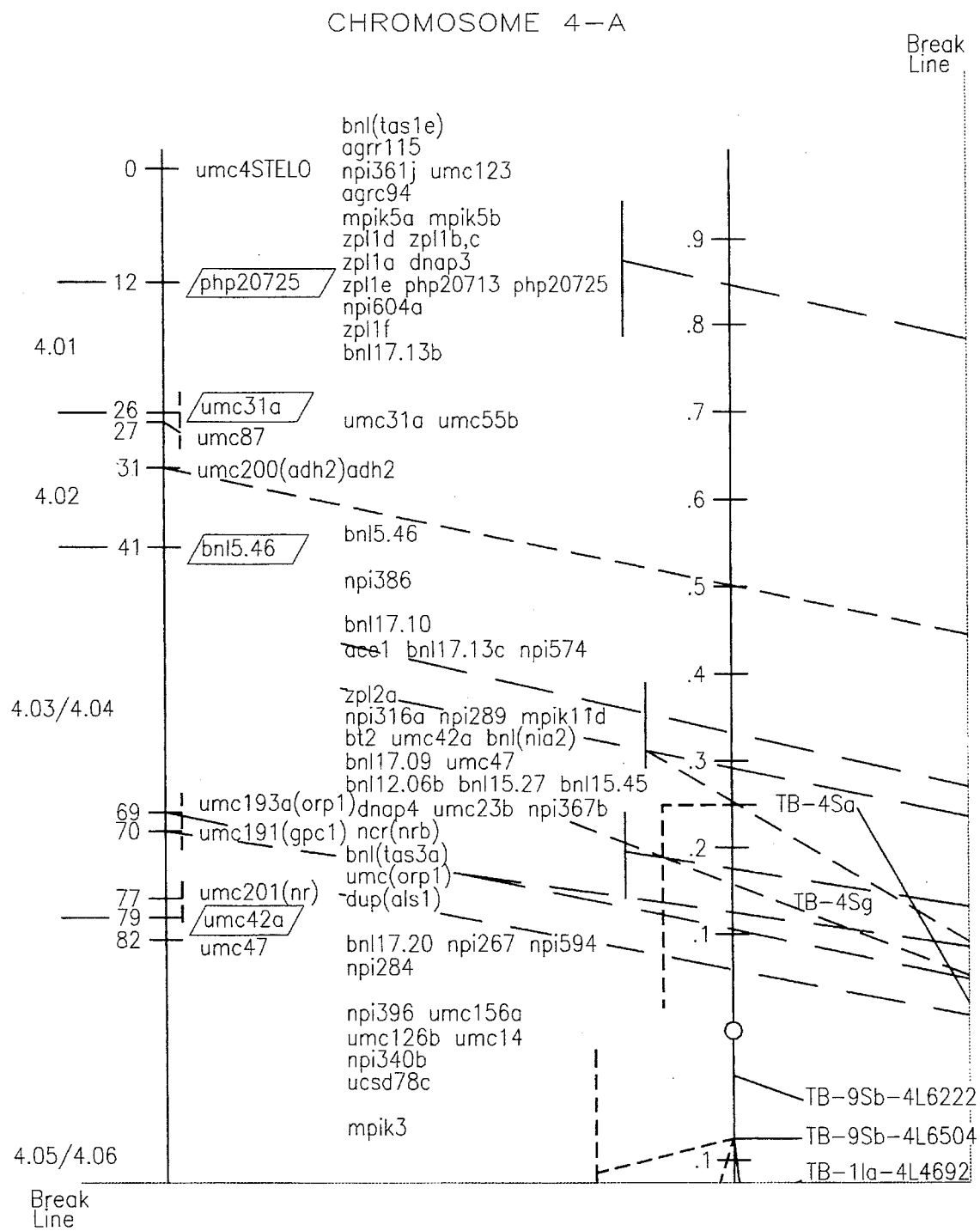
Figures 2, 3D:
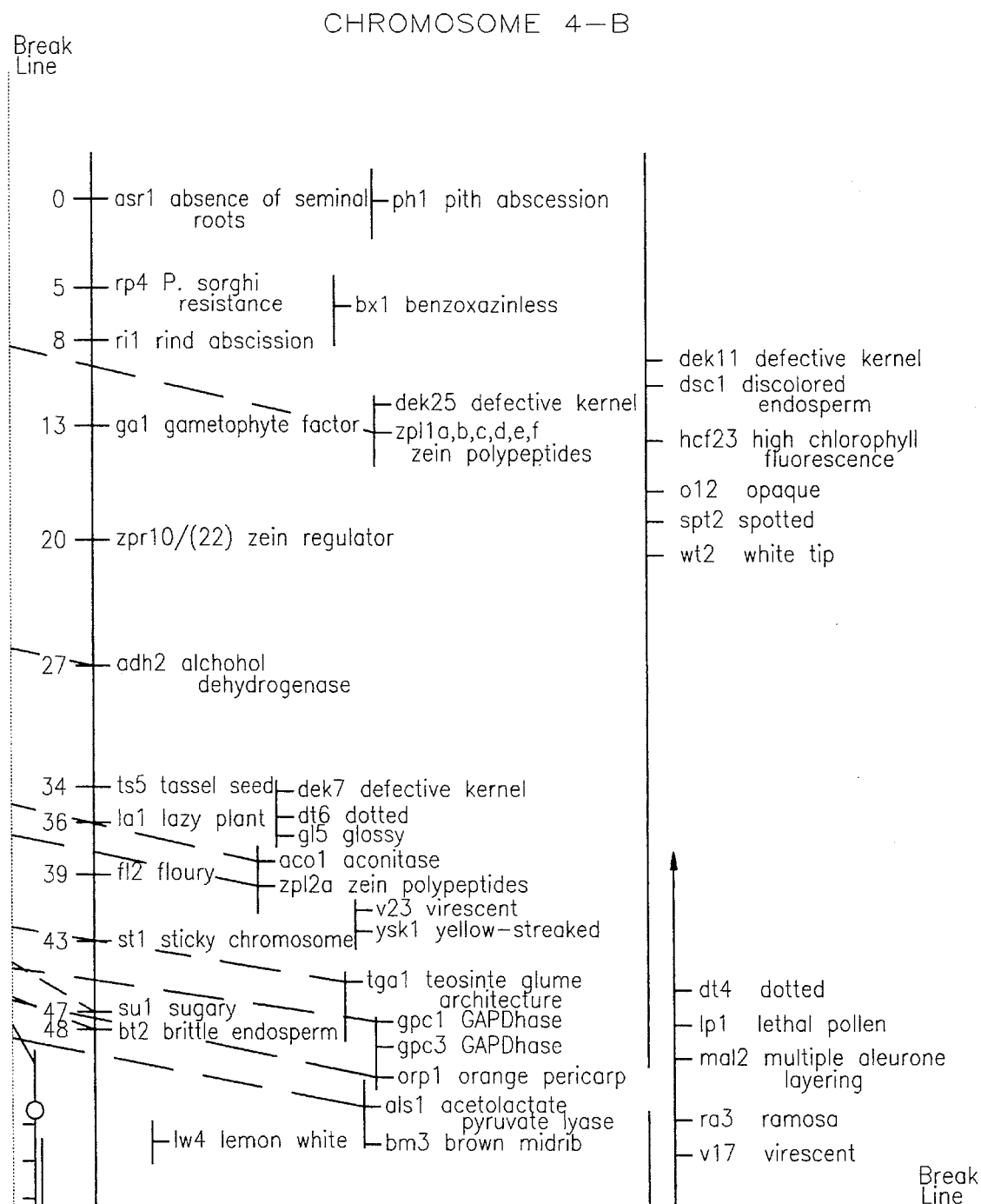
Figures 3, 3D:
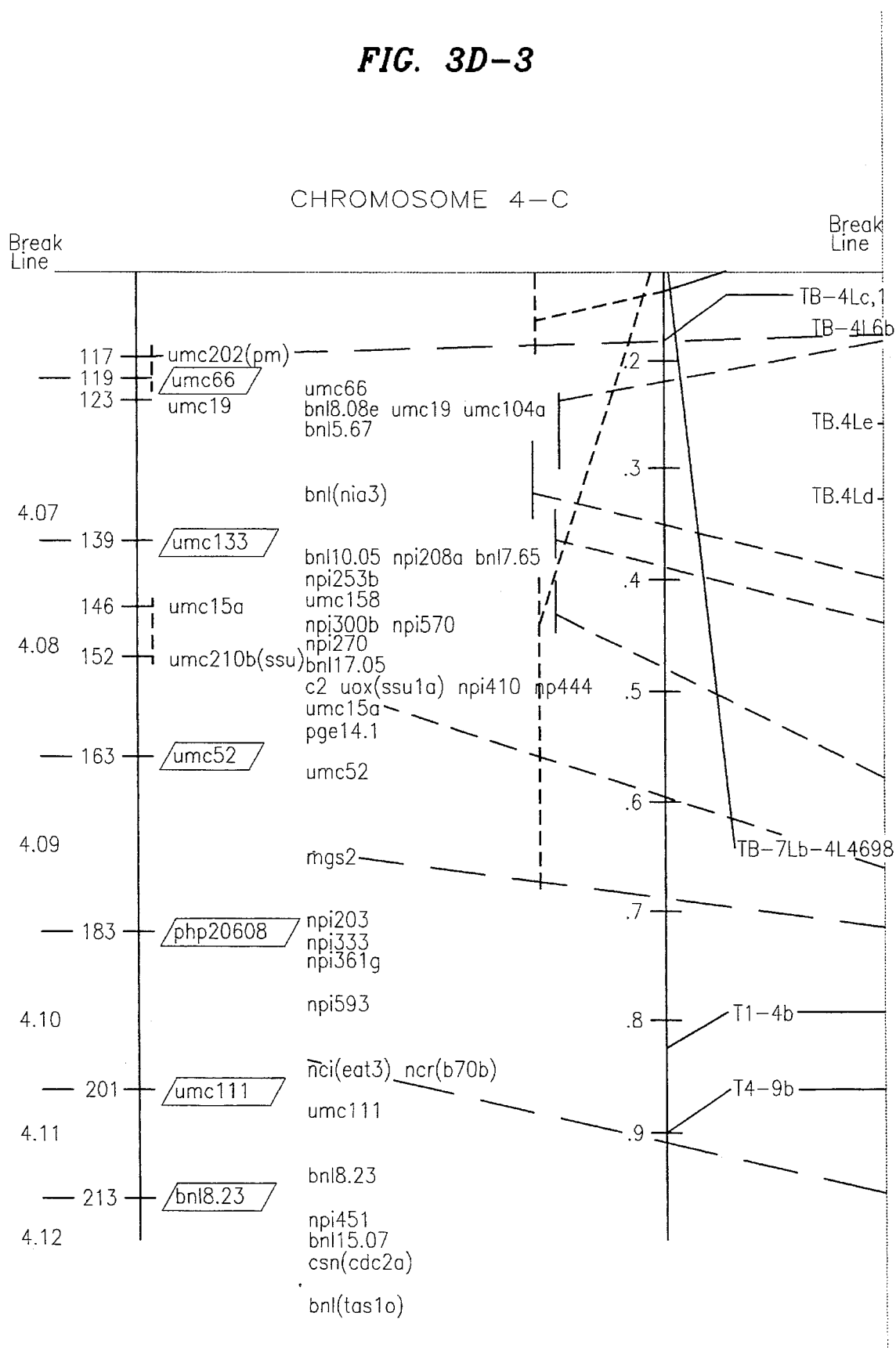
Figures 3, 3D, 4:
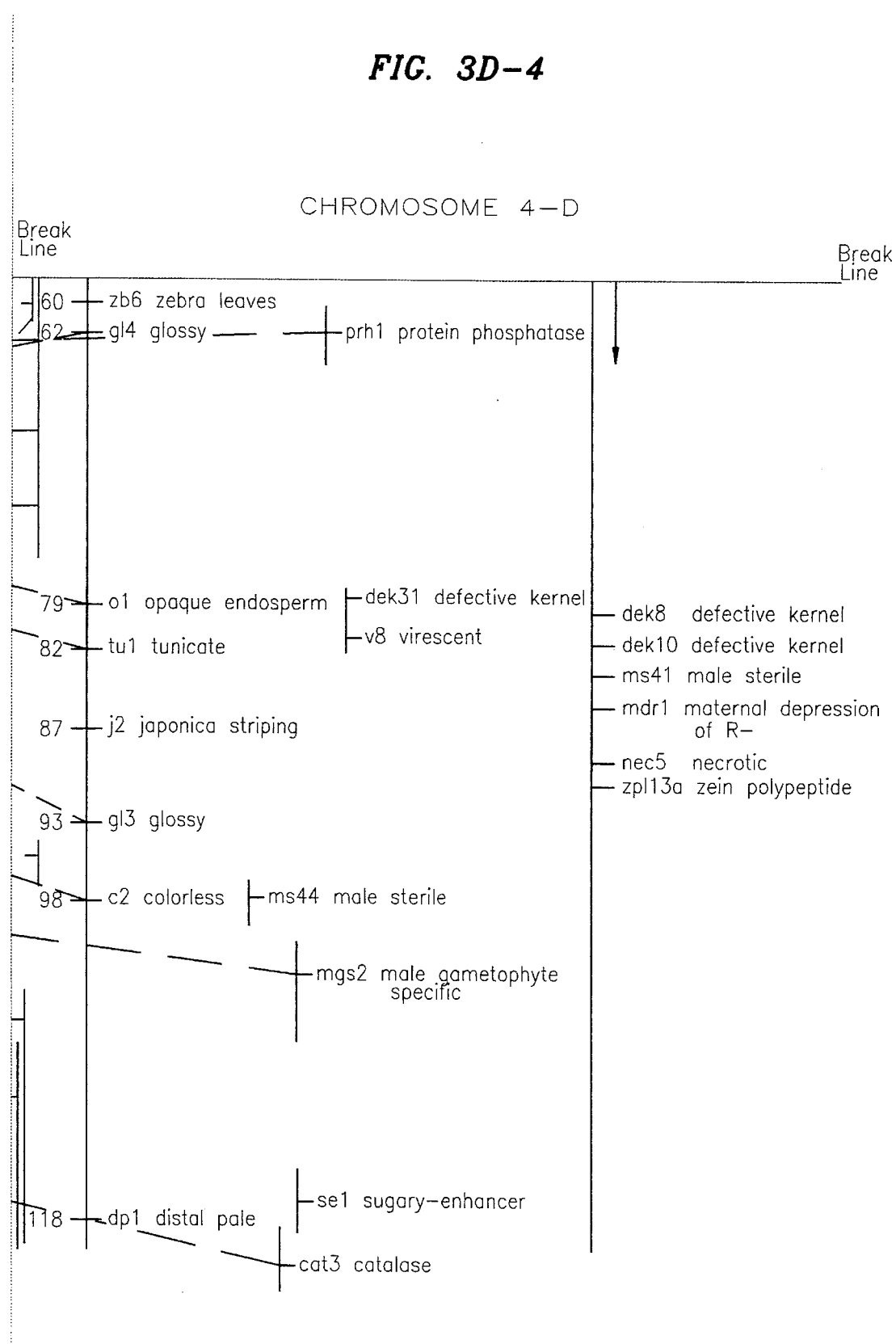
Figures 1, 3E:
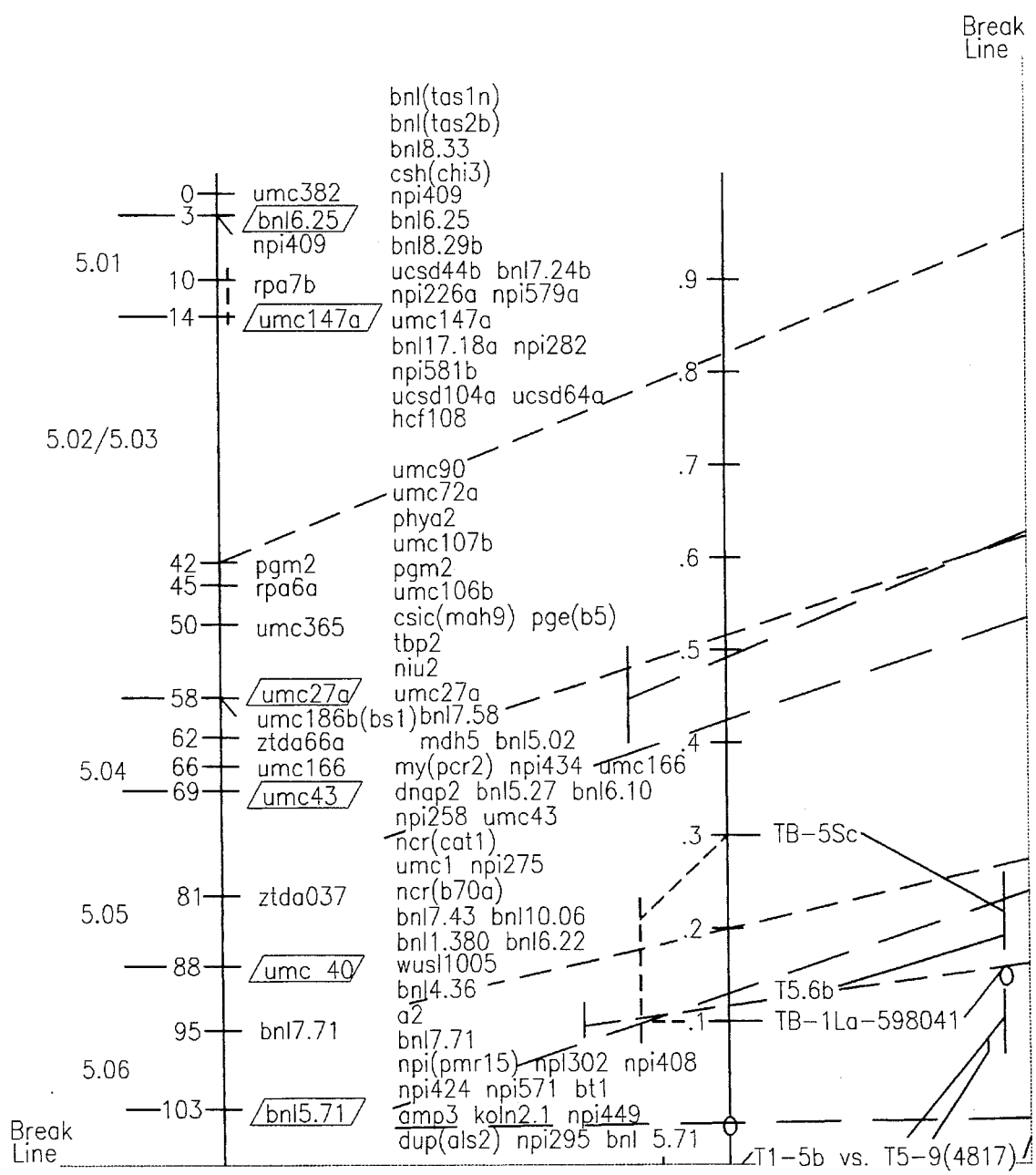
Figures 2, 3E:
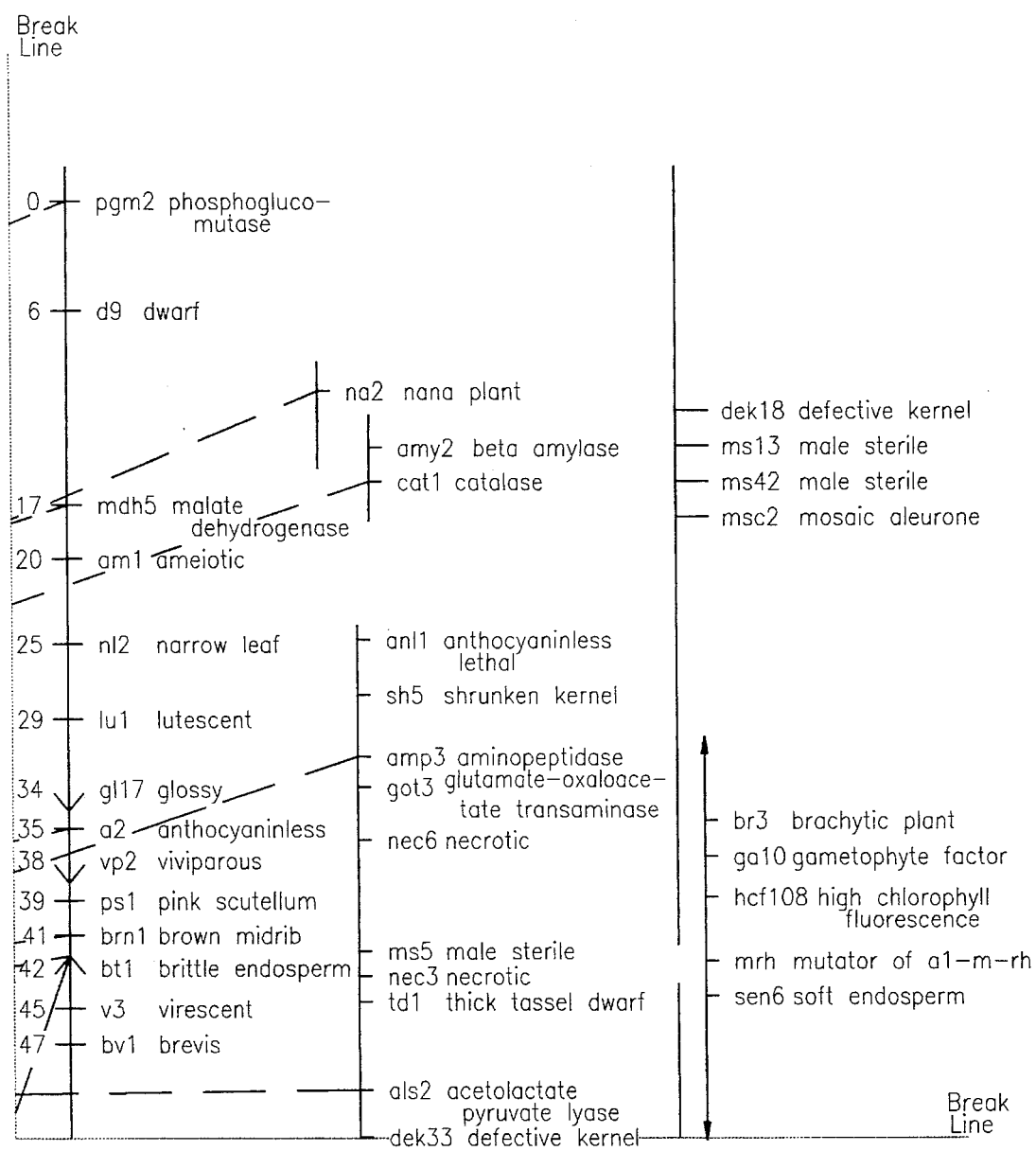
Figures 3, 3E:
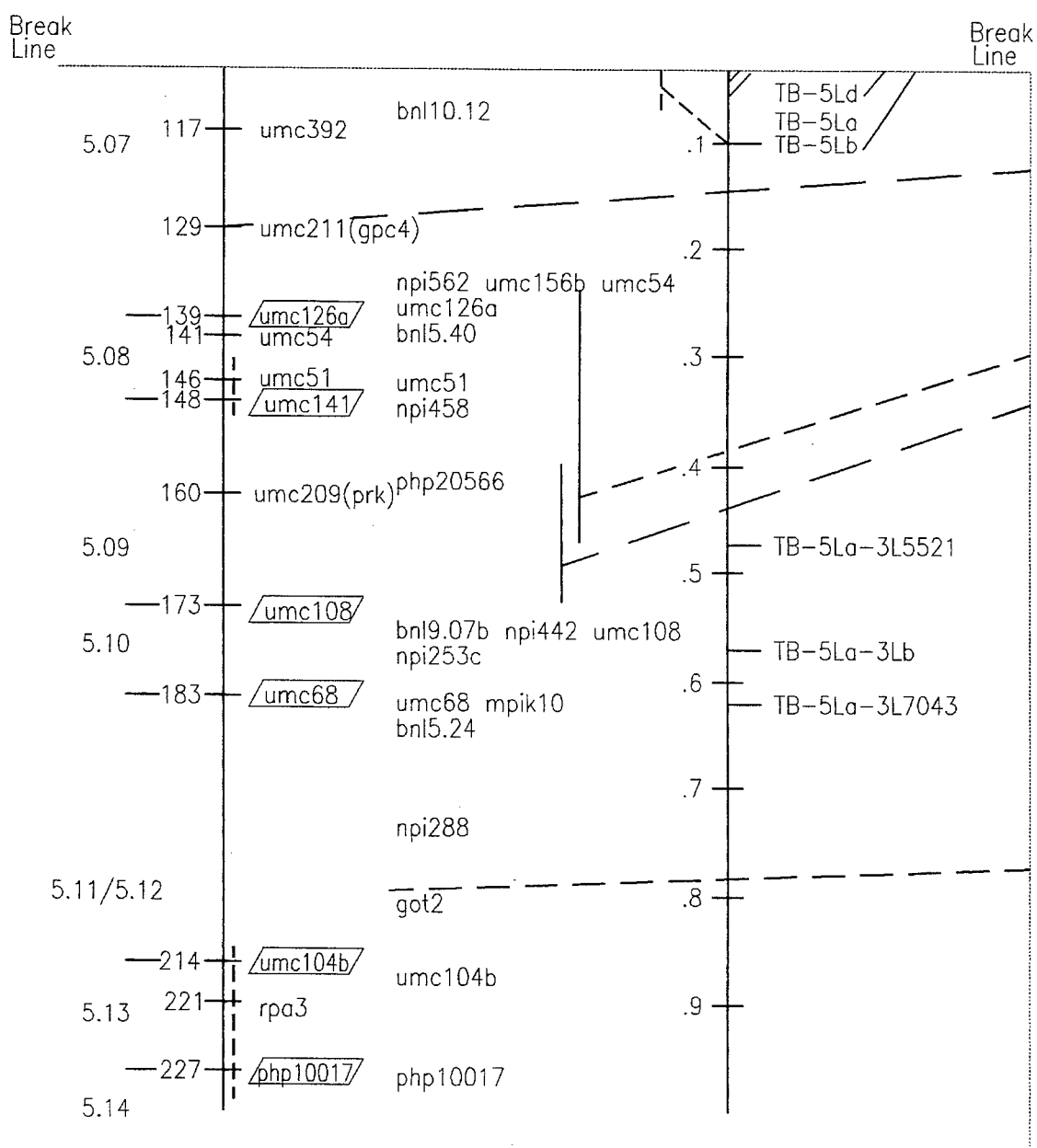
Figures 3, 3E, 4:
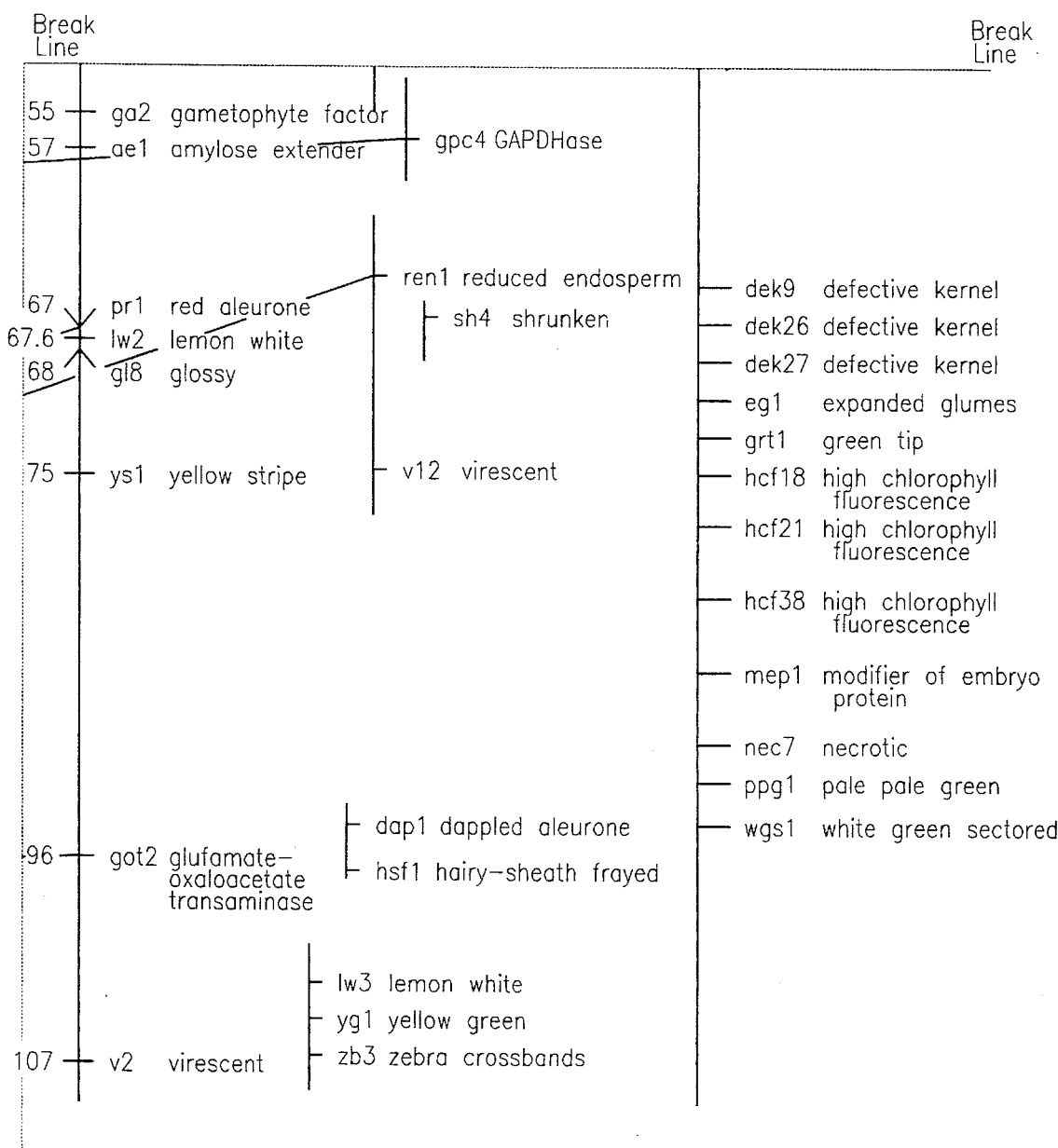
Figures 1, 3F:
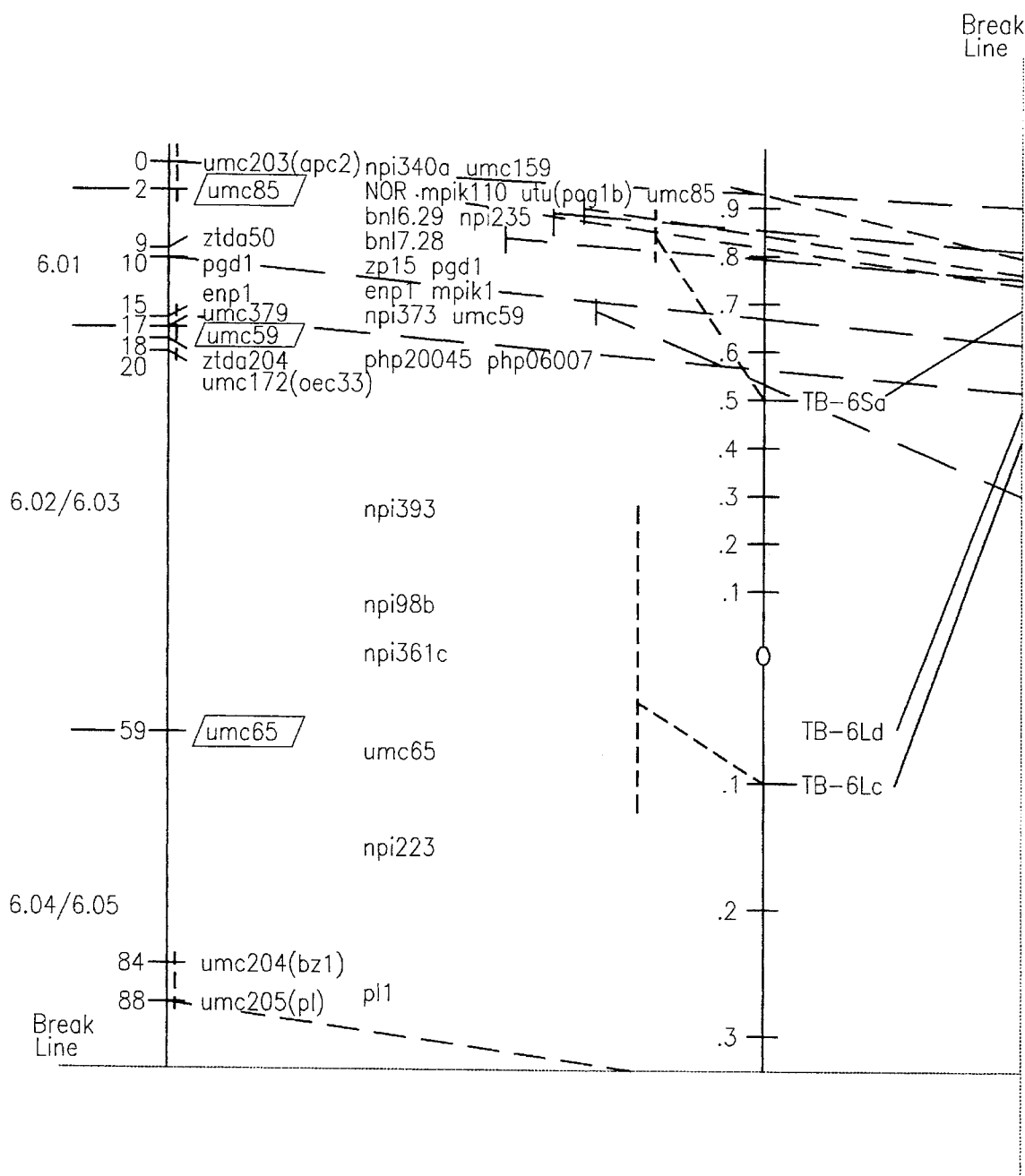
Figures 2, 3F:
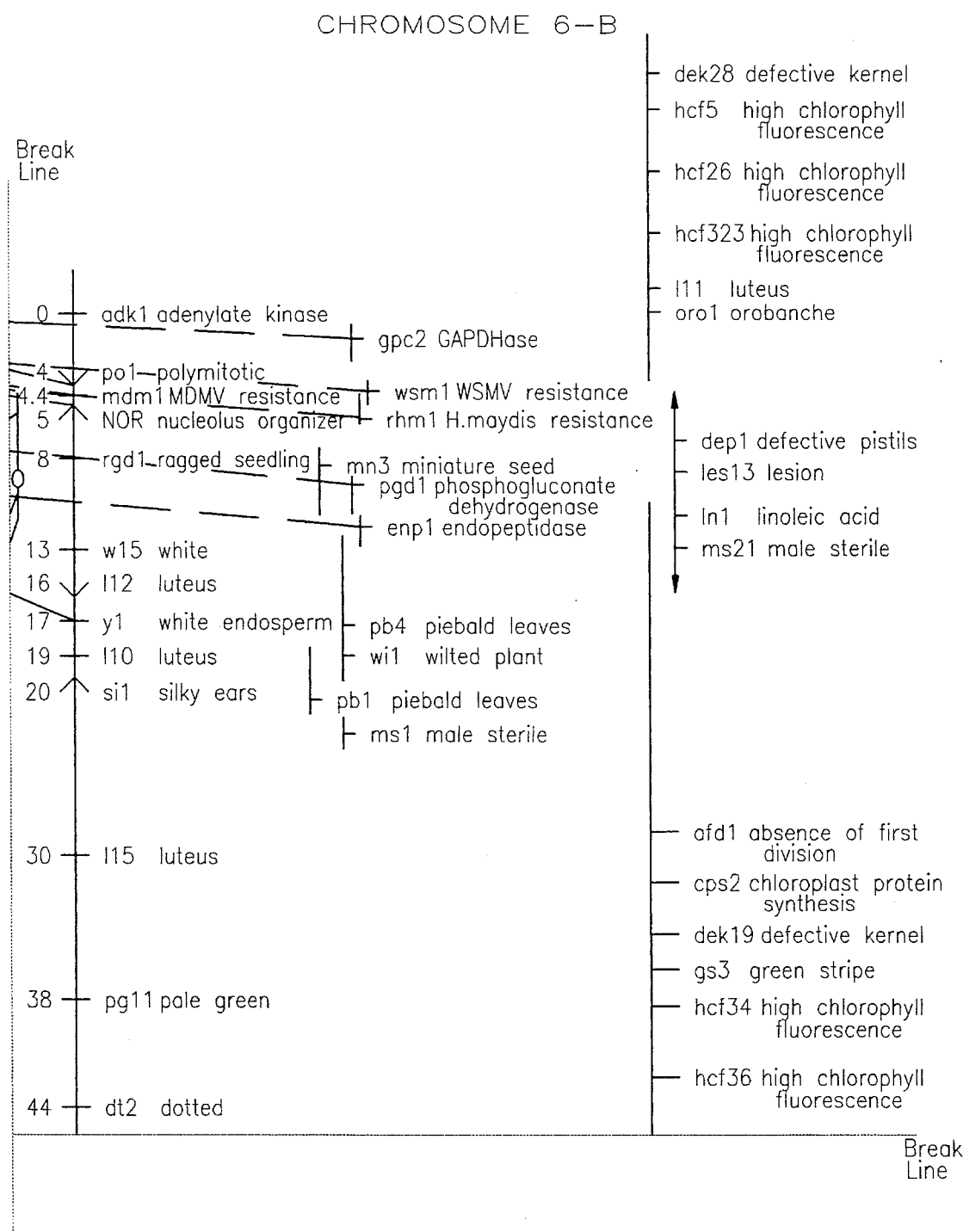
Figures 3, 3F:
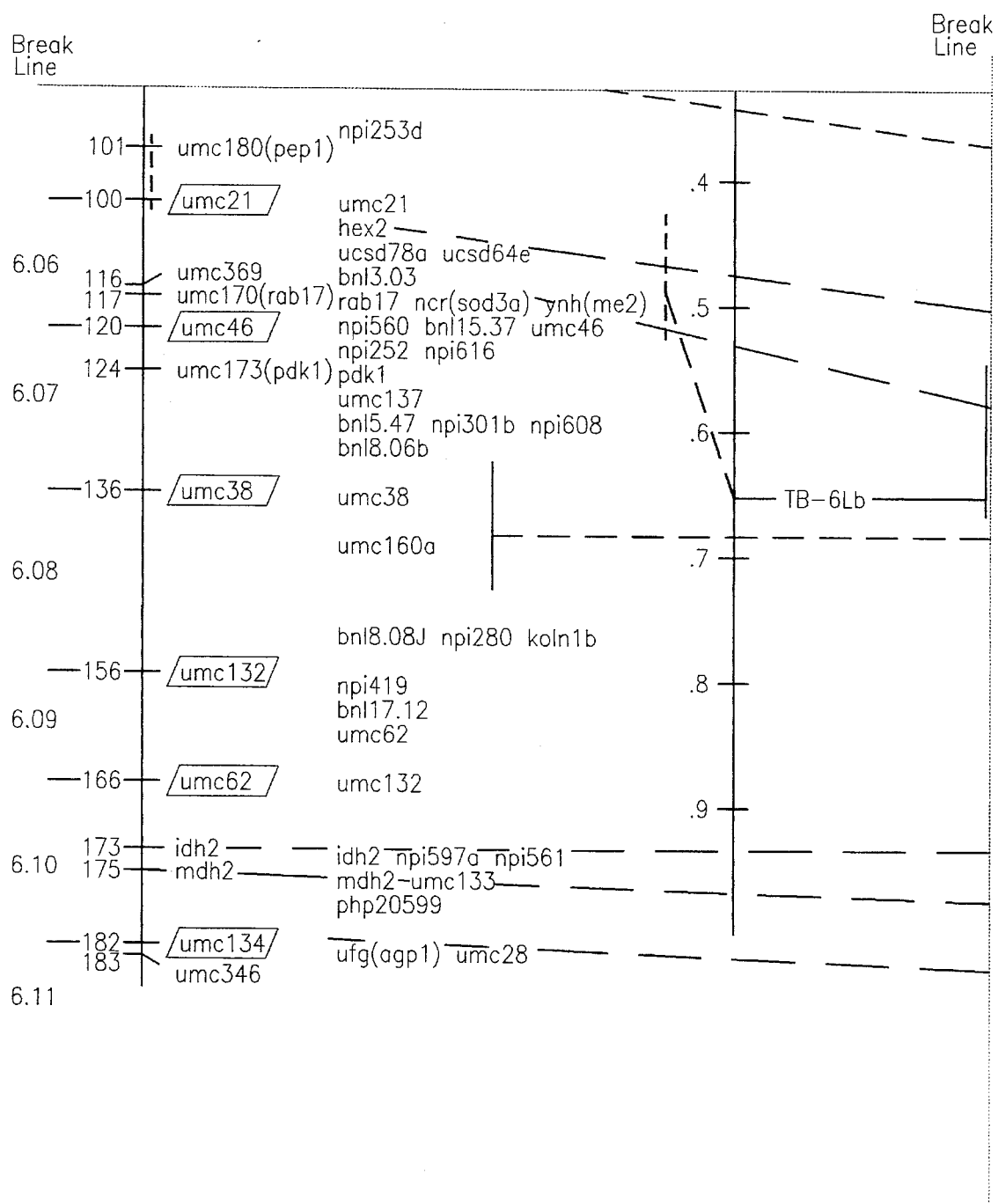
Figures 3, 3F, 4:
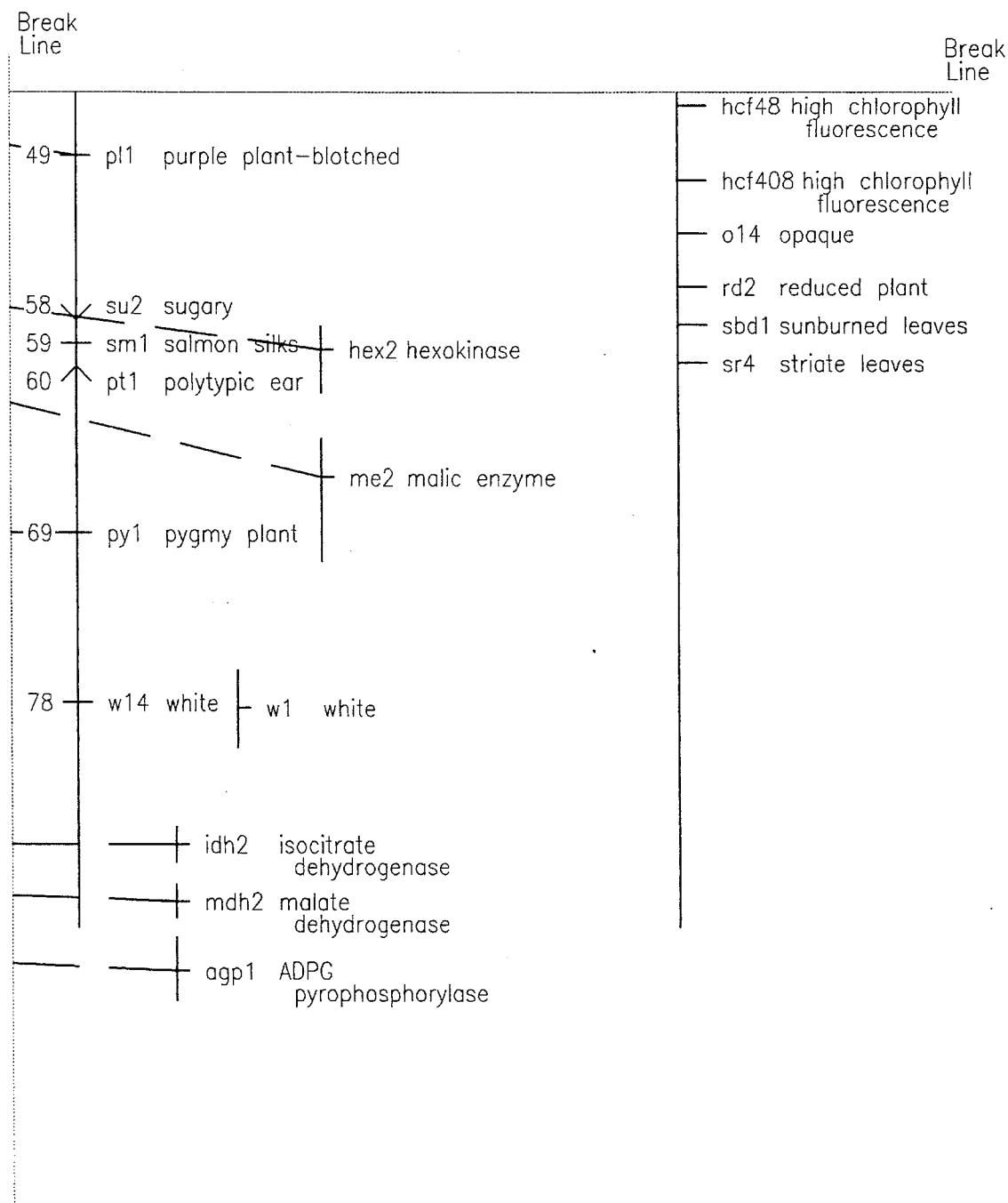
Figures 1, 3G:
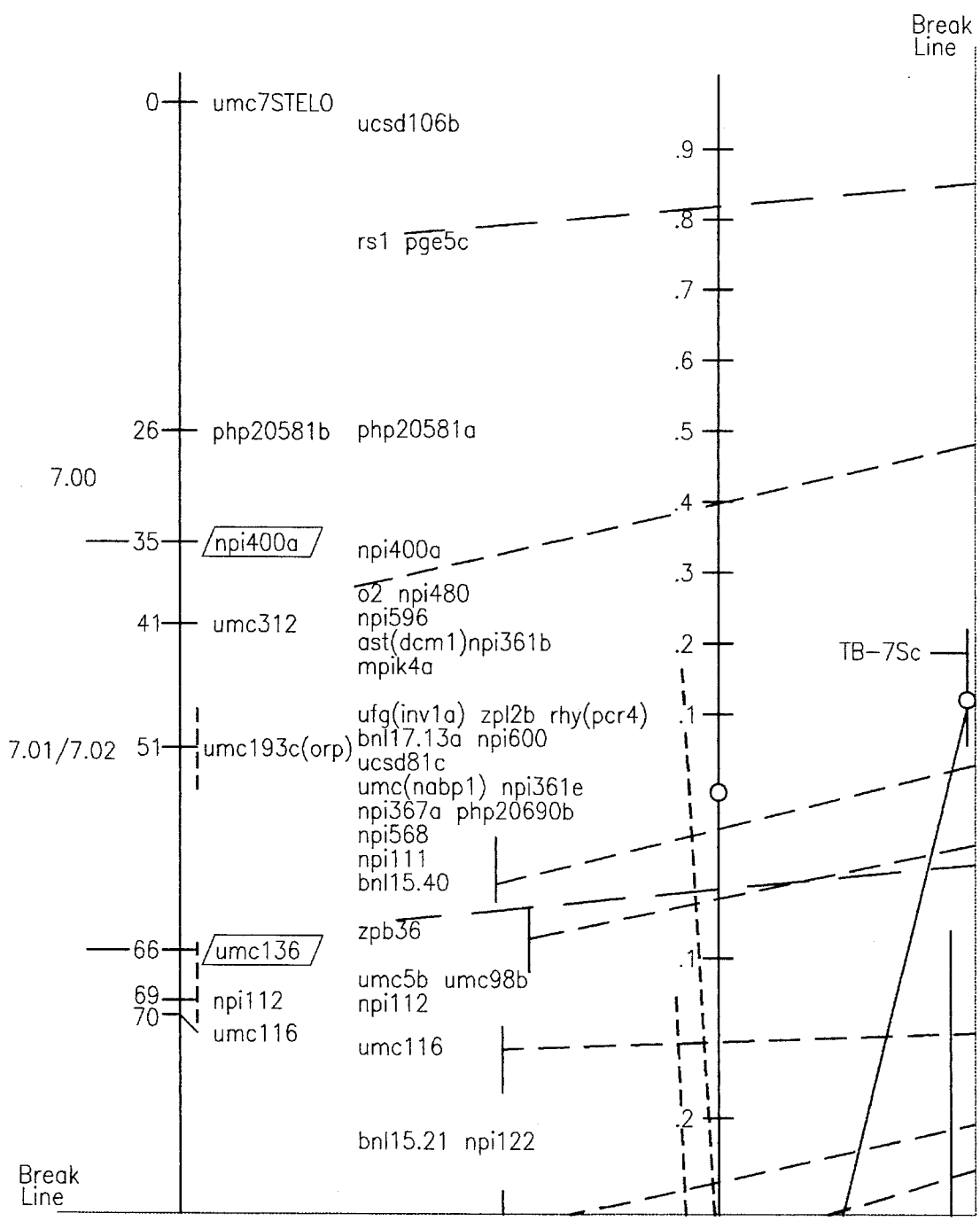
Figures 2, 3G:
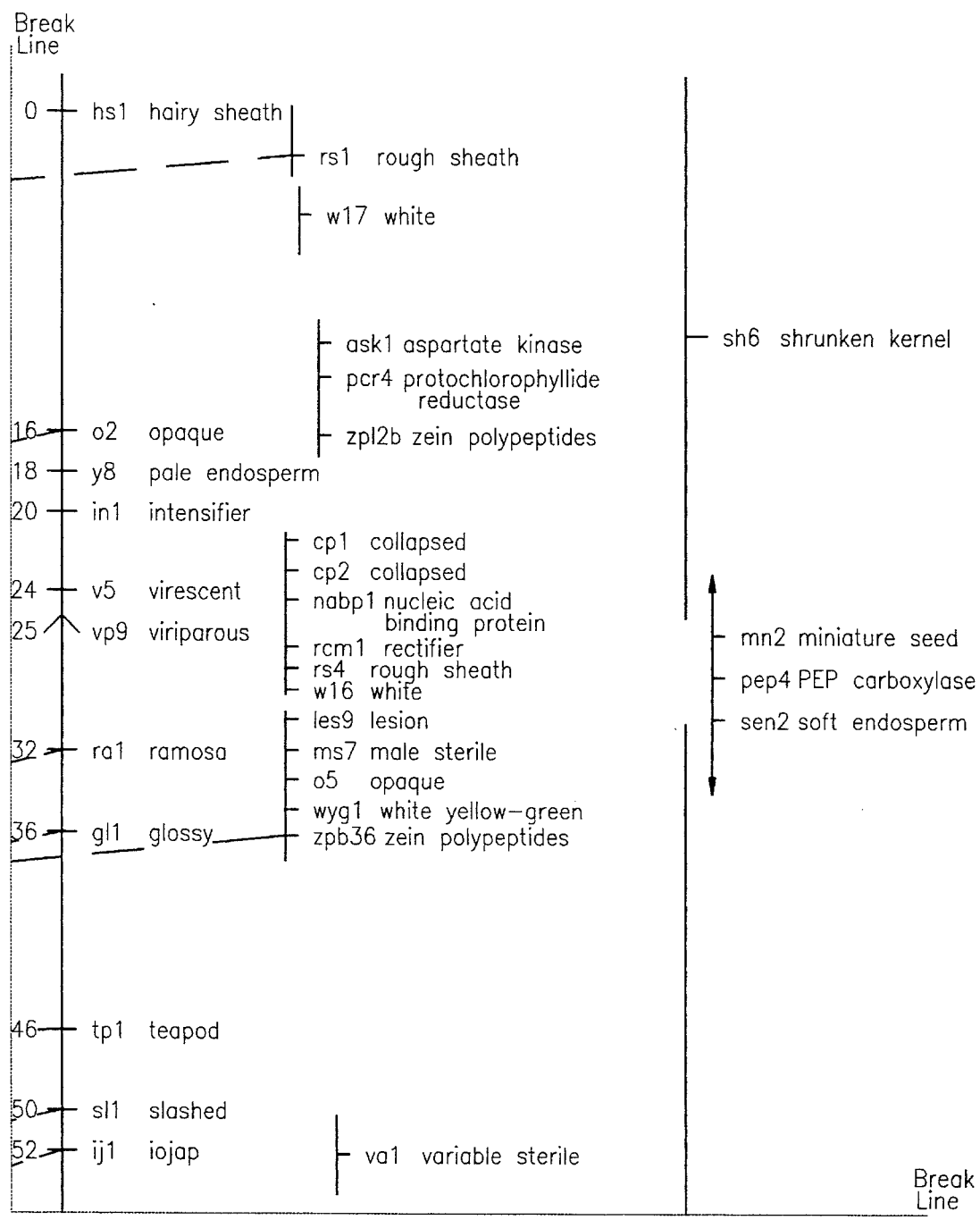
Figures 3, 3G:
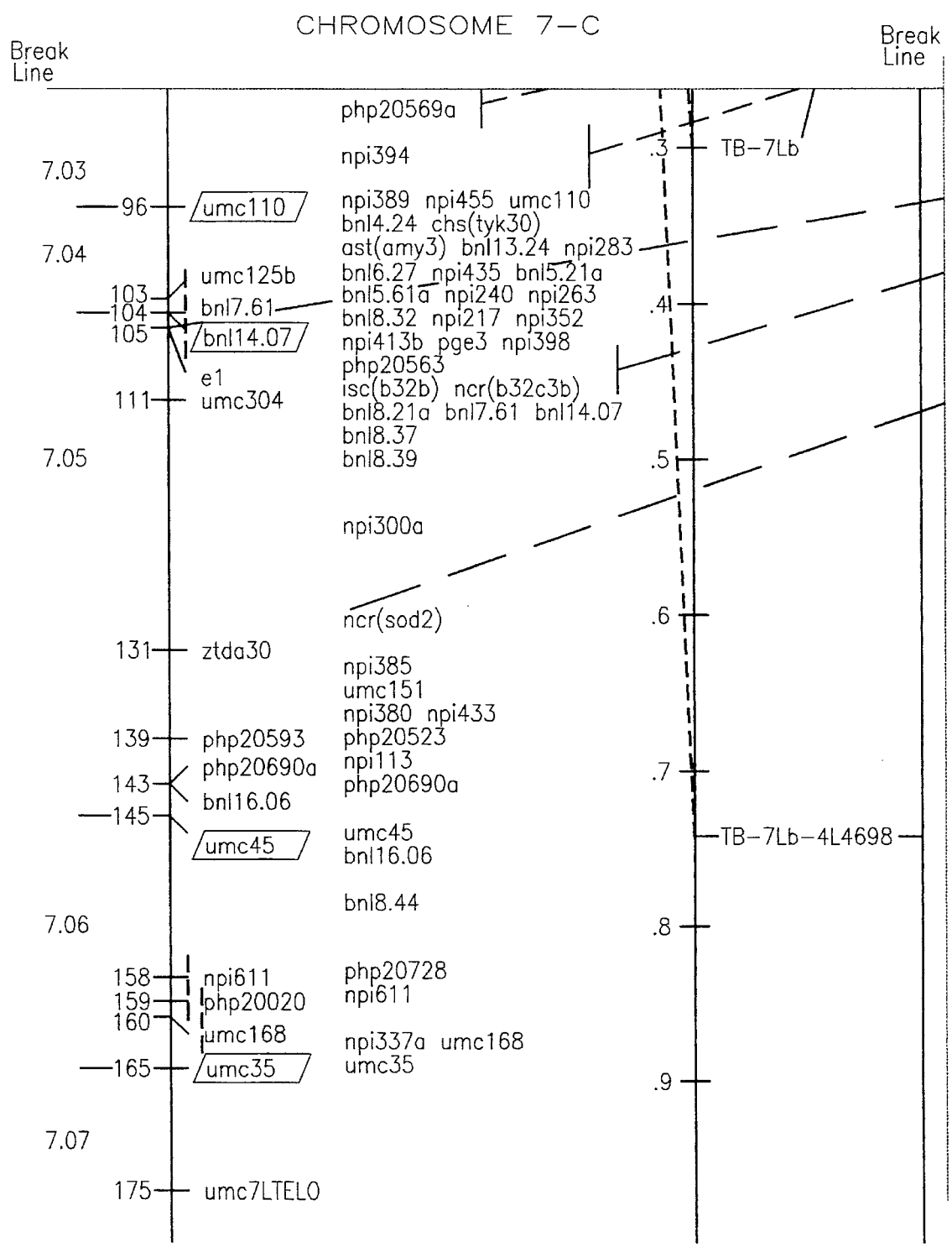
Figures 3, 3G, 4:
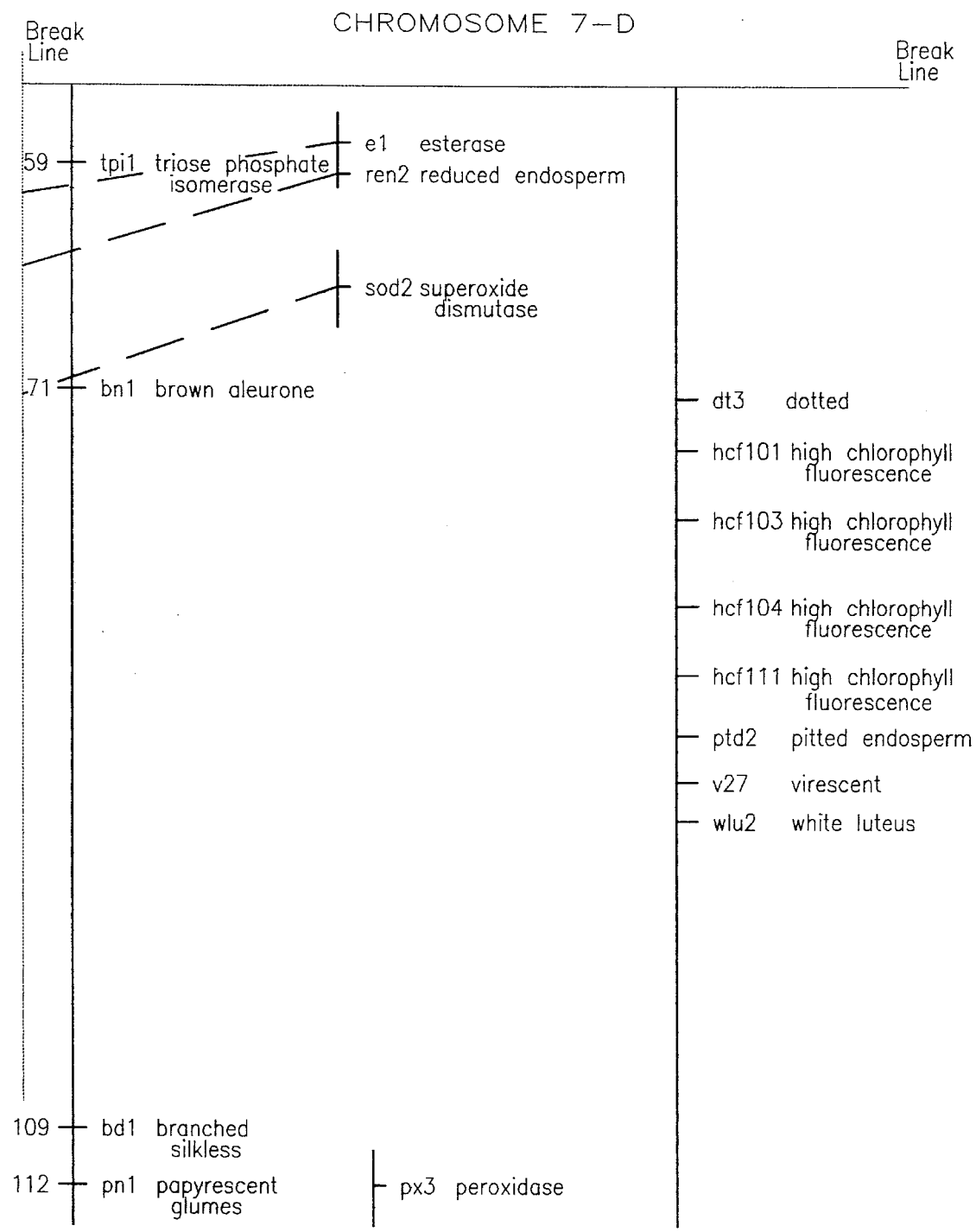
Figures 1, 3H:
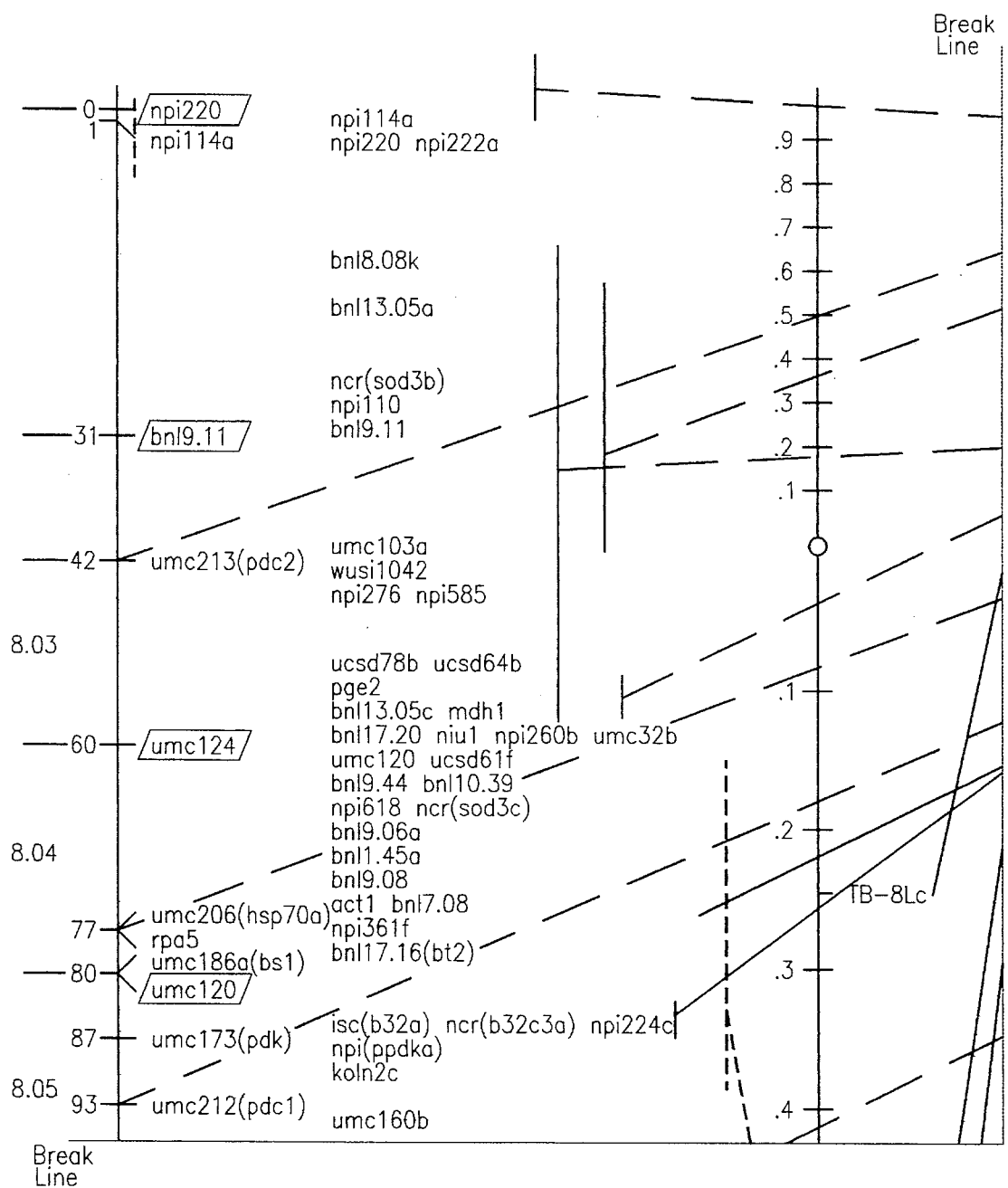
Figures 2, 3H:
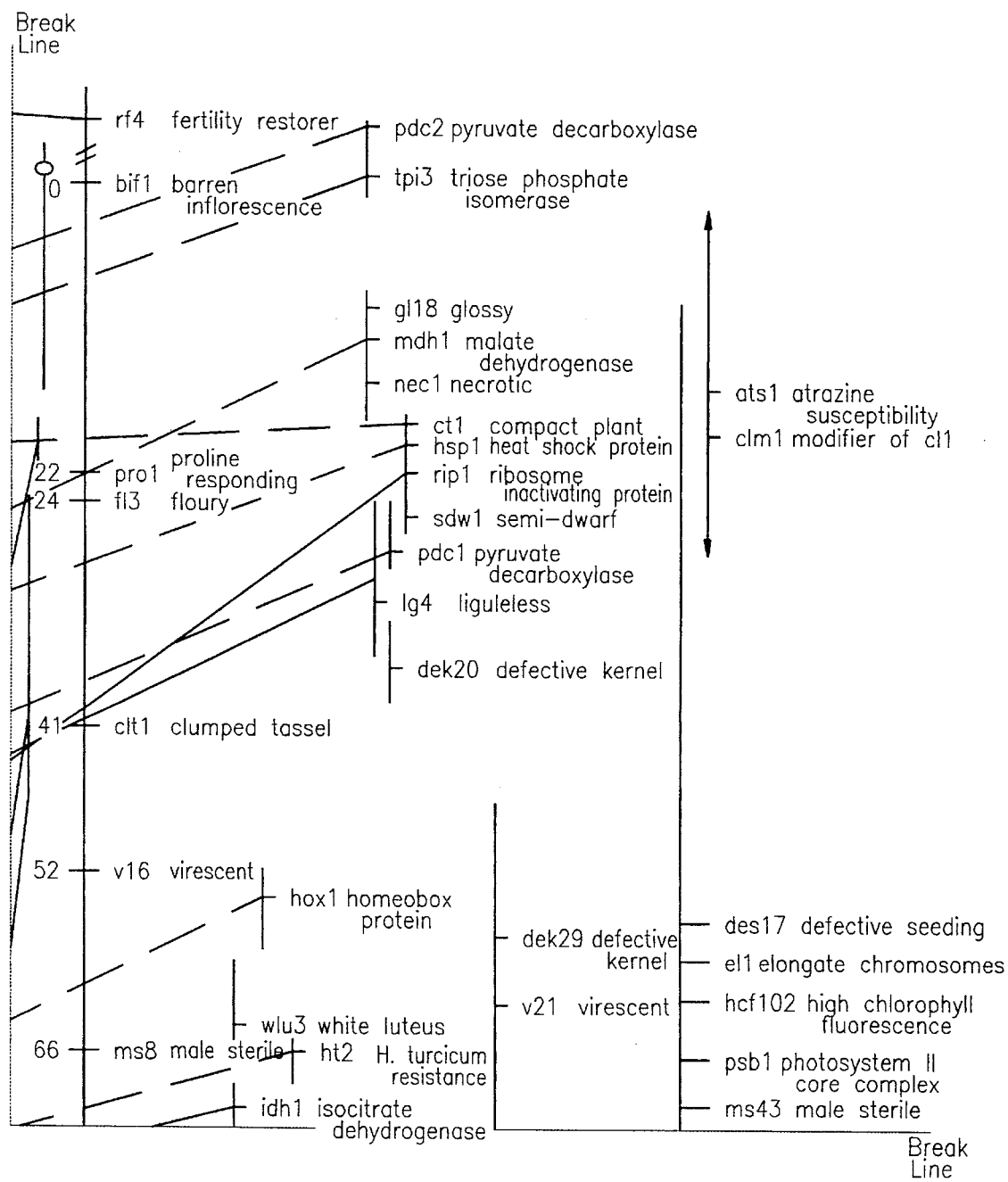
Figures 3, 3H:
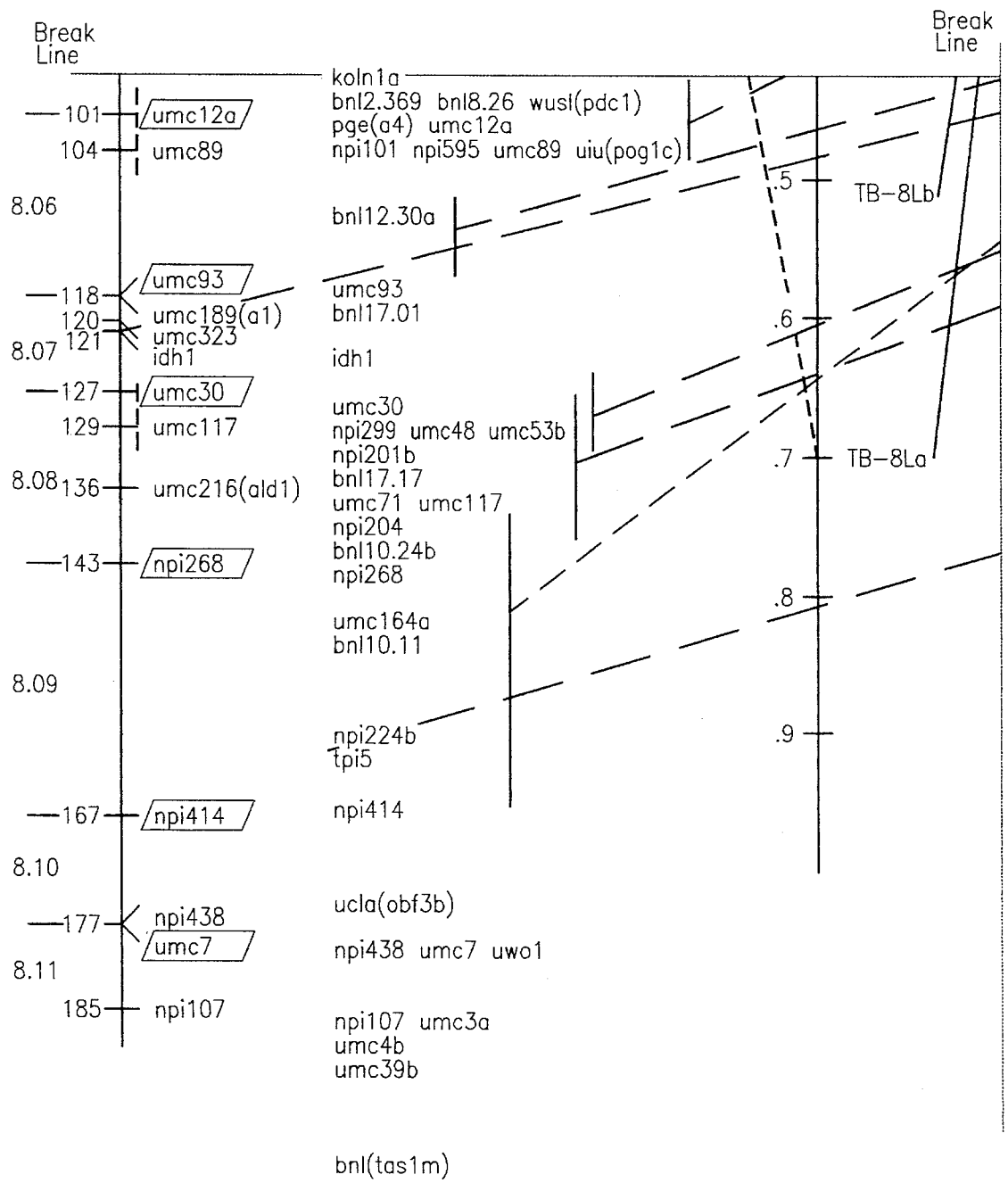
Figures 3, 3H, 4:
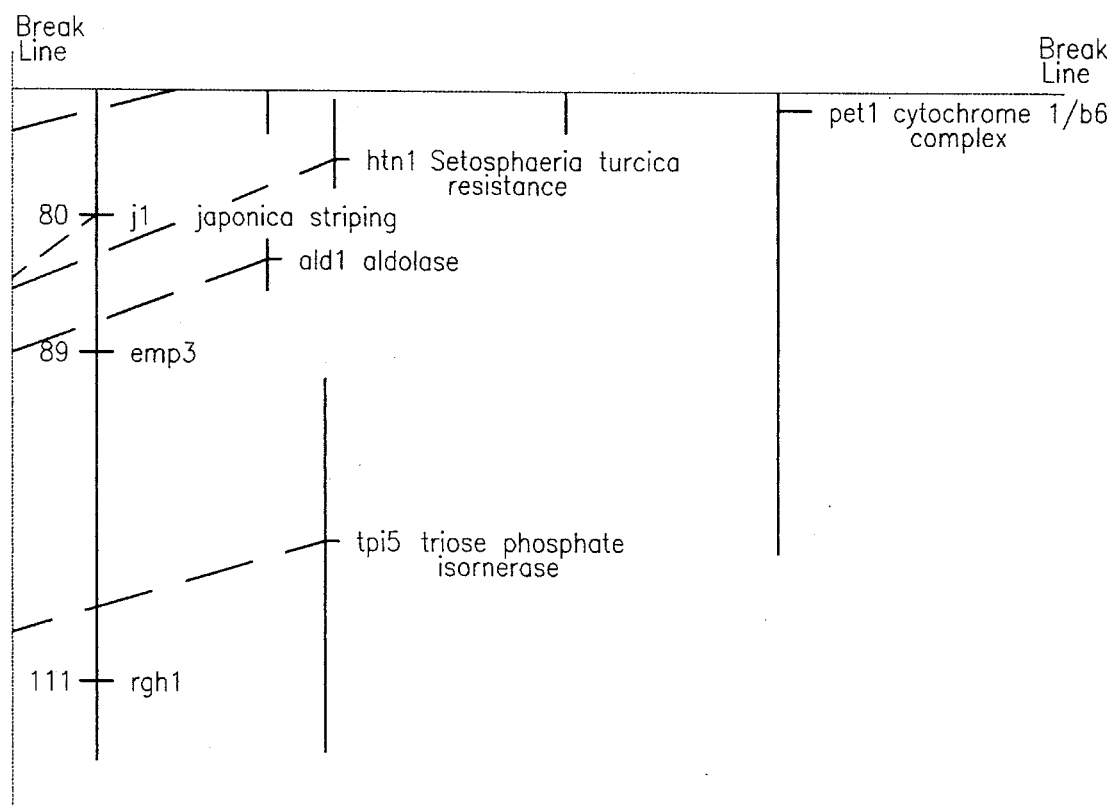
Figures 1, 31:
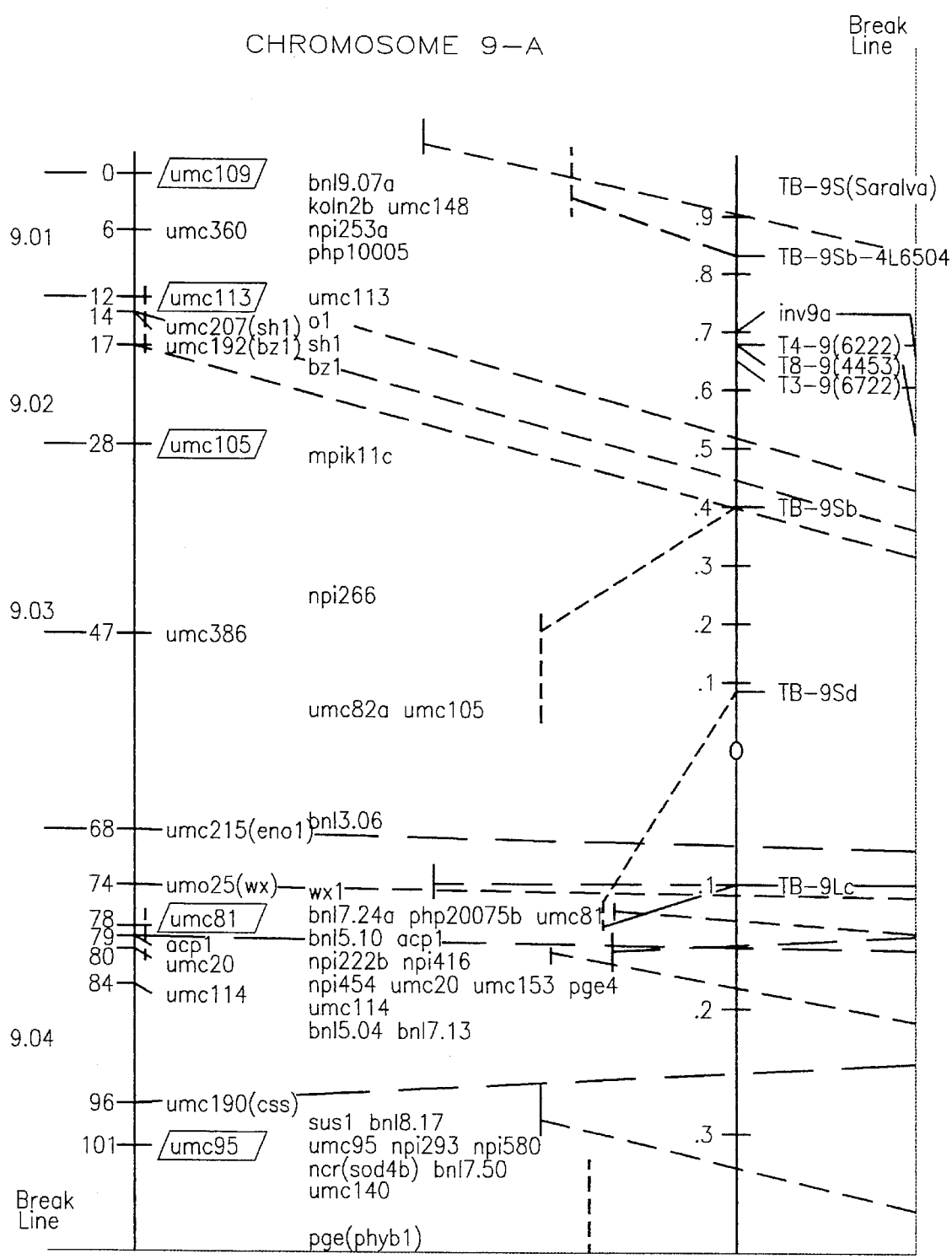
Figures 2, 31:
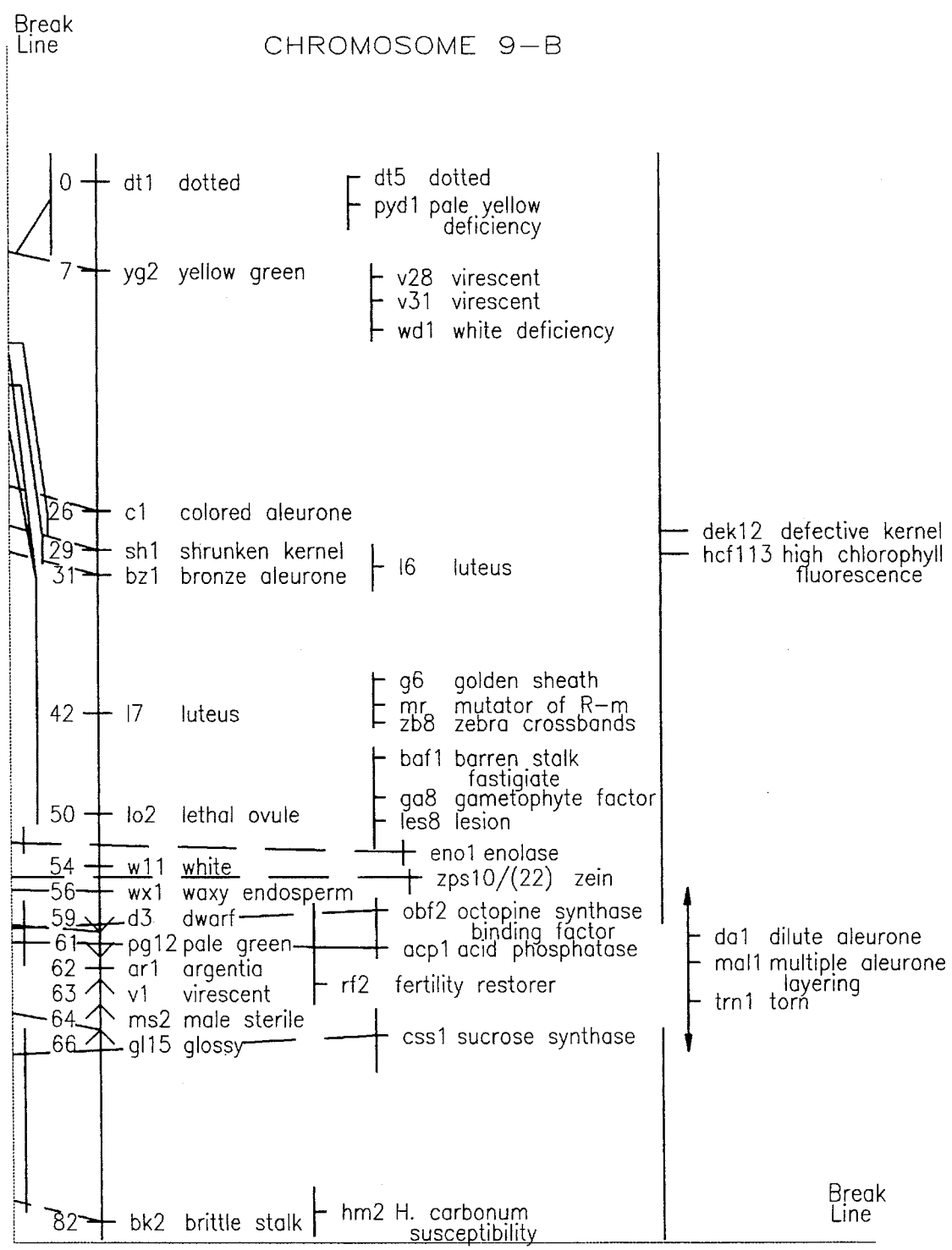
FIG. 2 is a table of data indicating the statistical significance of rating score differences of homozygous RFLP genotypes for each RFLP probe.
Figures 3, 31:
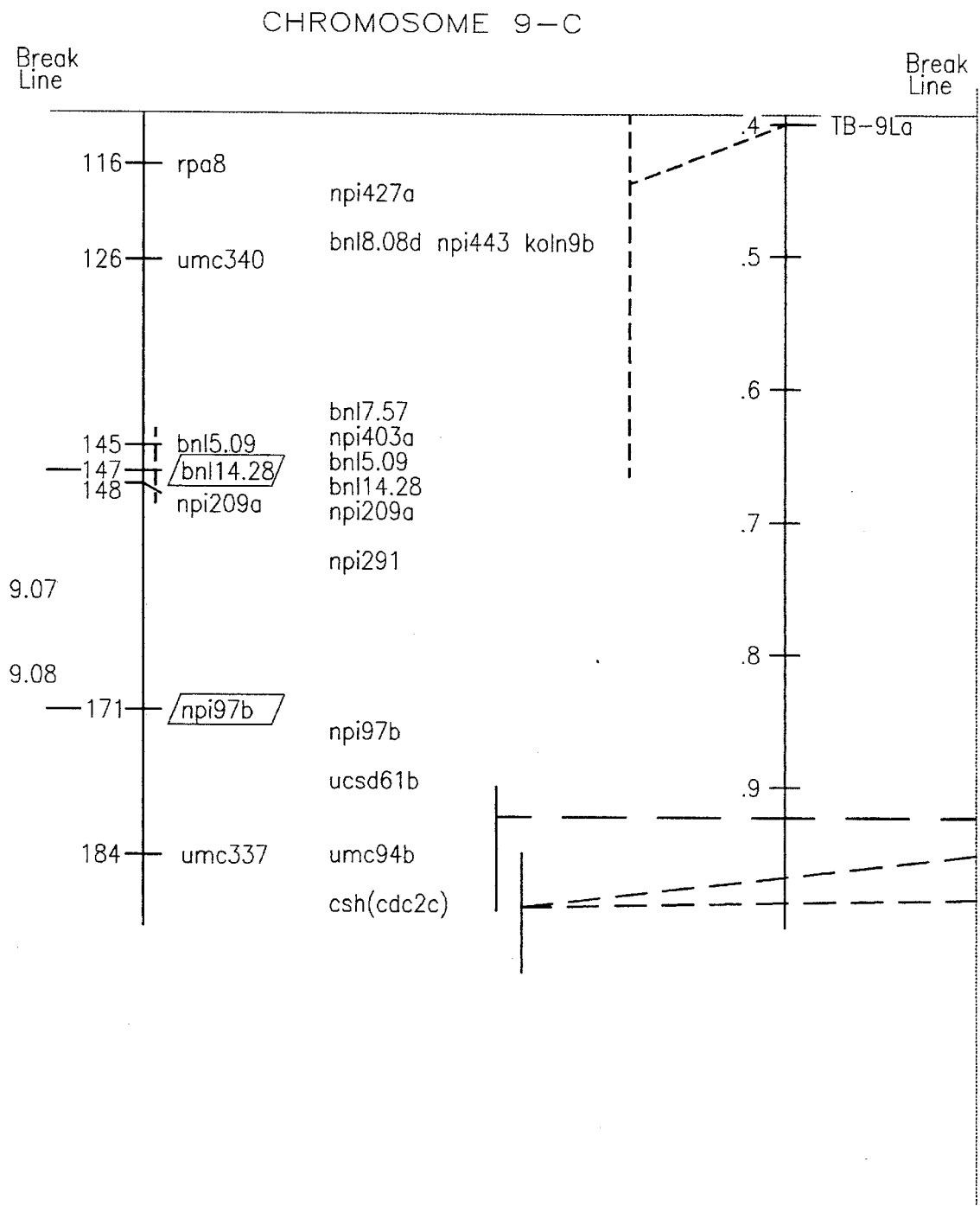
Figures 4, 31:
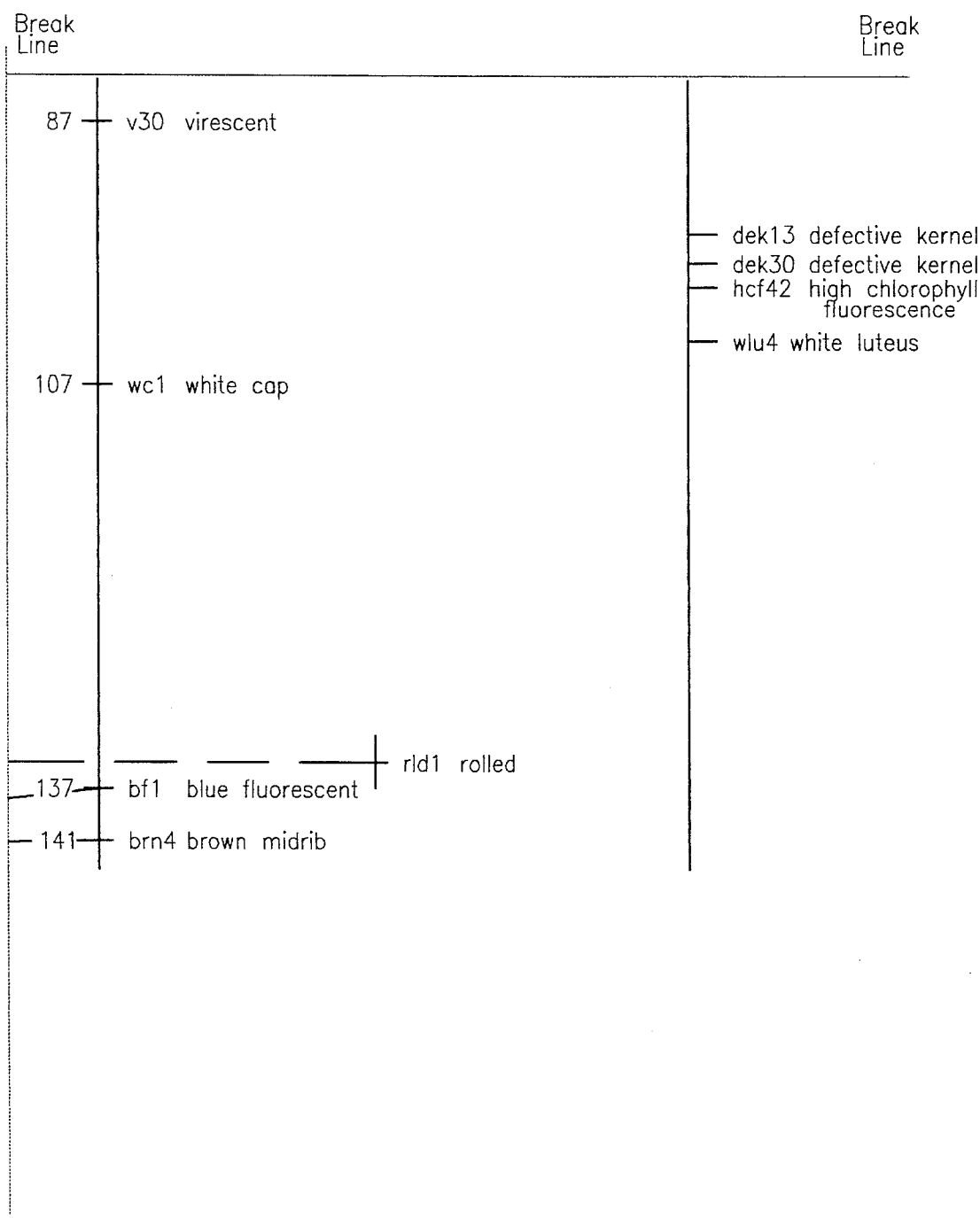
Figures 1, 3J:
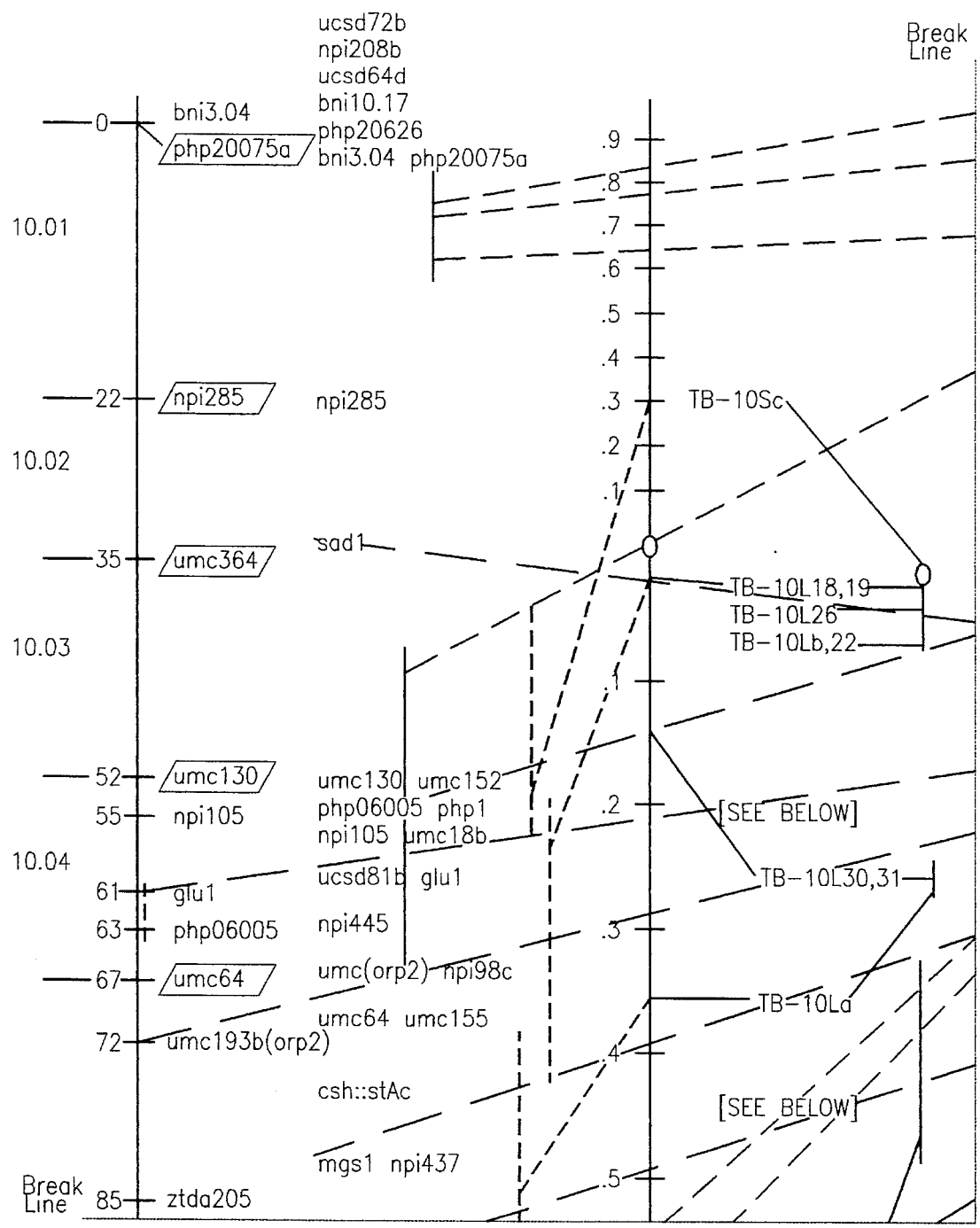
Figures 2, 3J:
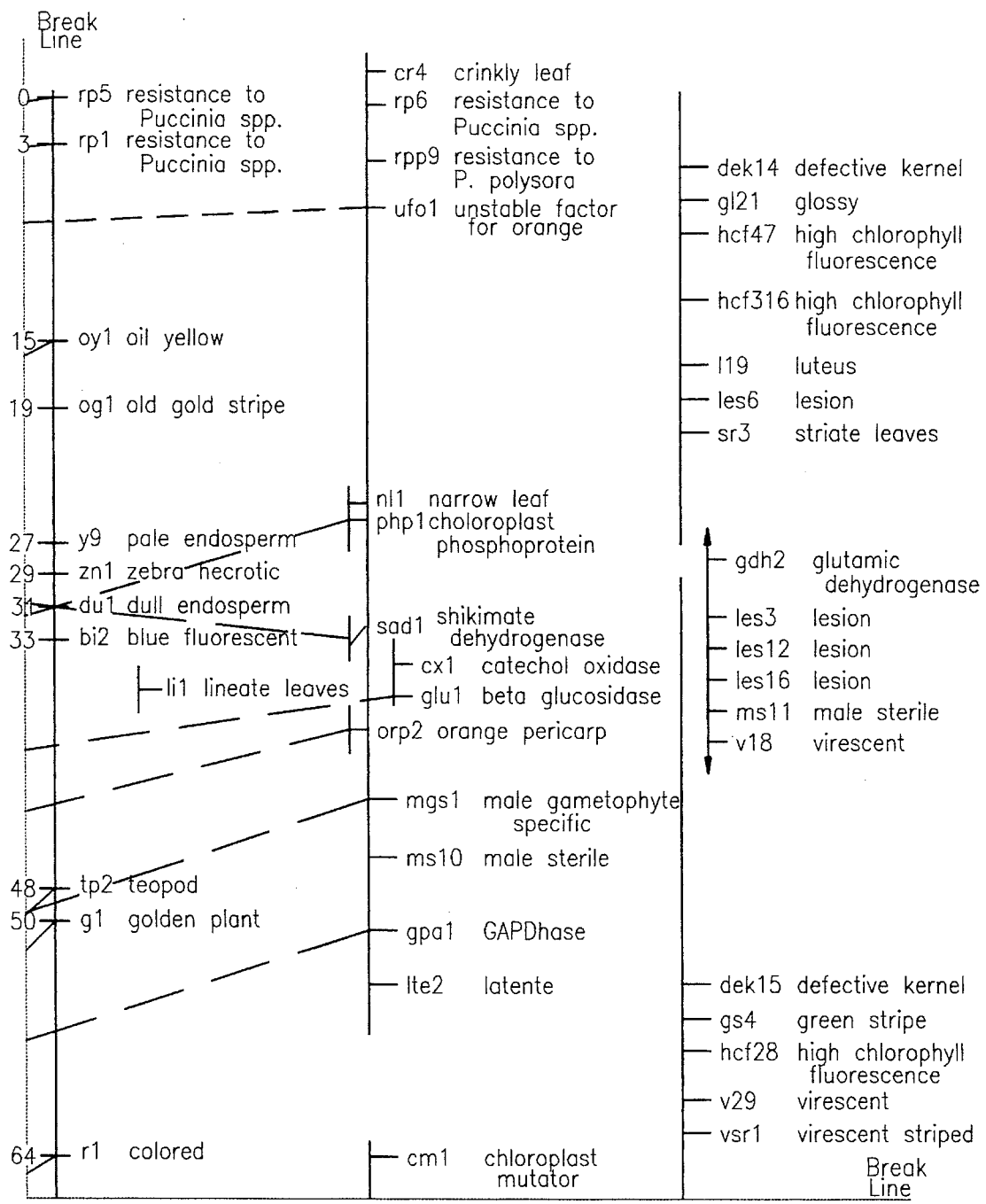
Figures 3, 3J:
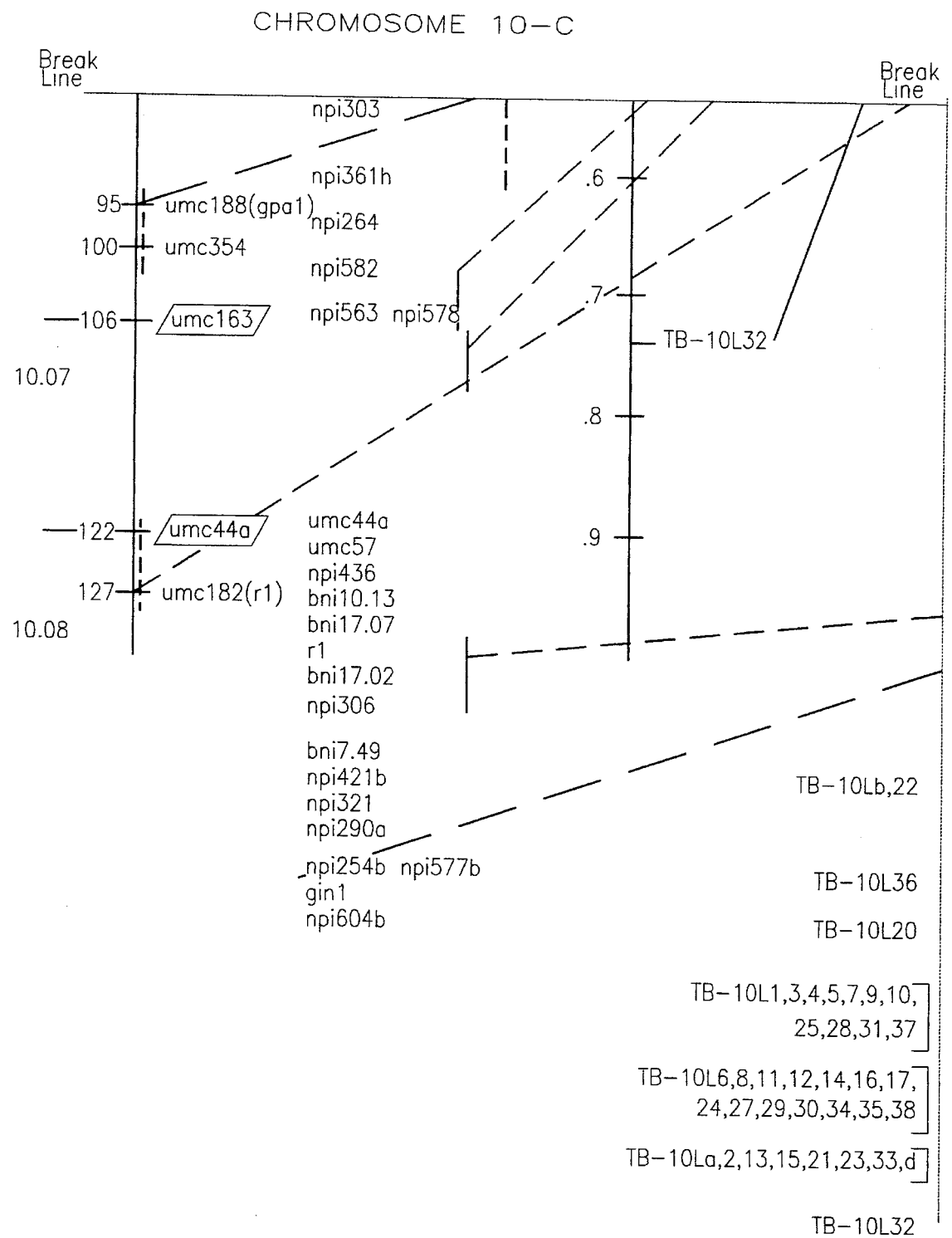
Figures 3, 3J, 4:
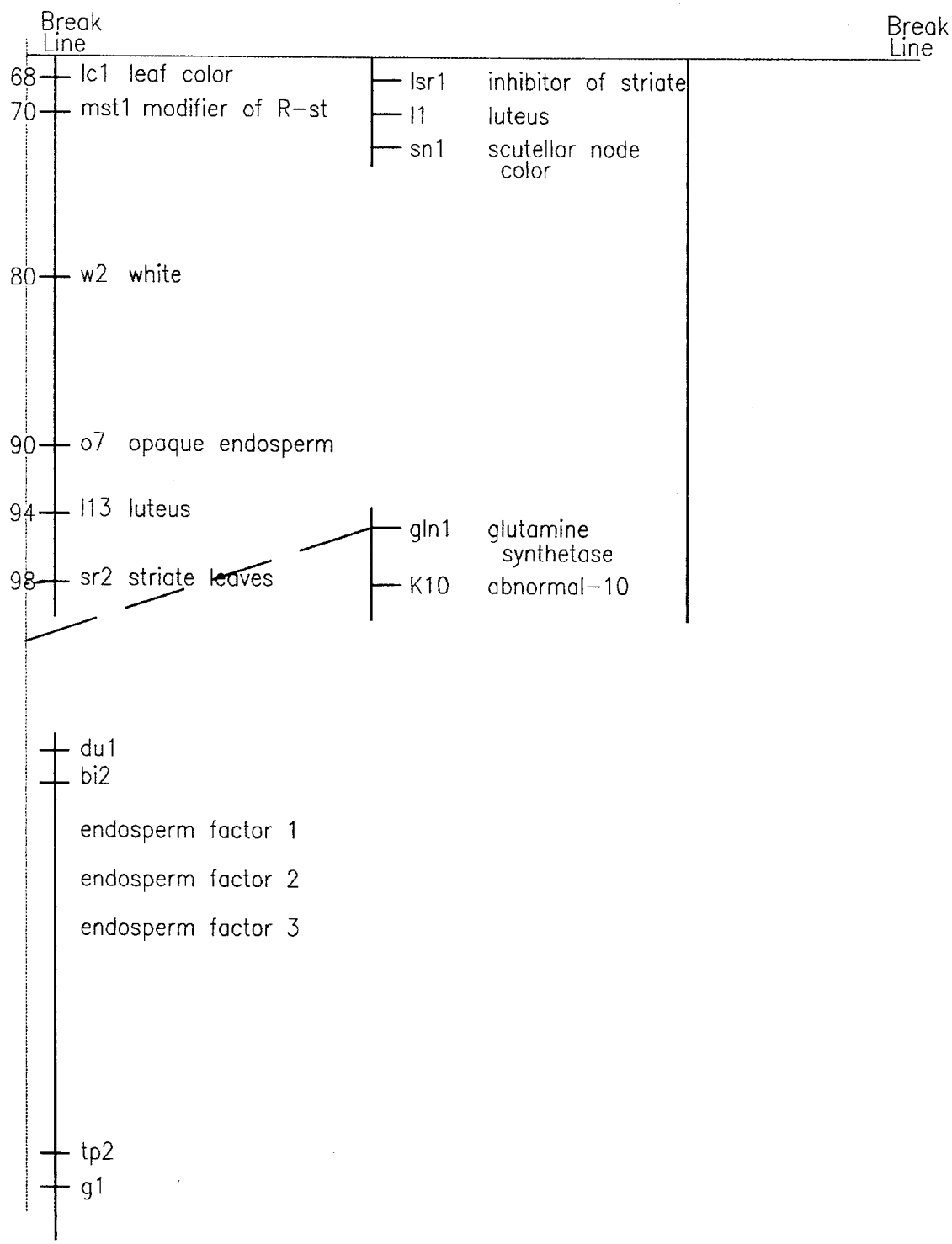
Figure 4A:
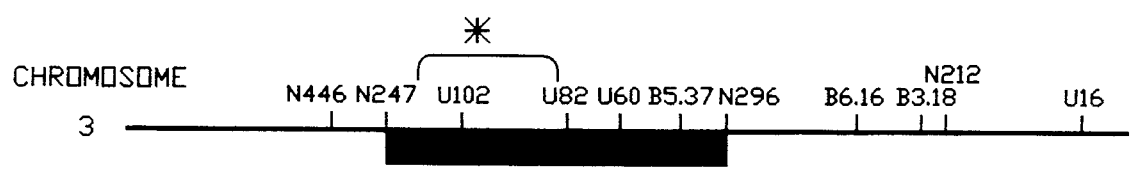
Figure 4B:
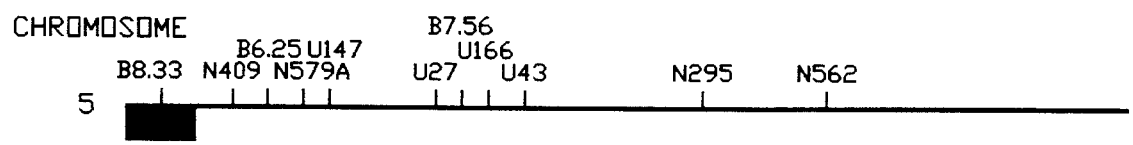
Figure 4C:

Linkage block one, locus 1, is the genetic material carrying resistance to CLN specifically $MDMV_B$ located between flanking probes N0247 and U0082 between map region 45 and map region 106 and more specifically proximate map region 78 on chromosome three (on FIGS. 3). Linkage block one containing the gene or genes associated with resistance to $MDMV_B$ is located on the centromere proximate to the proximal end of the short arm of chromosome three and opposite the proximal end of the long arm of chromosome three. This linkage block and associated probes are shown in FIG. 4. The * line indicates that the gene or genes of interest are most probably located within the enclosed region. The other line indicates that if that region is transferred from the donor parent to a converted inbred the $MDMV_B$ trait will be carried into the converted line.

Linkage block two, locus 2, is the genetic material carrying $MDMV_B$ resistance located proximate B08.33 between map region 0 and map region 14 at UMC147a, more particularly between map region zero and map region three (on FIGS. 3) at probe NPI409. This linkage block is shown in FIGS. 3 and 4 to be proximate BNI8.33 and located on chromosome five on the chromosomal region proximate the distal end of the short arm of chromosome one and upstream of the centromere of chromosome five.

Linkage block three, locus 3, is the genetic material carrying resistance to $MDMV_B$ located proximate probe U0085 on the short arm of chromosome six. This region is also identified as being proximate map region two and between map region zero and map region eighteen more specifically between map region zero and map region nine. This linkage block is also clearly shown in FIGS. 3 and 4.

FIGS. 3 shows a public map having the probes that lay within the linkage blocks of genetic material which give rise to the resistance to CLN and to $MDMV_B$. FIGS. 1 and 2 show the probes that are mapping in the area of interest. If a probe is not available, any substitute probes that map in the map regions in the area of interest can be made and or employed in the scope to the present invention.

Once the linkage blocks were identified, the additional probes which map into the linkage blocks can be utilized to closely define the desired genetic region containing the gene or genes evidencing $MDMV_B$ resistance. It is emphasized that this invention may be practiced using any molecular markers which map in the regions of the map at the locations indicated, provided that the markers are polymorphic for the cross.

Once the chromosomal regions associated with the resistant response to CLN and specifically to $MDMV_B$ were identified, the regions were precisely and accurately introgressed from the MDMV strain B resistant donor into an elite inbred which has desirable agronomic traits. Ultimately, the trait could be introgressed cleanly from one elite inbred into another elite inbred. The resultant hybrids which are resistant to CLN and especially to $MDMV_B$ were produced. It should be understood that a variety of hybrids with this trait have been developed and seed therefore produced and sold to farmers for maize production in CLN and $MDMV_B$ prone areas as well as in other locations.

By virtue of the present invention, it is now possible to use molecular markers to efficiently introgress the CLN and particularly the $MDMV_B$ resistant trait from Pa405 or other germplasm resistant to CLN and particularly to $MDMV_B$ or their ancestors or progeny thereof into elite lines which are not virus resistant.

As stated hereinabove, the objective of this invention is to improve the resistance to CLN through resistance to $MDMV_B$ of elite breeding lines without substantially affecting their combining ability. The term "elite" is a term of the art and its meaning is well known. Many factors contribute to the elite nature of breeding lines but of these factors the yield, in hybrid combination, and the moisture content of the seed, percentages of root and stalk lodging are of primary importance. In performing this invention, then, the introgression of the resistant trait can be monitored from generation to generation and, most importantly, the progressive restoration of the genetic background of the elite germplasm may also be observed. The best selections made by using RFLP fingerprinting ultimately require either or both field or greenhouse testing with CLN and/or $MDMV_B$ infection in order to confirm the resistance trait and establish the elite character derived from the elite parent germplasm. Pursuant to this invention the number of lines requiring such testing is very low compared with the very high numbers which would otherwise be required. Ideally, the product line should have the same combining ability as its elite non resistant parent combined with the resistant character of its resistant parent.

The principal feature of this invention is the transfer of genes from a relatively resistant donor to a relatively non resistant recipient. However, the level of resistance of the donor and recipient lines is, of course, relative and the relatively non resistant recipient may itself possess resistance genes which may usefully be retained in the genome of the improved lines.

The following example outlines the introgression of the identified linkage blocks into various inbreds designated CLN and/or $MDMV_B$. Both 563 and 211 are yellow dent maize inbreds. The introgression of the desired linkage block resulted in improved inbreds designated "$211_{CLN.1-4}$" and "$563_{MDMVB.44}$" and "ZS19".

The following example outlines the introgression of the three linkage blocks into 211. Linkage block two was already present and only needed to be retained. Linkage blocks one and three on chromosome three and six were introgressed into 563 to develop 563CLN. The effect of linkage block two from 211 was minor and therefore it was not introgressed into 563. Both 211 and 563 contained elite inbred material that has agronomically desirable traits including low percentage of moisture, root lodging and stalk lodging, and high yield results. It should be understood that introgression of linkage block one into a $MCDV_A$ is within the scope of this invention as long as the resultant plant evidences $MDMV_B$ and/or CLN resistance. Likewise, the use of conventional breeding techniques to transfer the trait from elite inbreds into other germplasm is contemplated.

The gene action on chromosome three from donor parent Pa405 marked by flanking probes N247 and N296 and more specifically by N247 and U82 is partially dominant. The gene action on chromosome six from donor parent Pa405 located proximate probes U85- B6.29 is dominant. Surprisingly, gene action on chromosome five was not, as would be expected, from the resistant parent Pa405 but instead was from the susceptible parent 211. This chromosomal region is proximate B8.33- N409 and the gene action is partially dominant to dominate. The 211 chromosomal material had a more minor impact on the plant's ability to resist $MDMV_B$ and CLN and therefore it was not introgressed into all CLN resistant plants.

In the corn breeding nursery the following plants were grown: 563 was crossed as a female with Pa405 forming a population 563/Pa405. The seed from the cross between 563 and Pa405 was encoded 563/Pa405. This was an $F_1$ generation. The seed was planted in a winter nursery in Hawaii where it was selfed to produce to $F_2$ generation encoded 563/Pa405)x. The seed from the $F_2$ generation was exposed to the aforementioned $MDMV_B$ screening procedure to determine specific plant reactions. Separate plants were identified as a result of the screen as having non-symptomatic expression. These plants were backcrossed to 563. Plant 606 appeared to have the best genetic makeup and resistance combination and was selected. The newly created backcross one (BC1) was designated 563BC1. It was grown and the plants were sampled for DNA. Those with the appropriate CLN, specifically $MDMV_B$, regions were selfed creating BC1S0 (backcross one self zero). Samples were taken. Plants were selected based on RFLPs analysis of chromosome three and six. The selected plants were again selfed creating BC1S1. This process of screening and RFLP selection was repeated until the BC1S5 was developed. This cross was homozygous for the trait at linkage blocks one and three located on chromosome three and chromosome six and evidenced resistance to $MDMV_B$ when screened. This germplasm was designated ZS19. When BC1S3 was completed various plants appeared to have potential, i.e. they were still segregating but evidenced good resistance on the screens. One of these plants designated $563_{MDMV.44}$ was also selected out and repeated selfed to eliminate segregation and to develop homozygosity and created $563_{MDMVB.44}$.

In a similar fashion at the BC1S5 stage in a 211/Pa405 cross four plants were selected. These plants designated $211_{CLN.1}$, $211_{CLN.2}$, $211_{CLN.3}$, and $211_{CLN.4}$ were developed to elite inbred stage by selfing.

As shown in FIG. 5 at the BC1S3 stage the progenitor of ZS19 "ZS71" and the progenitor of $563_{MDMVB.44}$ "ZS44" and the progenitor of $211_{CLN.3}$ $211_{CLN.2}$ and $211_{CLN.1}$ "ZS13" and "ZS51" the progenitor of $211_{CLN.4}$ were used in tester hybrid combinations. ZS71 X 211, ZS44 X 211 and ZS13 X 563, and ZS51 X 563 were tested for CLN resistance.

Please note that the $MDMV_B$ converted inbreds were not homozygous, i.e. still segregating, in the resistance linkage blocks and the inbred used to make the hybrid was susceptible. In spite of these segregating issues, the tester hybrid combinations were substantially more resistant to CLN than were the original unconverted hybrid 563 X 211 which scored 90.0% infection and a rating of 1.25 compared with the ancestor of ZS19 at 5.0% and 7.25 and the ancestor of $563_{MDMVB.44}$ at 5.0% and 7.25. The ancestor of $211_{CLN.3}$ scored 42.5% vs. 90% and 3.75 vs. 1.25 for the unconverted inbreds in the hybrid tester combination. Likewise, the ancestor of $211_{CLN.1}$ scored 52.5% vs. 90% and 3.75 vs. 1.25. These tester hybrids also showed substantially more resistance than did to commercially available hybrids 3162 and 3245 at 82.5% and 97.5% and 2.00 and 1.25, respectively. The tester hybrids were not quite as resistant as the standard resistant check using the Pa405 donor. This is believed due to lack of homozygosity.

The transfer of the CLN resistance through the $MDMV_B$ trait to a hybrid is effected by crossing two inbred lines, male and female, at least one having the chromosomal region on chromosome three and one having the chromosomal region on chromosome six of homozygous genetic material. It should be understood that both male and female could have a full complement or a partial complement of the genetic material.

Pragmatically because the two primary linkage blocks on chromosomes 3 and 6 are dominant or partially so and not recessive fixing the trait in a hybrid requires only the fixing of a first inbred line. The crossing of two inbreds both having the chromosomal regions fixed may make a slightly more resistant plant since chromosome three is only partially dominant.

It would achieve the greatest $MDMV_B$ resistance in the resultant plant if both male and female parent inbreds were fixed for all three gene locations. This, however, greatly limits the flexibility of a corn breeding program as each parent of the hybrid requires introgression of all of the chromosome material. To this end, the use of one fixed inbred line is the usual choice, though fixing the genetic material on both sides of the hybrid may be advisable if the hybrid is marketed into regions where CLN and $MDMV_B$ are prevalent. In most other areas less prone to virus devastation, a highly tolerant hybrid to $MDMV_B$ is sufficient to combat the disease problem.

Although the foregoing invention has been described in some detail by way of illustration and example for purposes of clarity and understanding, it will be obvious that certain changes and modifications may be practiced within the scope of the invention.

We claim:

1. An improved inbred maize plant comprising a genome, homozygous with respect to genetic alleles situated on chromosomes 3 and 6 which are nonnative to a first parent of said improved inbred and native to a second parent of said improved inbred, said second parent selected from Pa405, resistant progeny or resistant hybrids thereof and wherein the improved inbred has resistance to $MDMV_B$ not significantly different than that of the second parent in the same hybrid combination, and yield and moisture characteristics which are not significantly different than those of the first parent in the same hybrid combination.

2. A plant according to claim 1 which is homozygous at each of said loci.

3. A progeny of the maize plant according to claim 2, said progeny being a hybrid from a cross between first and second inbred lines, having alleles conferring resistance to $MDMV_B$ being present in the homozygous state in the genome of one or other or both of the first and second inbred lines such that the genomes of the first and second inbreds together donate to the hybrid a complement of alleles necessary to confer resistance to $MDMV_B$.

4. A maize plant and parts thereof having resistance to MDMV Strain B, in a non-Pa405 genomic background, the genome of which contains alleles from the group consisting of Pa405, resistant progeny and resistant hybrids thereof associated with MDMV Strain B resistance said maize plant having at least two loci, one of said loci being chromosome 3 between map unit 45 and map unit 106, reference to map units and chromosome locations as set forth in the maize chromosome map published for the 1993 Maize Genetics Corporation Newsletter, Mar. 15. 1993 at FIG. 3.

5. A maize plant and parts thereof, according to claim 4, wherein one of said loci being chromosome 6 between map unit 0 and map unit 18.

6. A maize plant, according to claim 4, wherein said loci are proximate map unit 78 on chromosome 3.

7. A maize plant, according to claim 5, wherein said loci are between map unit 0 and map unit 9.

8. A maize plant, according to claim 4, that exhibits resistance to a synergistic combination of $MDMV_B$ and MCMV.

9. A progeny according to claim 3, that exhibits resistance to a synergistic combination of $MDMV_B$ and MCMV.

* * * * *